US006511666B1

(12) United States Patent
Reynolds et al.

(10) Patent No.: US 6,511,666 B1
(45) Date of Patent: Jan. 28, 2003

(54) DIAGNOSTICS AND TREATMENTS OF PERIODONTAL DISEASE

(75) Inventors: Eric Charles Reynolds, North Balwyn (AU); Peter Singh Bhogal, Point Lonsdale (AU); Nada Slakeski, East Kew (AU)

(73) Assignees: The University of Melbourne, Parkville (AU); Victorian Dairy Industry Authority, Abbotsford (AU)

( * ) Notice: Subject to any disclaimer, the term of this patent is extended or adjusted under 35 U.S.C. 154(b) by 0 days.

(21) Appl. No.: 09/066,330

(22) PCT Filed: Oct. 30, 1996

(86) PCT No.: PCT/AU96/00673

§ 371 (c)(1), (2), (4) Date: Sep. 15, 1998

(87) PCT Pub. No.: WO97/16542

PCT Pub. Date: May 9, 1997

(30) Foreign Application Priority Data

Oct. 30, 1995 (AU) .............................................. PN6275

(51) Int. Cl.[7] ............................................... A61K 39/02

(52) U.S. Cl. ............................... 424/184.1; 424/185.1; 424/190.1; 424/193.1; 424/197.11

(58) Field of Search .......................... 424/184.1, 185.1, 424/190.1, 193.1, 197.11

(56) References Cited

U.S. PATENT DOCUMENTS 5,523,390 A * 6/1996 Travis et al.
5,707,620 A * 1/1998 Travis et al.

FOREIGN PATENT DOCUMENTS

| WO | WO 95/07286 | 3/1995 |
|---|---|---|
| WO | WO 95/11298 | 4/1995 |
| WO | WO 96/17936 | 6/1996 |

OTHER PUBLICATIONS

J. Of Biol. Chem., vol. 270, No. 3, Jan. 20, 1995, N. Pavloff Uet. AIU., "Molecular Cloning & Structural Characterization of the Arg–gingipain Proteinase of Porphyromonas gingivalis", pp. 1007–1010 (in particular, Figure 1B).

Archives of Biochemistry and Biophysics, vol. 316, No. 2, Feb. 1, 1995, K. Okamoto et al., "Structural Characterization of Argingipain, a Novel Arginine–Specific cysteine proteinase as a major peroidontal pathogenic factor from Porphyromonas gingivalis", pp. 917–925 (in particular, Table 1 and Figure 3).

J. of Biol. Chemistry, vol. 269, No. 1, Jan. 7, 1994, R. Pike et al., "Lysine–and Arginine–specific proteinases from Porphyromonas gingivalis", pp. 406–411 (in particular Table II).

J. of Bacteriology, vol. 178, No. 10, May 1996, G.A. Barkocy–Gallagher et al., "Analysis of the prtP gene encoding porphypain, a cysteine proteinase of Porphyromonas gingivalis" pp. 2734–2741 (In particular Fogure 2).

J. Biochem., vol. 120, No. 2, 1996, K. Okamoto et al., Cloning & sequencing of the gene encoding a novel Lysin–specific cysteine proteinase (Lys–Gingipain) in P. Gingivalis: Structural relationship with the Arginine–Specific cysteine proteinase (Arg–Gingipain): pp. 398–406 (In particular, Figure 3).

Infection and Immunity, vol. 63, No. 12, Dec. 1995, J. Aduse–opoku et al., "Characterization, genetic analysis, and Expression of a protease antigen (PrpRI) of P.gingivalis W50" pp. 4744–4754 (In particular, p. 4748).

Biochemical and Biophysical Res. Communications, vol. 224, No. 3, 1996, N. Slakeski et al., "Characterization of a P.gingivalis gene prtR that encodes an arginine–specific thiol proteinase and multiple adhesins" pp. 605–610 (In particular, p. 608).

* cited by examiner

*Primary Examiner*—Gary L. Kunz
*Assistant Examiner*—Stephen Gucker
(74) *Attorney, Agent, or Firm*—Nixon & Vanderhye

(57) ABSTRACT

This invention relates to the PrtR-PrtK cell surface protein of *Porphyromonas gingivalis* in particular a multimeric cell associated protein complex comprising the PrtR and PrtK proteins. There is provided a substantially purified antigenic complex for use in raising an antibody response directed against *Porphyromonas gingivalis.* The complex comprises at least one multimeric protein complex of arginine-specific and lysine-specific thiol endopeptidases each containing at least one adhesin domain. The complex has a molecular weight of greater than about 200 kDa. The invention also relates to pharmaceutical compositions and associated agents based on said complex for the detection, prevention and treatment of Periodontal disease associated with *P. gingivalis.*

9 Claims, 18 Drawing Sheets

Figure 6

PrtR

| | | |
|---|---|---|
| PrtR45 | R↓YTPVEEKQNGRMIVIV | mature Arg- specific thiol protease |
| PrtR44 | R↓SGQAEIVLEAHDVWND | Haemagglutinin, adhesin |
| PrtR15 | R↓ADFTETFESSTHGEAP | adhesin |
| PrtR17 | K↓PQSVWIERTVDLPAGT | adhesin |
| PrtR27 | R↓ANEAKVVLAADNVWGD | adhesin |

```
RBS                                                                                                                     120
GAATTTTGTCTCCCAAGAAGACTTTATAATGCATAAATACAGAAGGGGTACTACACAGTAAAATCATATTCTAATTTCATCAAAATGAAAAACTTGAACAAGTTTGTTTCGATTGCTCTT
                                                                                      M  K  N  L  N  K  F  V  S  I  A  L

                                                                                                                        240
TGCTCTTCCTTATTAGGAGGAATGGCATTTGCGCAGCAGACAGAGTTGGGACGCAATCCGAATGTGAGATTGCTCGAATCCACTCAGCAATCGGTGACAAAGGTTCAGTTCCGTATGGAC
 C  S  S  L  L  G  G  M  A  F  A  Q  Q  T  E  L  G  R  N  P  N  V  R  L  L  E  S  T  Q  Q  S  V  T  K  V  Q  F  R  M  D

                                                                                                                        360
AACCTCAAGTTCACCGAAGTTCAAACCCCTAAGGGAATCGGACAAGTGCCGACCTATACAGAAGGGGTTAATCTTTCTGAAAAAGGGATGCCTACGCTTCCCATTCTATCACGCTCTTTG
 N  L  K  F  T  E  V  Q  T  P  K  G  I  G  Q  V  P  T  Y  T  E  G  V  N  L  S  E  K  G  M  P  T  L  P  I  L  S  R  S  L

                                                                                                                        480
GCGGTTTCAGACACTCGTGAGATGAAGGTAGAGGTTGTTTCCTCAAAGTTCATCGAAAAGAAAAATGTCCTGATTGCACCCTCCAAGGGCATGATTATGCGTAACGAAGATCCGAAAAAG
 A  V  S  D  T  R  E  M  K  V  E  V  V  S  S  K  F  I  E  K  K  N  V  L  I  A  P  S  K  G  M  I  M  R  N  E  D  P  K  K

                                                                                                                        600
ATCCCTTACGTTTATGGAAAGACGTACTCGCAAAACAAATTCTTCCCGGGAGAGATCGCCACGCTTGATGATCCTTTTATCCTTCGTGATGTGCGTGGACAGGTTGTAAACTTTGCGCCT
 I  P  Y  V  Y  G  K  T  Y  S  Q  N  K  F  F  P  G  E  I  A  T  L  D  D  P  F  I  L  R  D  V  R  G  Q  V  V  N  F  A  P

                                                                                                                        720
TTGCAGTATAACCCTGTGACAAAGACGTTGCGCATCTATACGGAAATCACTGTGGCAGTGAGCGAAACTTCGGAACAAGGCAAAAATATTCTGAACAAGAAAGGTACATTTGCCGGCTTT
 L  Q  Y  N  P  V  T  K  T  L  R  I  Y  T  E  I  T  V  A  V  S  E  T  S  E  Q  G  K  N  I  L  N  K  K  G  T  F  A  G  F
                                                                                                                        840
GAAGACACATACAAGCGCATGTTCATGAACTACGAGCCAGGGCGTTACACACCGGTAGAGGAAAAACAAAATGGTCGTATGATCGTCATCGTAGCCAAAAAGTATGAGGGAGATATTAAA
 E  D  T  Y  K  R  M  F  M  N  Y  E  P  G  R  Y  T  P  V  E  E  K  Q  N  G  R  M  I  V  I  V  A  K  K  Y  E  G  D  I  K

                                                                                                                        960
GATTTCGTTGATTGGAAAAACCAACGCGGTCTCCGTACCGAGGTGAAAGTGGCAGAAGATATTGCTTCTCCCGTTACAGCTAATGCTATTCAGCAATTCGTTAAGCAAGAATACGAGAAA
 D  F  V  D  W  K  N  Q  R  G  L  R  T  E  V  K  V  A  E  D  I  A  S  P  V  T  A  N  A  I  Q  Q  F  V  K  Q  E  Y  E  K
                                                                                                                       1080
GAAGGTAATGATTTGACCTATGTTCTTTTGATTGGCGATCACAAAGATATTCCTGCCAAAATTACTCCGGGGATCAAATCCGACCAGGTATATGGACAAATAGTAGGTAATGACCACTAC
 E  G  N  D  L  T  Y  V  L  L  I  G  D  H  K  D  I  P  A  K  I  T  P  G  I  K  S  D  Q  V  Y  G  Q  I  V  G  N  D  H  Y
                                                                                                                       1200
AACGAAGTCTTCATCGGTCGTTTCTCATGTGAGAGCAAAGGGATCTGAAGACACAAATCGATCGGACTATTCACTATGAGCGCAATATAACCACGGAAGACAAATGGCTCGGTCAGGCT
 N  E  V  F  I  G  R  F  S  C  E  S  K  E  D  L  K  T  Q  I  D  R  T  I  H  Y  E  R  N  I  T  T  E  D  K  W  L  G  Q  A
                                                                                                                       1320
CTTTGTATTGCTTCGGCTGAAGGAGGCCCATCCGCAGACAATGGTGAAAGTGATATCCAGCATGAGAATGTAATCGCCAATCTGCTTACCCAGTATGGTTATACCAAGATTATCAAATGT
 L  C  I  A  S  A  E  G  G  P  S  A  D  N  G  E  S  D  I  Q  H  E  N  V  I  A  N  L  L  T  Q  Y  G  Y  T  K  I  I  K  C
                                                                                                                       1440
TATGATCCGGGAGTAACTCCTAAAAACATTATTGATGCTTTCAACGGAGGAATCTCGTTGGCCAACTATACGGGCCACGGTAGCGAAACAGCTTGGGGTACGTCTCACTTCGGCACCACT
 Y  D  P  G  V  T  P  K  N  I  I  D  A  F  N  G  G  I  S  L  A  N  Y  T  G  H  G  S  E  T  A  W  G  T  S  H  F  G  T  T
                                                                                                                       1560
CATGTGAAGCAGCTTACCAACAGCAACCAGCTACCGTTTATTTCGACGTAGCTTGTGTGAATGGCGATTTCCTATTCAGCATGCCTTGTTTCGCAGAAGCATTGATGCGTGCACAAAAA
 H  V  K  Q  L  T  N  S  N  Q  L  P  F  I  F  D  V  A  C  V  N  G  D  F  L  F  S  M  P  C  F  A  E  A  L  M  R  A  Q  K
```

Figure 8b-1

```
                                                                                                                        1680
GATGGTAAGCCGACAGGTACTGTTGCTATCATAGCGTCTACGATCAACCAGTCTTGGGCTTCTCCTATGCGCGGGCAGGATGAGATGAACGAAATTCTGTGCGAAAAACACCCGAACAAC
 D  G  K  P  T  G  T  V  A  I  I  A  S  T  I  N  Q  S  W  A  S  P  M  R  G  Q  D  E  M  N  E  I  L  C  E  K  H  P  N  N
                                                                                                                        1800
ATCAAGCGTACTTTCGGTGGTGTCACCATGAACGGTATGTTTGCTATGGTGGAAAAGTATAAAAAGGATGGTGAGAAGATGCTCGACACATGGACTGTATTCGGCGACCCCTCGCTGCTC
 I  K  R  T  F  G  G  V  T  M  N  G  M  F  A  M  V  E  K  Y  K  K  D  G  E  K  M  L  D  T  W  T  V  F  G  D  P  S  L  L
                                                                                                                        1920
GTTCGTACACTTGTCCCGACCAAAATGCAGGTTACGGCTCCGGCTCAGATTAATTTGACGGATGCTTCAGTCAACGTATCTTGCGATTATAATGGTGCTATTGCTACCATTTCAGCCAAT
 V  R  T  L  V  P  T  K  M  Q  V  T  A  P  A  Q  I  N  L  T  D  A  S  V  N  V  S  C  D  Y  N  G  A  I  A  T  I  S  A  N
                                                                                                                        2040
GGAAAGATGTTCGGTTCTGCAGTTGTCGAAAATGGAACAGCTACAATCAATCTGACAGGTCTGACAAATGAAAGCACGCTTACCCTTACAGTAGTTGGTTACAACAAAGAGACGGTTATT
 G  K  M  F  G  S  A  V  V  E  N  G  T  A  T  I  N  L  T  G  L  T  N  E  S  T  L  T  L  T  V  V  G  Y  N  K  E  T  V  I
                                                                                                                        2160
AAGACCATCAACACTAATGGTGAGCCTAACCCCTACCAGCCTGTTTCCAACTTGACTGCTACAACGCAGGGTCAGAAAGTAACGCTCAAGTGGGATGCACCGAGCACGAAAACCAATGCA
 K  T  I  N  T  N  G  E  P  N  P  Y  Q  P  V  S  N  L  T  A  T  T  Q  G  Q  K  V  T  L  K  W  D  A  P  S  T  K  T  N  A
                                                                                                                        2280
ACCACTAATACCGCTCGCAGCGTGGATGGCATACGAGAACTGGTTCTTCTGTCAGTCAGCGATGCCCCCGAACTTCTTCGCAGCGGTCAGGCCGAGATTGTTCTTGAAGCTCACGATGTT
 T  T  N  T  A  R  S  V  D  G  I  R  E  L  V  L  L  S  V  S  D  A  P  E  L  L  R  S  G  Q  A  E  I  V  L  E  A  H  D  V
                                                                                                                        2400
TGGAATGATGGATCCGGTTATCAGATTCTTTTGGATGCAGACCATGATCAATATGGACAGGTTATACCCAGTGATACCCATACTCTTTGGCCGAACTGTAGTGTCCCGGCCAATCTGTTC
 W  N  D  G  S  G  Y  Q  I  L  L  D  A  D  H  D  Q  Y  G  Q  V  I  P  S  D  T  H  T  L  W  P  N  C  S  V  P  A  N  L  F
                                                                                                                        2520
GCTCCGTTCGAATATACTGTTCCGGAAAATGCAGATCCTTCTTGTTCCCCTACCAATATGATAATGGATGGTACTGCATCCGTTAATATACCGGCCGGAACTTATGACTTTGCAATTGCT
 A  P  F  E  Y  T  V  P  E  N  A  D  P  S  C  S  P  T  N  M  I  M  D  G  T  A  S  V  N  I  P  A  G  T  Y  D  F  A  I  A
                                                                                                                        2640
GCTCCTCAAGCAAATGCAAAGATTTGGATTGCCGGACAAGGACCGACGAAAGAAGATGATTATGTATTTGAAGCCGGTAAAAAATACCATTTCCTTATGAAGAAGATGGGTAGCGGTGAT
 A  P  Q  A  N  A  K  I  W  I  A  G  Q  G  P  T  K  E  D  D  Y  V  F  E  A  G  K  K  Y  H  F  L  M  K  K  M  G  S  G  D
                                                                                                                        2760
GGAACTGAATTGACTATAAGCGAAGGTGGTGGAAGCGATTACACCTATACTGTCTATCGTGACGGCACGAAGATCAAGGAAGGTCTGACGGCTACGACATTCGAAGAAGACGGTGTAGCT
 G  T  E  L  T  I  S  E  G  G  G  S  D  Y  T  Y  T  V  Y  R  D  G  T  K  I  K  E  G  L  T  A  T  T  F  E  E  D  G  V  A
                                                                                                                        2880
ACGGGCAATCATGAGTATTGCGTGGAAGTTAAGTACACAGCCGGCGTATCTCCGAAGGTATGTAAAGACGTTACGGTAGAAGGATCCAATGAATTTGCTCCTGTACAGAACCTGACCGGT
 T  G  N  H  E  Y  C  V  E  V  K  Y  T  A  G  V  S  P  K  V  C  K  D  V  T  V  E  G  S  N  E  F  A  P  V  Q  N  L  T  G
                                                                                                                        3000
AGTGCAGTCGGCCAGAAAGTAACGCTTAAGTGGGATGCACCTAATGGTACCCCGAATCCAAATCCAAATCCGAATCCAAATCCGAATCCCGGAACAACTACACTTTCCGAATCATTCGAA
 S  A  V  G  Q  K  V  T  L  K  W  D  A  P  N  G  T  P  N  P  N  P  N  P  N  P  N  P  N  P  G  T  T  T  L  S  E  S  F  E
                                                                                                                        3120
AATGGTATTCCTGCCTCATGGAAGACGATCGATGCAGACGGTGACGGGCATGGCTGGAAGCCTGGAAATGCTCCCGGAATCGCTGGCTACAATAGCAATGGTTGTGTATATTCAGAGTCA
 N  G  I  P  A  S  W  K  T  I  D  A  D  G  D  G  H  G  W  K  P  G  N  A  P  G  I  A  G  Y  N  S  N  G  C  V  Y  S  E  S
                                                                                                                        3240
TTCGGTCTTGGTGGTATAGGAGTTCTTACCCCTGACAACTATCTGATAACACCGGCATTGGATTTGCCTAACGGAGGTAAGTTGACTTTCTGGGTATGCGCACAGGATGCTAATTATGCA
 F  G  L  G  G  I  G  V  L  T  P  D  N  Y  L  I  T  P  A  L  D  L  P  N  G  G  K  L  T  F  W  V  C  A  Q  D  A  N  Y  A
                                                                                                                        3360
TCCGAGCACTATGCGGTGTATGCATCTTCGACCGGTAACGATGCATCCAACTTCACGAATGCTTTGTTGGAAGAGACGATTACGGCAAAAGGTGTTCGCTCGCCGGAAGCTATGCGTGGT
 S  E  H  Y  A  V  Y  A  S  S  T  G  N  D  A  S  N  F  T  N  A  L  L  E  E  T  I  T  A  K  G  V  R  S  P  E  A  M  R  G
                                                                                                                        3480
CGTATACAGGGTACTTGGCGCCAGAAGACGGTAGACCTTCCCGCAGGTACGAAATATGTTGCTTTCCGTCACTTCCAAAGCACCGATATGTTCTACATCGACCTTGATGAGGTTGAGATC
 R  I  Q  G  T  W  R  Q  K  T  V  D  L  P  A  G  T  K  Y  V  A  F  R  H  F  Q  S  T  D  M  F  Y  I  D  L  D  E  V  E  I
```

Figure 8b-2

```
                                                                                                                    3600
AAGGCCAATGGCAAGCGCGCAGACTTCACGGAAACGTTCGAGTCTTCTACTCATGGAGAGGCACCAGCGGAATGGACTACTATCGATGCCGATGGCGATGGTCAGGGTTGGCTCTGTCTG
 K  A  N  G  K  R  A  D  F  T  E  T  F  E  S  S  T  H  G  E  A  P  A  E  W  T  T  I  D  A  D  G  D  G  Q  G  W  L  C  L
                                                                                                                    3720
TCTTCCGGACAATTGGACTGGCTGACAGCTCATGGCGGCACCAACGTAGTAAGCTCTTTCTCATGGAATGGAATGGCTTTGAATCCTGATAACTATCTCATCTCAAAGGATGTTACAGGC
 S  S  G  Q  L  D  W  L  T  A  H  G  G  T  N  V  V  S  S  F  S  W  N  G  M  A  L  N  P  D  N  Y  L  I  S  K  D  V  T  G
                                                                                                                    3840
GCAACGAAGGTAAAGTACTACTATGCAGTCAACGACGGTTTTCCCGGGGATCACTATGCGGTGATGATCTCCAAGACGGGCACGAACGCCGGAGACTTCACGGTTGTTTTCGAAGAAACG
 A  T  K  V  K  Y  Y  Y  A  V  N  D  G  F  P  G  D  H  Y  A  V  M  I  S  K  T  G  T  N  A  G  D  F  T  V  V  F  E  E  T
                                                                                                                    3960
CCTAACGGAATAAATAAGGGCGGAGCAAGATTCGGTCTTTCCACGGAAGCCGATGGCGCCAAACCTCAAAGTGTATGGATCGAGCGTACGGTAGATTTGCCTGCGGGCACGAAGTATGTT
 P  N  G  I  N  K  G  G  A  R  F  G  L  S  T  E  A  D  G  A  K  P  Q  S  V  W  I  E  R  T  V  D  L  P  A  G  T  K  Y  V
                                                                                                                    4080
GCTTTCCGTCACTACAATTGCTCGGATTTGAACTACATTCTTTTGGATGATATTCAGTTCACCATGGGTGGCAGCCCCACCCCGACCGATTATACCTACACGGTGTATCGTGATGGTACG
 A  F  R  H  Y  N  C  S  D  L  N  Y  I  L  L  D  D  I  Q  F  T  M  G  G  S  P  T  P  T  D  Y  T  Y  T  V  Y  R  D  G  T
                                                                                                                    4200
AAGATCAAGGAAGGTTTGACCGAAACGACCTTCGAAGAAGACGGCGTAGCTACGGGCAATCATGAGTATTGCGTGGAAGTGAAGTACACAGCCGGCGTATCTCCGAAGAAATGTGTAAAC
 K  I  K  E  G  L  T  E  T  T  F  E  E  D  G  V  A  T  G  N  H  E  Y  C  V  E  V  K  Y  T  A  G  V  S  P  K  K  C  V  N
                                                                                                                    4320
GTAACTGTTAATTCGACACAGTTCAATCCTGTAAAGAACCTGAAGGCACAACCGGATGGCGGCGACGTGGTTCTCAAGTGGGAAGCCCCGAGCGCAAAGAAGACAGAAGGTTCTCGTGAA
 V  T  V  N  S  T  Q  F  N  P  V  K  N  L  K  A  Q  P  D  G  G  D  V  V  L  K  W  E  A  P  S  A  K  K  T  E  G  S  R  E
                                                                                                                    4440
GTAAAACGGATCGGAGACGGTCTTTTCGTTACGATCGAACCTGCAAACGATGTACGTGCCAACGAAGCCAAGGTTGTGCTCGCAGCAGACAACGTATGGGGAGACAATACGGGTTACCAG
 V  K  R  I  G  D  G  L  F  V  T  I  E  P  A  N  D  V  R  A  N  E  A  K  V  V  L  A  A  D  N  V  W  G  D  N  T  G  Y  Q
                                                                                                                    4560
TTCTTGTTGGATGCCGATCACAATACATTCGGAAGTGTCATTCCGGCAACCGGTCCTCTCTTTACCGGAACAGCTTCTTCCGATCTTTACAGTGCGAACTTCGAGTCTTTGATCCCGGCC
 F  L  L  D  A  D  H  N  T  F  G  S  V  I  P  A  T  G  P  L  F  T  G  T  A  S  S  D  L  Y  S  A  N  F  E  S  L  I  P  A
                                                                                                                    4680
AATGCCGATCCTGTTGTTACTACACAGAATATTATCGTTACAGGACAGGGTGAAGTTGTAATCCCCGGTGGTGTTTACGACTATTGCATTACGAACCCGGAACCTGCATCCGGAAAGATG
 N  A  D  P  V  V  T  T  Q  N  I  I  V  T  G  Q  G  E  V  V  I  P  G  G  V  Y  D  Y  C  I  T  N  P  E  P  A  S  G  K  M
                                                                                                                    4800
TGGATCGCAGGAGATGGAGGCAACCAGCCTGCACGTTATGACGATTTCACATTCGAAGCAGGCAAGAAGTACACCTTCACGATGCGTCGCGCCGGAATGGGAGATGGAACTGATATGGAA
 W  I  A  G  D  G  G  N  Q  P  A  R  Y  D  D  F  T  F  E  A  G  K  K  Y  T  F  T  M  R  R  A  G  M  G  D  G  T  D  M  E
```

Figure 8b-3

```
                                                                                                                        4920
GTCGAAGACGATTCACCTGCAAGCTATACCTATACAGTCTATCGTGACGGCACGAAGATCAAGGAAGGTCTGACCGAAACGACCTACCGCGACGCAGGAATGAGTGCACAATCTCATGA
 V  E  D  D  S  P  A  S  Y  T  Y  T  V  Y  R  D  G  T  K  I  K  E  G  L  T  E  T  T  Y  R  D  A  G  M  S  A  Q  S  H  E
                                                                                                                        5040
TATTGCGTGGAAGTTAAGTACACAGCCGGTGTTTCTCCGAAGGTTTGTGTGGATTATATTCCTGACGGAGTGGCAGACGTAACGGCTCAGAAGCCTTACACGCTGACAGTTGTAGGAAAG
 Y  C  V  E  V  K  Y  T  A  G  V  S  P  K  V  C  V  D  Y  I  P  D  G  V  A  D  V  T  A  Q  K  P  Y  T  L  T  V  V  G  K
                                                                                                                        5160
ACGATCACGGTAACTTGCCAAGGCGAAGCTATGATCTACGACATGAACGGTCGTCGTCTGGCAGCCGGTCGCAACACGGTTGTTTACACGGCTCAGGGCGGCTACTATGCAGTTATGGTT
 T  I  T  V  T  C  Q  G  E  A  M  I  Y  D  M  N  G  R  R  L  A  A  G  R  N  T  V  V  Y  T  A  Q  G  G  Y  Y  A  V  M  V
                                                                                                                        5280
GTCGTTGACGGCAAGTCTTACGTAGAGAAACTCGCTATCAAGTAAATCTGTCTTGGACTCGGAGACTTTGTGCAGACACTTTTAAGATAGGTCTGTAATTGTCTCAGAGTATGAATCGGT
 V  V  D  G  K  S  Y  V  E  K  L  A  I  K  *
```

Figure 8b-4

*prtK*

PrtK

| | | |
|---|---|---|
| prtK48 | R↓DVYTDHGDLYNTPVRML | mature Lys- specific thiol protease |
| prtK39 | R↓ANEAKVVLAADNVWGD | Haemagglutinin, adhesin |
| prtK15 | R↓ADFTETFESSTHGEAP | adhesin |
| prtK44 | K↓PQSVWIERTVDLPAGT | adhesin |

```
1     GGATCCTACGCCCGATACCCATACTCGAAGCCTTTGCTCAGTACCATCCTGCAGAAGGTTACTCTTTCGCATATAGTGACCCTCTTTTCTCTCAGCATAATGGTACCTATCATATCAGTA 120
121   AGGGGCGTATTGTCTTTTCGAACAATGTACAGCCCGAGAACTCTTTACTTCCACATCACACCCCCGACTCCTTAGTCAAGGATCTTTTTTCCCCTTTCCCCTCCGCTCTCTTCCTCATGC 240
241   TGGACTGACTTAACCTTGGTCTGCTCTACTTTTCGGTTGTAAATACATGCAACACAATAACTTTAAGTGTTGTTAGACAACACTTTTACAAGACTCTGACTTTTAATGAGGTGGAGCATG 360
361   AACCTTTTCCTCTTTCATCTTCTCCTTCAGATTACAGTCAATATTTTGGCAAAAGGCTAATTGACAGCCTTTTATAAGGGTTAATCCCTTGTGGCTTATATTGAAAACATGTTCTTTATA 480
481   ATCCGATACTCTTCTTAAATCGAATTTTTTCTCTAAATTGCGCCGCAACAAAACTCCTTGAGAAAAGTACCAATAGAAATAGAAGGTAGCATTTTGCCTTTAAATTCCTTTTCTTTTCTT 600
601   GGATTGTTCTTGAAATGAATCTTATTTGTGGATTTTTTTTGTTTTTTAACCCGGCCGTGGTTCTCTGAATCACGACCATAAATTGTTTTAAAGTATGAGGAAATTATTATTGCTGATCG 720
                                                                                                                M  R  K  L  L  L  L  I  A
721   CGGCGTCCCTTTTGGGAGTTGGTCTTTACGCCCAAAGCGCCAAGATTAAGCTTGATGCTCCGACTACTCGAACGACATGTACGAACAATAGCTTCAAGCAGTTCGATGCAAGCTTTTCGT 840
       A  S  L  L  G  V  G  L  Y  A  Q  S  A  K  I  K  L  D  A  P  T  T  R  T  T  C  T  N  N  S  F  K  Q  F  D  A  S  F  S  F
841   TCAATGAAGTCGAGCTGACAAAGGTGGAGACCAAAGGTGGTACTTTCGCCTCAGTGTCAATTCCGGGTGCATTCCCGACCGGTGAGGTTGGTTCTCCCGAAGTGCCAGCAGTTAGGAAGT 960
       N  E  V  E  L  T  K  V  E  T  K  G  G  T  F  A  S  V  S  I  P  G  A  F  P  T  G  E  V  G  S  P  E  V  P  A  V  R  K  L
961   TGATTGCTGTGCCTGTCGGAGCCACACCTGTTGTTCGCGTGAAAAGTTTTACCGAGCAAGTTTACTCTCTGAACCAATACGGTTCCGAAAAACTCATGCCACATCAACCCTCTATGAGCA 1080
       I  A  V  P  V  G  A  T  P  V  V  R  V  K  S  F  T  E  Q  V  Y  S  L  N  Q  Y  G  S  E  K  L  M  P  H  Q  P  S  M  S  K
1081  AGAGTGATGATCCCGAAAAGGTTCCCTTCGTTTACAATGCTGCTGCTTATGCACGCAAAGGTTTTGTCGGACAAGAACTGACCCAAGTAGAAATGTTGGGGACAATGCGTGGTGTTCGCA 1200
       S  D  D  P  E  K  V  P  F  V  Y  N  A  A  A  Y  A  R  K  G  F  V  G  Q  E  L  T  Q  V  E  M  L  G  T  M  R  G  V  R  I
1201  TTGCAGCTCTTACCATTAATCCTGTTCAGTATGATGTGGTTGCAAACCAATTGAAGGTTAGAAACAACATCGAAATTGAAGTAAGCTTTCAAGGAGCTGATGAAGTAGCTACACAACGTT 1320
       A  A  L  T  I  N  P  V  Q  Y  D  V  V  A  N  Q  L  K  V  R  N  N  I  E  I  E  V  S  F  Q  G  A  D  E  V  A  T  Q  R  L
1321  TGTATGATGCTTCTTTTAGCCCTTATTTCGAAACAGCTTATAAACAGCTCTTCAATAGAGATGTTTATACAGATCATGGCGACTTGTATAATACGCCGGTTCGTATGCTTGTTGTTGCAG 1440
       Y  D  A  S  F  S  P  Y  F  E  T  A  Y  K  Q  L  F  N  R  D  V  Y  T  D  H  G  D  L  Y  N  T  P  V  R  M  L  V  V  A  G
1441  GTGCAAAATTCAAAGAAGCTCTCAAGCCTTGGCTCACTTGGAAGGCTCAAAAGGGCTTCTATCTGGATGTGCATTACACAGACGAAGCTGAAGTAGGAACGACAAACGCCTCTATCAAGG 1560
       A  K  F  K  E  A  L  K  P  W  L  T  W  K  A  Q  K  G  F  Y  L  D  V  H  Y  T  D  E  A  E  V  G  T  T  N  A  S  I  K  A
1561  CATTTATTCACAAGAAATACAATGATGGATTGGCAGCTAGTGCTGCTCCGGTCTTCTTGGCTTTGGTTGGTGACACTGACGTTATTAGCGGAGAAAAAGGAAAGAAAACAAAAAAAGTTA 1680
       F  I  H  K  K  Y  N  D  G  L  A  A  S  A  A  P  V  F  L  A  L  V  G  D  T  D  V  I  S  G  E  K  G  K  K  T  K  K  V  T
1681  CCGACTTGTATTACAGTGCAGTCGATGGCGACTATTTCCCTGAAATGTATACTTTCCGTATGTCTGCTTCTTCCCCAGAAGAACTGACGAACATCATTGATAAGGTATTGATGTATGAAA 1800
       D  L  Y  Y  S  A  V  D  G  D  Y  F  P  E  M  Y  T  F  R  M  S  A  S  S  P  E  E  L  T  N  I  I  D  K  V  L  M  Y  E  K
1801  AGGCTACTATGCCAGATAAGAGTTATTTGGAGAAAGTTCTCTTGATTGCAGGTGCAGATTATAGCTGGAATTCCCAGGTAGGTCAGCCAACCATTAAATACGGTATGCAGTACTACTACA 1920
       A  T  M  P  D  K  S  Y  L  E  K  V  L  L  I  A  G  A  D  Y  S  W  N  S  Q  V  G  Q  P  T  I  K  Y  G  M  Q  Y  Y  Y  N
1921  ACCAAGAGCATGGTTATACCGACGTGTACAACTATCTCAAAGCCCCTTATACAGGTTGCTACAGTCATTTGAATACCGGAGTCAGCTTTGCAAACTATACAGCGCATGGATCTGAGACCG 2040
       Q  E  H  G  Y  T  D  V  Y  N  Y  L  K  A  P  Y  T  G  C  Y  S  H  L  N  T  G  V  S  F  A  N  Y  T  A  H  G  S  E  T  A
2041  CATGGGCTGATCCACTTCTGACTACTTCTCAACTGAAAGCACTCACTAATAAGGACAAATACTTCTTAGCTATTGGCAACTGCTGTATTACAGCTCAATTCGATTATGTACAGCCTTGCT 2160
       W  A  D  P  L  L  T  T  S  Q  L  K  A  L  T  N  K  D  K  Y  F  L  A  I  G  N  C  C  I  T  A  Q  F  D  Y  V  Q  P  C  F
```

Figure 9b-1

```
2161                                                                                                                            2280
TCGGAGAGGTAATAACTCGCGTTAAGGAGAAAGGGGCTTATGCCTATATCGGTTCATCTCCAAATTCTTATTGGGGCGAGGACTACTATTGGAGTGTGGGTGCTAATGCCGTATTTGGTG
 G  E  V  I  T  R  V  K  E  K  G  A  Y  A  Y  I  G  S  S  P  N  S  Y  W  G  E  D  Y  Y  W  S  V  G  A  N  A  V  F  G  V
2281                                                                                                                            2400
TTCAGCCTACTTTTGAAGGTACGTCTATGGGTTCTTATGATGCTACATTCTTGGAGGATTCGTACAACACAGTGAATTCTATTATGTGGGCAGGTAATCTTGCCGCTACTCATGCTGGAA
 Q  P  T  F  E  G  T  S  M  G  S  Y  D  A  T  F  L  E  D  S  Y  N  T  V  N  S  I  M  W  A  G  N  L  A  A  T  H  A  G  N
2401                                                                                                                            2520
ATATCGGCAATATTACCCATATTGGTGCTCATTACTATTGGGAAGCTTATCATGTCCTTGGCGATGGTTCGGTTATGCCTTATCGTGCAATGCCTAAGACCAATACTTATACGCTTCCTG
 I  G  N  I  T  H  I  G  A  H  Y  Y  W  E  A  Y  H  V  L  G  D  G  S  V  M  P  Y  R  A  M  P  K  T  N  T  Y  T  L  P  A
2521                                                                                                                            2640
CCTCTTTGCCTCAGAATCAGGCTTCTTATAGCATTCAGGCTTCTGCCGGTTCTTACGTAGCTATTTCTAAAGATGGAGTTTTGTATGGAACAGGTGTTGCTAATGCCAGCGGTGTTGCGA
 S  L  P  Q  N  Q  A  S  Y  S  I  Q  A  S  A  G  S  Y  V  A  I  S  K  D  G  V  L  Y  G  T  G  V  A  N  A  S  G  V  A  T
2641                                                                                                                            2760
CTGTGAGTATGACTAAGCAGATTACGGAAAATGGTAATTATGATGTAGTTATCACTCGCTCTAATTATCTTCCTGTGATCAAGCAAATTCAGGTAGGTGAGCCTAGCCCCTACCAGCCCG
 V  S  M  T  K  Q  I  T  E  N  G  N  Y  D  V  V  I  T  R  S  N  Y  L  P  V  I  K  Q  I  Q  V  G  E  P  S  P  Y  Q  P  V
2761                                                                                                                            2880
TTTCCAACTTGACAGCTACAACGCAGGGTCAGAAAGTAACGCTCAAGTGGGAAGCACCGAGCGCAAAGAAGGCAGAAGGTTCCCGTGAAGTAAAACGGATCGGAGACGGTCTTTTCGTTA
 S  N  L  T  A  T  T  Q  G  Q  K  V  T  L  K  W  E  A  P  S  A  K  K  A  E  G  S  R  E  V  K  R  I  G  D  G  L  F  V  T
2881                                                                                                                            3000
CGATCGAACCTGCAAACGATGTACGTGCCAACGAAGCCAAGGTTGTGCTTGCGGCAGACAACGTATGGGGAGACAATACGGGTTACCAGTTCTTGTTGGATGCCGATCACAATACATTCG
 I  E  P  A  N  D  V  R  A  N  E  A  K  V  V  L  A  A  D  N  V  W  G  D  N  T  G  Y  Q  F  L  L  D  A  D  H  N  T  F  G
                          ------------------------------------------------------------------------------------
3001                                                                                                                            3120
GAAGTGTCATTCCGGCAACCGGTCCTCTCTTTACCGGAACAGCTTCTTCCAATCTTTACAGTGCGAACTTCGAGTATTTGGTCCCGGCCAATGCCGATCCTGTTGTTACTACACAGAATA
 S  V  I  P  A  T  G  P  L  F  T  G  T  A  S  S  N  L  Y  S  A  N  F  E  Y  L  V  P  A  N  A  D  P  V  V  T  T  Q  N  I
3121                                                                                                                            3240
TTATCGTTACAGGACAGGGTGAAGTTGTAATCCCCGGTGGTGTTTACGACTATTGCATTACGAACCCGGAACCTGCATCCGGAAAGATGTGGATCGCAGGAGATGGAGGCAACCAGCCTG
 I  V  T  G  Q  G  E  V  V  I  P  G  G  V  Y  D  Y  C  I  T  N  P  E  P  A  S  G  K  M  W  I  A  G  D  G  G  N  Q  P  A
3241                                                                                                                            3360
CACGTTATGACGATTTCACATTCGAAGCAGGCAAGAAGTACACCTTCACGATGCGTCGCGCCGGAATGGGAGATGGAACTGATATGGAAGTCGAAGACGATTCACCTGCAAGCTATACCT
 R  Y  D  D  F  T  F  E  A  G  K  K  Y  T  F  T  M  R  R  A  G  M  G  D  G  T  D  M  E  V  E  D  D  S  P  A  S  Y  T  Y
3361                                                                                                                            3480
ACACGGTGTATCGTGACGGCACGAAGATCAAGGAAGGTCTGACAGCTACGACATTCGAAGAAGACGGTGTAGCTGCAGGCAATCATGAGTATTGCGTGGAAGTTAAGTACACAGCCGGCG
 T  V  Y  R  D  G  T  K  I  K  E  G  L  T  A  T  T  F  E  E  D  G  V  A  A  G  N  H  E  Y  C  V  E  V  K  Y  T  A  G  V
3481                                                                                                                            3600
TATCTCCGAAGGTATGTAAAGACGTTACGGTAGAAGGATCCAATGAATTTGCTCCTGTACAGAACCTGACCGGTAGTTCAGTAGGTCAGAAAGTAACGCTTAAGTGGGATGCACCTAATG
 S  P  K  V  C  K  D  V  T  V  E  G  S  N  E  F  A  P  V  Q  N  L  T  G  S  S  V  G  Q  K  V  T  L  K  W  D  A  P  N  G
3601                                                                                                                            3720
GTACCCCGAATCCGAATCCAAATCCGAATCCGAATCCGGGAACAACACTTTCCGAATCATTCGAAAATGGTATTCCGGCATCTTGGAAGACGATCGATGCAGACGGTGACGGGCATGGCT
 T  P  N  P  N  P  N  P  N  P  N  P  G  T  T  L  S  E  S  F  E  N  G  I  P  A  S  W  K  T  I  D  A  D  G  D  G  H  G  W
3721                                                                                                                            3840
GGAAACCTGGAAATGCTCCCGGAATCGCTGGCTACAATAGCAATGGTTGTGTATATTCAGAGTCATTCGGTCTTGGTGGTATAGGAGTTCTTACCCCTGACAACTATCTGATAACACCGG
 K  P  G  N  A  P  G  I  A  G  Y  N  S  N  G  C  V  Y  S  E  S  F  G  L  G  G  I  G  V  L  T  P  D  N  Y  L  I  T  P  A
3841                                                                                                                            3960
CATTGGATTTGCCTAACGGAGGTAAGTTGACTTTCTGGGTATGCGCACAGGATGCTAATTATGCATCCGAGCACTATGCGGTGTATGCATCTTCGACCGGTAACGATGCATCCAACTTCA
 L  D  L  P  N  G  G  K  L  T  F  W  V  C  A  Q  D  A  N  Y  A  S  E  H  Y  A  V  Y  A  S  S  T  G  N  D  A  S  N  F  T
3961                                                                                                                            4080
CGAATGCTTTGTTGGAAGAGACGATTACGGCAAAAGGTGTTCGCTCGCCGAAAGCTATTCGTGGTCGTATACAGGGTACTTGGCGCCAGAAGACGGTAGACCTTCCCGCAGGTACGAAAT
 N  A  L  L  E  E  T  I  T  A  K  G  V  R  S  P  K  A  I  R  G  R  I  Q  G  T  W  R  Q  K  T  V  D  L  P  A  G  T  K  Y
4081                                                                                                                            4200
```

Figure 9b-2

```
4201 ATGTTGCTTTCCGTCACTTCCAAAGCACGGATATGTTCTACATCGACCTTGATGAGGTTGAGATCAAGGCCAATGGCAAGCGCGCAGACTTCACGGAAACGTTCGAGTCTTCTACTCATG 4320
      V  A  F  R  H  F  Q  S  T  D  M  F  Y  I  D  L  D  E  V  E  I  K  A  N  G  K  R  A  D  F  T  E  T  F  E  S  S  T  H  G
4321 GAGAGGCACCAGCGGAATGGACTACTATCGATGCCGATGGCGATGGTCAGGGTTGGCTCTGTCTGTCTTCCGGACAATTGGACTGGCTGACAGCTCATGGCGGCAGCAACGTAGTAAGCT 4440
      E  A  P  A  E  W  T  T  I  D  A  D  G  D  G  Q  G  W  L  C  L  S  S  G  Q  L  D  W  L  T  A  H  G  G  S  N  V  V  S  S
4441 CTTTCTCATGGAATGGAATGGCTTTGAATCCTGATAACTATCTCATCTCAAAGGATGTTACAGGCGCAACGAAGGTAAAGTACTACTATGCAGTCAACGACGGTTTTCCCGGGGATCACT 4560
      F  S  W  N  G  M  A  L  N  P  D  N  Y  L  I  S  K  D  V  T  G  A  T  K  V  K  Y  Y  Y  A  V  N  D  G  F  P  G  D  H  Y
4561 ATGCGGTGATGATCTCCAAGACGGGCACGAACGCCGGAGACTTCACGGTTGTTTTCGAAGAAACGCCTAACGGAATAAATAAGGGCGGAGCAAGATTCGGTCTTTCCACGGAAGCCAATG 4680
      A  V  M  I  S  K  T  G  T  N  A  G  D  F  T  V  V  F  E  E  T  P  N  G  I  N  K  G  G  A  R  F  G  L  S  T  E  A  N  G
4681 GCGCCAAACCTCAAAGTGTATGGATCGAGCGTACGGTAGATTTGCCTGCAGGCACGAAGTATGTTGCTTTCCGTCACTACAATTGCTCGGATTTGAACTACATTCTTTTGGATGATATTC 4800
      A  K  P  Q  S  V  W  I  E  R  T  V  D  L  P  A  G  T  K  Y  V  A  F  R  H  Y  N  C  S  D  L  N  Y  I  L  L  D  D  I  Q
4801 AGTTCACCATGGGTGGCAGCCCCACCCCGACCGATTATACCTACACGGTGTATCGTGATGGTACGAAGATCAAGGAAGGTTTGACCGAAACGACCTTCGAAGAAGACGGCGTAGCTACGG 4920
      F  T  M  G  G  S  P  T  P  T  D  Y  T  Y  T  V  Y  R  D  G  T  K  I  K  E  G  L  T  E  T  T  F  E  E  D  G  V  A  T  G
4921 GCAATCATGAGTATTGCGTGGAAGTGAAGTACACAGCCGGCGTATCTCCGAAGAAATGTGTAGACGTAACTGTTAATTCGACACAGTTCAATCCTGTACAGAACCTGACGGCAGAACAAG 5040
      N  H  E  Y  C  V  E  V  K  Y  T  A  G  V  S  P  K  K  C  V  D  V  T  V  N  S  T  Q  F  N  P  V  Q  N  L  T  A  E  Q  A
5041 CTCCTAACAGCATGGATGCAATCCTTAAATGGAATGCACCGGCATCTAAGCGTGCGGAAGTTCTGAACGAAGACTTCGAAAATGGTATTCCTGCCTCATGGAAGACGATCGATGCAGACG 5160
      P  N  S  M  D  A  I  L  K  W  N  A  P  A  S  K  R  A  E  V  L  N  E  D  F  E  N  G  I  P  A  S  W  K  T  I  D  A  D  G
5161 GTGACGGCAACAATTGGACGACGACCCCTCCTCCCGGAGGCTCCTCTTTTGCAGGTCACAACAGTGCGATCTGTGTCTCTTCAGCTTCTCATATCAACTTTGAAGGTCCTCAGAACCCTG 5280
      D  G  N  N  W  T  T  T  P  P  P  G  G  S  S  F  A  G  H  N  S  A  I  C  V  S  S  A  S  H  I  N  F  E  G  P  Q  N  P  D
5281 ATAACTATCTGGTTACACCGGAGCTTTCTCTTCCTGGCGGAGGAACGCTTACTTTCTGGGTATGTGCACAAGATGCCAATTATGCATCAGAGCACTATGCCGTGTACGCATCTTCTACGG 5400
      N  Y  L  V  T  P  E  L  S  L  P  G  G  G  T  L  T  F  W  V  C  A  Q  D  A  N  Y  A  S  E  H  Y  A  V  Y  A  S  S  T  G
5401 GTAACGACGCTTCCAACTTCGCCAACGCTTTGTTGGAAGAAGTGCTGACGGCCAAGACAGTTGTTACGGCACCTGAAGCCATTCGTGGTACTCGTGCTCAGGGCACCTGGTATCAAAAGA 5520
      N  D  A  S  N  F  A  N  A  L  L  E  E  V  L  T  A  K  T  V  V  T  A  P  E  A  I  R  G  T  R  A  Q  G  T  W  Y  Q  K  T
5521 CGGTACAGTTGCCTGCGGGTACTAAGTATGTTGCCTTCCGTCACTTCGGCTGTACGGACTTCTTCTGGATCAACCTTGATGATGTTGTAATCACTTCAGGGAACGCTCCGTCTTACACCT 5640
      V  Q  L  P  A  G  T  K  Y  V  A  F  R  H  F  G  C  T  D  F  F  W  I  N  L  D  D  V  V  I  T  S  G  N  A  P  S  Y  T  Y
5641 ATACGATCTATCGTAATAATACACAGATAGCATCAGGCGTAACGGAGACTACTTACCGAGATCCGGACTTGGCTACCGGTTTTTACACGTACGGTGTAAAGGTTGTTTACCCGAACGGAG 5760
      T  I  Y  R  N  N  T  Q  I  A  S  G  V  T  E  T  T  Y  R  D  P  D  L  A  T  G  F  Y  T  Y  G  V  K  V  V  Y  P  N  G  E
5761 AATCAGCTATCGAAACTGCTACGTTGAATATCACTTCGTTGGCAGACGTAACGGCTCAGAAGCCTTACACGCTGACAGTTGTAGGAAAGACGATCACGGTAACTTGCCAAGGCGAAGCTA 5880
      S  A  I  E  T  A  T  L  N  I  T  S  L  A  D  V  T  A  Q  K  P  Y  T  L  T  V  V  G  K  T  I  T  V  T  C  Q  G  E  A  M
5881 TGATCTACGACATGAACGGTCGTCGTCTGGCAGCGGGTCGCAACACGGTTGTTTACACGGCTCAGGGCGGCCACTATGCAGTCATGGTTGTCGTTGACGGCAAGTCTTACGTAGAGAAAC 6000
      I  Y  D  M  N  G  R  R  L  A  A  G  R  N  T  V  V  Y  T  A  Q  G  G  H  Y  A  V  M  V  V  V  D  G  K  S  Y  V  E  K  L
     TCGCTGTAAAGTAAATCTGTCTTGGACTCGGAGACTTTGTGCAGACACTTTTAAGATAGGTCTGTAATTGTCTCAGAGTATGAATCGGTCGCCCGACTTCCTTAAAAGGAGGTCGGGCGA
      A  V  K  *
```

Figure 9b-3

DIAGNOSTICS AND TREATMENTS OF PERIODONTAL DISEASE

FIELD OF THE INVENTION

This invention relates to the PrtR-PrtK cell surface protein of *Porphyromonas gingivalis* and in particular a multimeric cell associated protein complex comprising the PrtR and PrtK proteins. The invention also relates to pharmaceutical compositions and associated agents based on said complex for the detection, prevention and treatment of Periodontal disease associated with *P. gingivalis.*

BACKGROUND OF THE INVENTION

Periodontal diseases are bacterial-associated inflammatory diseases of the supporting tissues of the teeth and range from the relatively mild form of gingivitis, the non-specific, reversible inflammation of gingival tissue to the more aggressive forms of periodontitis which are characterised by the destruction of the tooth's supporting structures. Periodontitis is associated with a subgingival infection of a consortium of specific Gram-negative bacteria that leads to the destruction of the periodontium and is a major public health problem. One bacterium that has attracted considerable interest is *P. gingivalis* as the recovery of this microorganism from adult periodontitis lesions can be up to 50% of the subgingival anaerobically cultivable flora, whereas *P. gingivalis* is rarely recovered, and then in low numbers, from healthy sites. A proportional increase in the level of *P. gingivalis* in subgingival plaque has been associated with an increased severity of periodontitis and eradication of the microorganism from the cultivable subgingival microbial population is accompanied by resolution of the disease. The progression of periodontitis lesions in non-human primates has been demonstrated with the subgingival implantation of *P. gingivalis.* These findings in both animals and humans suggest a major role for *P. gingivalis* in the development of adult periodontitis.

*P. gingivalis* is a black-pigmented, anaerobic, asaccharolytic, proteolytic Gram-negative rod that obtains energy from the metabolism of specific amino acids. The microorganism has an absolute growth requirement for iron, preferentially in the form of haeme or its Fe(III) oxidation product haemin and when grown under conditions of excess haemin is highly virulent in experimental animals. A number of virulence factors have been implicated in the pathogenicity of *P. gingivalis* including the capsule, adhesins, cytotoxins and extracellular hydrolytic enzymes. In particular, proteases have received a great deal of attention for their ability to degrade a broad range of host proteins including structural proteins and others involved in defence. The proteins that have been shown to be substrates for *P. gingivalis* proteolytic activity include collagen types I and IV, fibronectin, fibrinogen, laminin, complement and plasma clotting cascade proteins, $\alpha_1$-antitrypsin, $\alpha_2$-macroglobulin, antichymotrypsin, antithrombin III, antiplasmin, cystatin C, IgG and IgA. The major proteolytic activities associated with this organism have been defined by substrate specificity and are "trypsin-like", that is cleavage on the carboxyl side of arginyl and lysyl residues and collagenolytic although other minor activities have been reported.

*P. gingivalis* trypsin-like proteolytic activity has been shown to degrade complement, generating biologically active C5a, impair the phagocytic and other functions of neutrophils by modifying surface receptors, and abrogate the clotting potential of fibrinogen prolonging plasma clotting time. The trypsin-like proteolytic activity of *P. gingivalis* also generates Fc fragments from human IgG1 stimulating the release of pro-inflammatory cytokines from mononuclear cells and is associated with vascular disruption and enhanced vascular permeation through the activation of the kallikrein-kinin cascade. *P. gingivalis* spontaneous mutants with reduced trypsin-like activity as well as wild-type cells treated with the trypsin-like protease inhibitor N-p-tosyl-L-lysine chloromethyl ketone are avirulent in animal models. Further, it has been shown that *P. gingivalis* grown under controlled, haemin-excess conditions expressed more trypsin-like and less collagenolytic activity and were more virulent in mice relative to cells grown under haemin-limited but otherwise identical conditions. The increased expression of the trypsin-like activity by the more virulent *P. gingivalis* has led to the speculation that the trypsin-like proteolytic activity may be the major determinant for infection or disease. However, the cell-associated trypsin-like proteolytic activities of *P. gingivalis* have not been characterised to date.

There has been considerable endeavour to purify and characterise the trypsin-like proteases of *P. gingivalis* from cell-free culture fluids. Chen et al, (1992) [J Biol Chem 267:18896–18901] have purified and characterised a 50 kDa arginine-specific, thiol protease from the culture fluid of *P. gingivalis* H66 designated Arg-gingipain. A similar arginine-specific thiol protease has been disclosed in JP 07135973 and the amino acid sequence disclosed in WO 9507286 and in Kirszbaum et al, 1995 [Biochem Biophys Res Comm 207:424–431]. Pike et al (1994) [J Biol Chem 269:406–411] have characterised a 60 kDa lysine-specific cysteine proteinase from the culture fluid of *P. gingivalis* H66 designated Lys-gingipain and the partial gene sequence for this enzyme was disclosed in WO 9511298 and fully disclosed in WO 9617936. However, prior to the development of the present invention it was unknown that there existed on the cell surface of *P. gingivalis a* 300 kda complex of arginine-specific and lysine-specific proteases both containing adhesin domains. The 300 kDa complex has been designated the PrtR-PrtK complex. The presence of the PrtR-PrtK cell surface complex exhibiting both arginine- and lysine-specific proteolytic activity together with adhesin activity was previously unknown. Furthermore, the new PrtR-PrtK complex of the present invention is expressed on the cell surface, is a major virulence-associated factor and contains unique epitopes not displayed on the individual domains. The previously disclosed arginine-specific and lysine-specific thiol proteases, as discussed, do not exhibit any of these features and have proven of limited application to date. However, the aforementioned features have rendered the PrtR-PrtK complex of the invention ideal for development of diagnostic and immunoprophylactic products. The PrtR-PrtK cell surface complex is accordingly of particular interest for diagnostics and neutralisation by passive immunity through oral compositions containing neutralising antibodies and by vaccine development. In particular for the development of an intra-oral recombinant bacterial vaccine, where the recombinant bacterium expressing an inactivated PrtR-PrtK is a genetically engineered commensal inhabitant of the oral cavity.

SUMMARY OF THE INVENTION

Accordingly in a first aspect the present invention consists in a substantially purified antigenic complex for use in raising an antibody response directed against *Porphyromonas gingivalis,* the complex comprising at least one multimeric protein complex of arginine-specific and lysine-specific thiol endopeptidases each containing at least one adhesin domain, the complex having a molecular weight of greater than about 200 kDa.

In the context of this disclosure, the terms "adhesin" and "hemagglutinin" may be considered to be synonymous.

In a preferred form of the present invention the multimeric protein complex is associated with virulent strains of *Porphyromonas gingivalis,* preferably has a molecular weight of about 294 to about 323 kDa and is preferably derived from *P. gingivalis* W50.

It is also preferred that the multimeric protein complex is composed of 9 proteins. These 9 proteins preferably have the following N-terminal sequences:

DVYTDHGDLYNTPVRML (SEQ ID NO: 1)

YTPVEEKQNGRMIVIVAKKYEGD (SEQ ID NO: 2)

SGQAEIVLEAHDVWNDGSGYQILLDADHDQYGQVIPSDTHFL (SEQ ID NO: 3)

PQSVWIERTVDLPAGTKYVAFR (SEQ ID NO: 4)

ANEAKVVLAADNVWGDNTGYQFLLDA (SEQ ID NO: 5)

ANEAKVVLAADNVWGDNTGYQFLLDA (SEQ ID NO: 5)

PQSVWIERTVDLPAGTKYVAFR (SEQ ID NO: 4)

ADFTETFESSTHGEAPAEWTTIDA (SEQ ID NO: 6)

ADFTETFESSTHGEAPAEWTTIDA. (SEQ ID NO: 6)

It is presently preferred that the 9 proteins are PrtK48, PrtR45, PrtR44, PrtK39, PrtK44, PrtR27, PrtR17, PrtK15 and PrtR15 as described herein.

As the purified antigenic complex normally has enzymatic activity it is preferred in a number of uses the thiol endopeptidases are rendered inactive. This may be achieved in a number of ways, for example by oxidation or by mutation. It is presently preferred that the inactivation is by oxidation.

In yet another preferred embodiment of the present invention the multimeric protein complex is encoded by the DNA sequence shown in FIGS. 8B and 9B.

In a second aspect the present invention consists in a composition for use in eliciting an immune response directed against *Porphyromonas gingivalis,* the composition comprising an effective amount of the complex of the first aspect of the present invention and a suitable adjuvant and/or acceptable carrier.

In a third aspect the present invention consists in an antibody preparation comprising antibodies specifically directed against the complex of the first aspect of the present invention. The antibodies may be polyclonal antibodies or monoclonal antibodies.

In a fourth aspect the present invention consists in a method of treating a subject suffering from *Porphyromonas gingivalis* infection, the method comprising administering to the subject an amount of the antibody preparation of the third aspect of the present invention effective to at least partially neutralize the PrtR-PrtK complex of *Porphyromonas gingivalis.*

As will be recognised by those skilled in the art the antibody preparation may be administered by any of a number of well known routes, however, it is presently preferred that the preparation is administered orally.

In a fifth aspect the present invention consists in a method of reducing the prospect of *P. gingivalis* infection in an individual and/or severity of disease, the method comprising administering to the individual an amount of the composition of the second aspect of the present invention effective to induce an immune response in the individual directed against *P. gingivalis.*

In yet a further aspect the present invention consists in a recombinant host cell, the host cell being transformed with a DNA sequence(s) encoding PrtR-PrtK operatively linked to control sequences such that under appropriate conditions the host cell expresses PrtR-PrtK.

In another aspect, the present invention is directed to novel DNA sequences involving PrtR-PrtK constructs and vectors including plasmid DNA, and viral DNA such as human viruses, animal viruses, insect viruses, or bacteriophages which can be used to direct the expression of PrtR-PrtK protein in appropriate host cells from which the expressed protein may be purified. Another aspect of the present invention provides methods for molecular cloning of the genes encoding the PrtR-PrtK complex. The nucleic acid sequences of the present invention can be used in molecular diagnostic assays for *P. gingivalis* genetic material through nucleic acid hybridization, and including the synthesis of PrtR-PrtK sequence-specific oligonucleotides for use as primers and/or probes in amplifying, and detecting amplified, nucleic acids. Additionally, PrtR-PrtK complex can be used as an immunogen in prophylactic and/or therapeutic vaccine formulations against pathogenic strains of *P. gingivalis,* whether the immunogen is chemically synthesized, purified from *P. gingivalis,* or purified from a recombinant expression vector system. Alternatively, the genes encoding PrtR-PrtK may be incorporated into a bacterial or viral vaccine comprising recombinant bacteria or virus which is engineered to produce PrtR-PrtK by itself, or in combination with immunogenic epitopes of other pathogenic microorganisms. In addition, the genes encoding PrtR-PrtK operatively linked to one or more regulatory elements, can be introduced directly into humans to express the PrtR-PrtK to elicit a protective immune response. A vaccine can also be based upon a recombinant component of a mutated PrtR-PrtK incorporated into an appropriate vector and expressed in a suitable transformed host (eg. *E. coli, Bacillus subtilis, Saccharomyces cerevisiae,* COS cells, CHO cells and HeLa cells) containing the vector. The vaccine can be based on an intra-oral recombinant bacterial vaccine, where the recombinant bacterium expressing an inactivated PrtR-PrtK is a commensal inhabitant of the oral cavity. Unlike whole *P. gingivalis* cells or other previously prepared antigens based on fimbriae or the capsule the PrtR-PrtK complex of the invention or component parts thereof are safe and effective antigens for the preparation of a vaccine for the prevention of *P. gingivalis*-associated periodontal disease. The invention therefore provides a range of recombinant products based on the PrtR-PrtK complex.

The invention also provides antibodies raised against the said PrtR-PrtK complex, herein called anti-PrtR-PrtK antibodies. The antibodies may be blended into oral compositions such as toothpaste, mouthwash, toothpowders and liquid dentifrices, mouthwashes, troches, chewing gums, dental pastes, gingival massage creams, gargle tablets, dairy products and other foodstuffs.

In another aspect the invention provides a method of diagnosis for the presence of *P. gingivalis* characterised by the use of any one or a combination of an antibody, antigen or nucleic acid probe as hereinbefore defined comprising the application of known techniques including for example, enzyme linked immunosorbent assay.

The invention also provides diagnostic kits comprising antibodies, antigens and/or nucleic acid probes as hereinbefore defined.

BRIEF DESCRIPTION OF FIGURES

FIG. 6. SDS-PAGE (boiled/reduced conditions) of 200 mM lysine eluant from the Arg-sepharose FPLC. Lane 1, Pharmacia molecular mass standards (M, shown in kDa). Lane 2, 200 mM lysine eluant from Arg-sepharose FPLC. Silver stained gel.

FIG. 8*b*-1–8*b*-4. Nucleotide sequence of prtR (SEQ ID NO: 7).

FIG. 9*b*-1–9*b*-3. Nucleotide sequence of prtK (SEQ ID NO: 8).

DETAILED DESCRIPTION OF THE INVENTION

Figure 1:
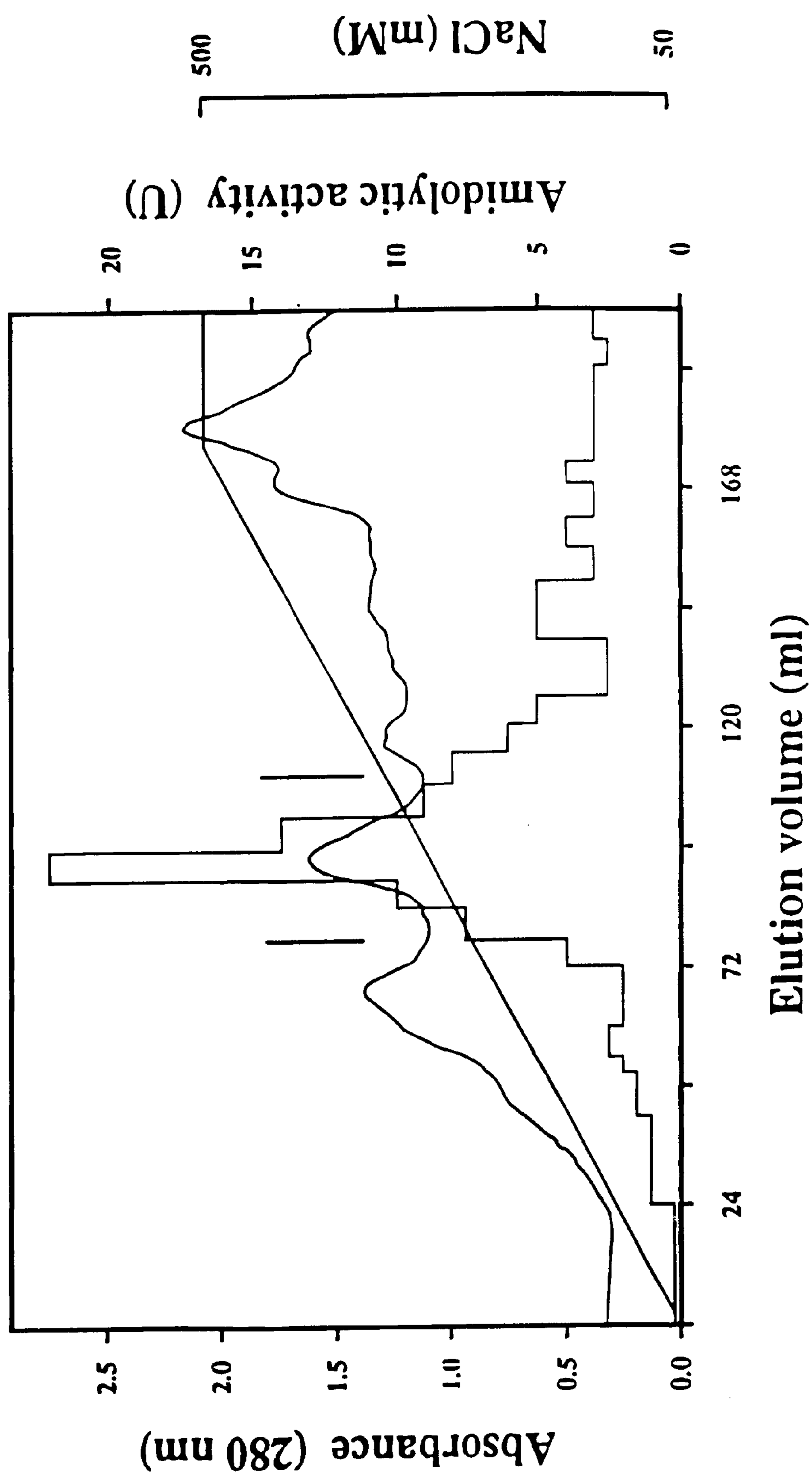
FIG. 1. Anion exchange FPLC of a *P. gingivalis* W50 sonicate. The sonicate in TC buffer containing 50 mM NaCl was applied to a Hiload XK 16/10 Q sepharose column and eluted using a linear gradient from 0–100% buffer B over 90 min at a flow rate of 2.0 ml $min^{-1}$. Fractions (6 ml) were assayed for proteolytic and amidolytic activity using azocasein, Bz-L-Arg-pNA and Z-L-Lys-pNA. The amidolytic activity of each 6 ml fraction with Bz-L-Arg-pNA is shown by the histogram.

The invention will now be described in greater detail by reference to the methods used and applied in the development of the invention and by reference to particular examples which provide the best methods known of performing the invention.

The intra-oral bacterium *Porphyromonas gingivalis* possesses on its cell surface major trypsin-like proteinases as a 294–323 kDa heterodimeric protein complex of Arg-specific and Lys-specific thiol endopeptidases with hemagglutinins (adhesins) herein designated the PrtR-PrtK complex. The PrtR-PrtK complex can be purified from *P. gingivalis* cells by ultrasonication or chloroform extraction followed by diafiltration or anion exchange and Lys-sepharose or Arg-sepharose chromatography. The purified PrtR-PrtK complex is then used to generate antibodies using standard techniques. The animals used for antibody generation can be rabbits, goats, chickens, sheep, horses, cows etc. When a high antibody titre against the PrtR-PrtK complex is detected by immunoassay the animals are bled or eggs or milk are collected and the serum prepared and/or antibody purified using standard techniques or monoclonal antibodies produced by fusing spleen cells with myeloma cells using standard techniques. The antibody (immunoglobulin fraction) may be separated from the culture or ascites fluid, serum, milk or egg by salting out, gel filtration, ion exchange and/or affinity chromatography, and the like, with salting out being preferred. In the salting out method the antiserum or the milk is saturated with ammonium sulphate to produce a precipitate, followed by dialyzing the precipitate against physiological saline to obtain the purified immunoglobulin fraction with the specific anti-(PrtR-PrtK). The preferred antibody is obtained from the equine antiserum and the bovine antiserum and milk. In this invention the antibody contained in the antiserum and milk obtained by immunising the animal with the inactivated PrtR-PrtK may be blended into the oral composition. In this case the antiserum and milk as well as the antibody separated and purified from the antiserum and milk may be used. Each of these materials may be used alone or in combination of two or more. Antibodies against the PrtR-PrtK can be used in oral compositions such as toothpaste and mouthwash to neutralise the PrtR-PrtK and thus prevent disease. The anti-(PrtR-PrtK) antibodies can also be used for the early detection of *P. gingivalis* in subgingival plaque samples by a chairside Enzyme Linked Immunosorbent Assay (ELISA).

For oral compositions it is preferred that the amount of the above antibodies administered is 0.0001–50 g/kg/day and that the content of the above antibodies is 0.0002–10% by weight preferably 0.002–5% by weight of the composition. The oral composition of this invention which contains the above-mentioned serum or milk antibody may be prepared and used in various forms applicable to the mouth such as dentifrice including toothpastes, toothpowders and liquid dentifrices, mouthwashes, troches, periodontal pocket irrigating devices, chewing gums, dental pastes, gingival massage creams, gargle tablets, dairy products and other foodstuffs. The oral composition according to this invention may further include additional well known ingredients depending on the type and form of a particular oral composition.

In certain highly preferred forms of the invention the oral composition may be substantially liquid in character, such as a mouthwash or rinse. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

The pH of such liquid and other preparations of the invention is generally in the range of from about 4.5 to about 9 and typically from about 5.5 to 8. The pH is preferably in the range of from about 6 to about 8.0, preferably 7.4. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc).

Other desirable forms of this invention, the oral composition may be substantially solid or pasty in character, such as toothpowder, a dental tablet or a dentifrice, that is a toothpaste (dental cream) or gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sized of up to about 5 microns, a mean particle size of up to about 1.1 microns, and a surface area of up to about 50,000 $cm^2$/gm., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal alumino-silicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner as illustrated by Thorpe's Dictionary of Applied Chemistry, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in amount of about 10–30% by weight. Other polishing materials are typically present in amount of about 30–75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5–30% w/w of water, 0 to about 70% w/w of glycerine and about 20–80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations are to be sold or otherwise distributed in suitable labelled packages. Thus, ajar of mouthrinse will have a label describing it, in substance, as a mouthrinse or mouthwash and having directions for its use; and a toothpaste, cream or gel will usually be in a collapsible tube, typically aluminium, lined lead or plastic, or other squeeze, pump or pressurised dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, nonionic or ampholytic in nature which does not denature the antibody of the invention, and it is preferred to employ as the surface-active agent a detersive material which imparts to the composition detersive and foaming properties while not denaturing the antibody. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble nonionic surfactants suitable for use with antibodies are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Surface active agent is typically present in amount of about 0.1–5% by weight. It is noteworthy, that the surface active agent may assist in the dissolving of the antibody of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

In the preferred practice of this invention an oral composition according to this invention such as mouthwash or dentifrice containing the composition of the present invention is preferably applied regularly to the gums and teeth, such as every day or every second or third day or preferably from 1 to 3 times daily, at a pH of about 4.5 to about 9, generally about 5.5 to about 8, preferably about 6 to 8, for at least 2 weeks up to 8 weeks or more up to a lifetime.

The compositions of this invention can be incorporated in lozenges, or in chewing gum or other products, e.g. by stirring into a warm gum base or coating the outer surface of a gum base, illustrative of which may be mentioned jelutong, rubber latex, vinylite resins, etc., desirably with conventional plasticisers or softeners, sugar or other sweeteners or such as glucose, sorbitol and the like.

The composition of this invention also includes targeted delivery vehicles such as periodontal pocket irrigation devices, collagen, elastin, or synthetic sponges, membranes or fibres placed in the periodontal pocket or used as a barrier membrane or applied directly to the tooth root.

Another important form of the invention is a composition for use in eliciting an immune response directed against *Porphyromonas gingivalis* based on the PrtR-PrtK complex and suitable adjuvant delivered by nasal spray, orally or by injection to produce a specific immune response against the PrtR-PrtK complex thereby reducing colonisation of *P. gingivalis* and neutralising the PrtR-PrtK thereby preventing disease. Due to the potent enzymatic activity of the complex typically the complex will be inactivated. A vaccine can also be based upon a recombinant component of the PrtR-PrtK incorporated into an appropriate vector and expressed in a suitable transformed host (eg. *E. coli, Bacillus subtilis, Saccharomyces cerevisiae,* COS cells, CHO cells and HeLa cells) containing the vector. Unlike whole *P. gingivalis* cells or other previously prepared antigens based on fimbriae or the capsule the PrtR-PrtK complex is a safe and effective antigens for the preparation of a composition for use in the prevention of *P. gingivalis*-associated periodontal disease. The PrtR-PrtK complex can be produced using recombinant DNA methods as illustrated herein, or can be synthesized chemically from the amino acid sequence disclosed in the present invention. Additionally, according to the present invention, the PrtR-PrtK complex may be used to generate antisera useful for passive immunization against periodontal disease and infections caused by *P. gingivalis.*

Various adjuvants are used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freund's adjuvant (IFA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs and ISCOM matrix. An extensive but not exhaustive list of other examples of adjuvants are listed in Cox and Coulter 1992 [In: Wong W K (ed.) Animals parasite control utilising technology. Bocca Raton; CRC press, 1992; 49–112]. In addition to the adjuvant the vaccine may include conventional pharmaceutically acceptable carriers, excipients, fillers, buffers or diluents as appropriate. One or more doses of the vaccine containing adjuvant may be administered prophylactically to prevent periodontitis or therapeutically to treat already present periodontitis.

In another preferred composition the preparation is combined with a mucosal adjuvant and administered via the oral route. Examples of mucosal adjuvants are cholera toxin and heat labile *E. coli* toxin, the non-toxic B subunits of these toxins, genetic mutants of these toxins which have a reduced toxicity. Other methods which may be utilised to deliver the PrtR-PrtK complex orally include incorporation of the protease into particles of biodegradable polymers (such as acrylates or polyesters) by microencapsulation to aid uptake of the microspheres from the gastrointestinal tract and to protect degradation of the proteins. Liposomes, ISCOMs, hydrogels are examples of other potential methods which may be further enhanced by the incorporation of targeting molecules such as LTB, CTB or lectins for delivery of the PrtR-PrtK complex to the mucosal immune system. In addition to the vaccine and the mucosal adjuvant or delivery system the vaccine may include conventional pharmaceutically acceptable carriers, excipients, fillers, coatings, dispersion media, antibacterial and antifungal agents, buffers or diluents as appropriate.

Another mode of this embodiment provides for either a live recombinant viral vaccine, recombinant bacterial vaccine, recombinant attenuated bacterial vaccine, or an inactivated recombinant viral vaccine which is used to protect against infections caused by *P. gingivalis.* Vaccinia virus is the best known example, in the art, of an infectious virus that is engineered to express vaccine antigens derived from other organisms. The recombinant live vaccinia virus, which is attenuated or otherwise treated so that it does not cause disease by itself is used to immunize the host. Subsequent replication of the recombinant virus within the host provides a continual stimulation of the immune system with the vaccine antigens such as PrtR-PrtK complex, thereby providing long lasting immunity.

Other live vaccine vectors include: adenovirus, cytomegalovirus, and preferably the poxviruses such as vaccinia (Paoletti and Panicali, U.S. Pat. No. 4,603,112) and attenuated Salmonella strains (Stocker et al., U.S. Pat. Nos. 5,210,035; 4,837,151; and 4,735,801; and Curtiss et al., 1988, Vaccine 6:155–160). Live vaccines are particularly advantageous because they continually stimulate the immune system which can confer substantially long-lasting immunity. When the immune response is protective against subsequent *P. gingivalis* infection, the live vaccine itself may be used in a preventive vaccine against *P. gingivalis.* In particular, the live vaccine can be based on a bacterium that is a commensal inhabitant of the oral cavity. This bacterium can be transformed with a vector carrying a recombinant inactivated PrtR-PrtK and then used to colonise the oral cavity, in particular the oral mucosa. Once colonised the oral mucosa, the expression of the recombinant protein will stimulate the mucosal associated lymphoid tissue to produce neutralising antibodies. For example, using molecular biological techniques the genes encoding the PrtR-PrtK may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except that the recombinant virus is inactivated, such as by chemical means known in the art, prior to use as an immunogen and without substantially affecting the immunogenicity of the expressed immunogen.

In another variation of this embodiment, genetic material is used directly as the vaccine formulation. Nucleic acid (DNA or RNA) containing sequences encoding the PrtR-PrtK protein complex operatively linked to one or more regulatory elements can be introduced directly to vaccinate the individual ("direct gene transfer") against pathogenic strains of *P. gingivalis.* Direct gene transfer into a vaccinated individual, resulting in expression of the genetic material by the vaccinated individual's cells such as vascular endothelial cells as well as the tissue of the major organs, has been demonstrated by techniques in the art such as by injecting intravenously an expression plasmid:cationic liposome complex (Zhu et al., 1993, Science 261:209–211). Other effective methods for delivering vector DNA into a target cell are known in the art. In one example, purified recombinant plasmid DNA containing viral genes has been used to inoculate (whether parentally, mucosally, or via gene-gun immunization) vaccines to induce a protective immune response (Fynan et al. 1993, Proc. Natl. Acad. Sci. USA 90:11478–11482). In another example, cells removed from an individual can be transfected or electroporated by standard procedures known in the art, resulting in the introduction of the recombinant vector DNA into the target cell. Cells containing the recombinant vector DNA may then be selected for using methods known in the art such as via a selection marker expressed in the vector, and the selected cells may then be re-introduced into the individual to express the PrtR-PrtK complex.

As an alternative to active immunization, immunization may be passive, i.e. immunization comprising administration of purified immunoglobulin containing antibody against PrtR-PrtK.

The present invention further provides the nucleotide sequence of the genes encoding the PrtR-PrtK complex, as well as the amino acid sequence deduced from the isolated genes. According to one embodiment of the present invention, using recombinant DNA techniques the genes encoding the PrtR-PrtK complex are incorporated into an expression vector, and the recombinant vector is introduced into an appropriate host cell thereby directing the expression of these sequences in that particular host cell. The expression system, comprising the recombinant vector introduced into the host cell, can be used (a) to produce PrtR-PrtK complex which can be purified for use as an immunogen in vaccine formulations; (b) to produce PrtR-PrtK complex to be used as an antigen for diagnostic immunoassays or for generating *P. gingivalis*-specific antisera of therapeutic and/or diagnostic value; (c) or if the recombinant expression vector is a live virus such as vaccinia virus, the vector itself may be used as a live or inactivated vaccine preparation to be introduced into the host's cells for expression of PrtR-PrtK complex; (d) for introduction into live attenuated bacterial cells or genetically engineered commensal intraoral bacteria which are used to express PrtR-PrtK complex to vaccinate individuals; (e) or for introduction directly into an individual to immunize against the encoded and expressed PrtR-PrtK complex. In particular the recombinant bacterial vaccine can be based on a commensal inhabitant of the human oral cavity or animal if the vaccine is to prevent periodontal disease in animals. The recombinant bacterial vaccine expressing inactivated PrtR-PrtK can be used to colonise the oral cavity, supragingival or subgingival plaque. The intra-oral bacterium can be isolated from the patient with periodontitis and genetically engineered to express inactivated PrtR-PrtK complex. The production of the inactivated PrtR-PrtK within the oral cavity will not be toxic to the oral mucosal tissues. However, the inactivated PrtR-PrtK will stimulate the mucosal-associated lymphoid tissues (MALT) to produce specific antibody to neutralise the PrtR-PrtK of *P. gingivalis*.

Successful expression of a protein or peptide requires that either the insert comprising the gene or gene fragment, or the vector itself, contain the necessary elements for transcription and translation which is compatible with, and recognized by the particular host system used for expression. A variety of host systems may be utilized to express the PrtR-PrtK, which include, but are not limited to bacteria transformed with a bacteriophage vector, plasmid vector, or cosmid DNA, yeast containing yeast vectors; fungi containing fungal vectors; insect cell lines infected with virus (e.g. baculovirus); and mammalian cell lines transfected with plasmid or viral expression vectors, or infected with recombinant virus (e.g. vaccinia virus, adenovirus, adeno-associated virus, retrovirus, etc.).

Using methods known in the art of molecular biology various promoters and enhancers can be incorporated into the vector or the DNA sequence encoding PrtR-PrtK to increase the expression of the PrtR-PrtK amino acid sequences, provided that the increased expression of the amino acid sequences is compatible with (for example, non-toxic to) the particular host cell system used. Further, the DNA can be fused to DNA encoding other antigens, such as other bacterial outer membrane proteins, or other bacterial, fungal, parasitic, or viral antigens to create a genetically fused (sharing a common peptide backbone) multivalent antigen for use as an improved vaccine composition.

The selection of the promoter will depend on the expression system used. Promoters vary in strength, i.e. ability to facilitate transcription. Generally, for the purpose of expressing a cloned gene, it is desirable to use a strong promoter in order to obtain a high level of transcription of the gene and expression into gene product. For example, bacterial, phage, or plasmid promoters known in the art from which a high level of transcription have been observed in a host cell system comprising *E. coli* include the lac promoter, trp promoter, recA promoter, ribosomal RNA promoter, the $P_R$ and $P_L$ promoters, lacUV5, ompF, bla, lpp, and the like, may be used to provide transcription of the inserted DNA sequence encoding PrtR-PrtK.

Additional, if PrtR-PrtK protein may be lethal or detrimental to the host cells, the host cell strain/line and expression vectors may be chosen such that the action of the promoter is inhibited until specifically induced. For example, in certain operons the addition of specific inducers is necessary for efficient transcription of the inserted DNA (e.g., the lac operon is induced by the addition of lactose or isopropylthio-beta-D-galactoside). A variety of operons such as the trp operon, are under different control mechanisms. The trp operon is induced when tryptophan is absent in the growth media. The PL promoter can be induced by an increase in temperature of host cells containing a temperature sensitive lambda repressor. In this way, greater than 95% of the promoter-directed transcription may be inhibited in uninduced cells. Thus, expression of recombinant PrtR-PrtK protein may be controlled by culturing transformed or transfected cells under conditions such that the promoter controlling the expression from the inserted DNA encoding PrtR-PrtK amino acid sequences is not induced, and when the cells reach a suitable density in the growth medium, the promoter can be induced for expression from the inserted DNA.

Other control elements for efficient gene transcription or message translation include enchancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed either upstream or downstream from the inserted DNA sequences encoding PrtR-PrtK amino acid sequences to increase transcriptional efficiency. These or other regulatory sites, such as transcription or translation initiation signals, can be used to regulate the expression of the gene encoding PrtR-PrtK. Such regulatory elements may be inserted into DNA sequences encoding PrtR-PrtK amino acid sequences or nearby vector DNA sequences using recombinant DNA methods described herein for insertion of DNA sequences.

Accordingly, *P. gingivalis* nucleotide sequences containing regions encoding for PrtR-PrtK, can be ligated into an expression vector at a specific site in relation to the vectors promoter, control, and regulatory elements so that when the recombinant vector is introduced into the host cell the *P. gingivalis*-specific DNA sequences can be expressed in the host cell. For example, the PrtR-PrtK specific DNA sequences containing their own regulatory elements can be ligated into an expression vector in a relation or orientation to the vector promoter and control elements which will allow for co-expression of the PrtR and PrtK. The recombinant vector is then introduced into the appropriate host cells, and the host cells are selected, and screened for those cells containing the recombinant vector. Selection and screening may be accomplished by methods known in the art including detecting the expression of a marker gene (e.g., drug resistance marker) present in the plasmid, immunoscreening for production of PrtR-PrtK specific epitopes using antisera generated to PrtR-PrtK specific epitopes, and probing the DNA of the host's cells for PrtR-PrtK specific nucleotide sequence using one or more oligonucleotides and methods described herein.

Genetic engineering techniques may also be used to characterize, modify and/or adapt the encoded PrtR-PrtK protein. For example, site-directed mutagenesis to inactivate the protease domains of the PrtR-PrtK and to modify the protein in regions outside the protective domains, may be desirable to increase the safety and solubility.

In particular the host organism for the vector containing the PrtR-PrtK genes and constructs can be a commensal inhabitant of the oral cavity; for example an inhabitant of subgingival plaque, supragingival plaque or a bacterium associated with the oral mucosa. Examples of commensal intra-oral bacteria would be Streptococcus species and Actinomyces species, eg. *Streptococcus salivarius, Streptococcas sanguis, Actinomyces naeslundii.* These organisms can be isolated from the periodontitis patient and then genetically engineered to express the inactivated PrtR-PrtK. The DNA encoding the PrtR-PrtK could be linked with DNA encoding leader sequences of extracellular proteins of these commensal intra-oral bacteria. The DNA encoding the PrtR-PrtK could also be linked with, or inserted into, the DNA encoding extracellular proteins to produce secreted fusion proteins. Examples of extracellular proteins that could be used to produce fusion proteins with the inactivated PrtR-PrtK could be the glucosyltranferases (GTF) or fructosyltransferases (FTF). The recombinant organism would be then re-introduced into the patients oral cavity and once colonised the oral mucosa or teeth would express the inactivated PrtR-PrtK to stimulate the mucosal associated lymphoid tissue to produce neutralising antibodies.

Due to the conservation of the genes encoding PrtR-PrtK, the nucleic acid sequences of the present invention can be used in molecular diagnostic assays for detecting *P. gingivalis* genetic material. In particular, PrtR-PrtK sequence-specific oligonucleotides can be synthesized for use as primers and/or probes in amplifying, and detecting amplified, nucleic acids from *P. gingivalis.* Recent advances in molecular biology have provided several means for enzymatically amplifying nucleic acid sequences. Currently the most commonly used method, PCR™ (polymerase chain reaction Cetus Corporation) involved the use of Taq Polymerase, known sequences as primers, and heating cycles which separate the replicating deoxyribonucleic acid (DNA) strands and exponentially amplify a gene of interest. Other amplification methods currently under development include LCR™ (ligase chain reaction, BioTechnica International) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA™ (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$–$10^4$ organisms per specimen (1990, *Gene Probes for Bacteria,* eds. Macario and deMacario, Academic Press). Coupled with a method that allows for amplification of specific target DNA sequences, species-specific nucleic acid probes can greatly increase the level of sensitivity in detecting organisms in a clinical specimen. Use of these probes may allow direct detection without relying on prior culture and/or conventional biochemical identification techniques. This embodiment of the present invention is directed to primers which amplify species-specific sequences of the genes encoding PrtR-PrtK of *P. gingivalis,* and to probes which specifically hybridize with these amplified DNA fragments. By using the nucleic acid sequences of the present invention and according to the methods of the present invention, as few as one *P. gingivalis* organism may be detected in the presence of 10 ug/ml extraneous DNA.

DNA may be extracted from clinical specimens which may contain *P. gingivalis* using methods known in the art. For example, cells contained in the specimen may be washed in TE buffer and pelleted by centrifugation. The cells then may be resuspended in 100 ul of amplification reaction buffer containing detergents and proteinase K. Using the polymerase chain reaction, the resultant sample may be composed of the cells in 10 mM Tris pH 8.3, 50 mM KCl, 1.5 mM $MgCl_2$, 0.01% gelatin, 0.45% NP40™, 0.045% Tween 20™, and 60 ug/ml proteinase K. The sample is incubated in a 55° C. water bath for 1 hour. Following the incubation, the sample is incubated at 95° C. for 10 minutes to heat-inactivate the proteinase K. The sample may then be amplified in accordance with standard PCR protocols.

The following examples are further illustrative of the nature of the present invention, but it is understood that the invention is not limited thereto. All amounts and proportions referred to herein are by weight unless otherwise indicated.

EXAMPLE 1

(1) Preparation of Antigen

A. Anion Exchange and Affinity Chromatography

*P. gingivalis* W50 was grown anaerobically at 37° C. on lysed horse blood agar and in modified BM media containing 1 $\mu$g/ml hemin. Bacteria were maintained on lysed horse blood plates by routine passage (<10 passages) and used to inoculate batch cultures. Batch culture growth in Brain Heart Infusion medium was monitored at 650 nm using a spectrophotometer (295E, Perkin-Elmer). Culture purity was checked routinely by Gram stain, microscopic examination and by using a variety of biochemical tests. Stocks were maintained as lyophilised cultures. A culture of *P. gingivalis* was grown to late logarithmic phase and the cells harvested by centrifugation (5,000×g, 20 min, 4° C.) and then resuspended in 160 ml TC buffer (20 mM Tris-HCl pH 7.4 and 5 mM $CaCl_2$) containing 50 mM NaCl and subjected to mild sonication using a Branson Sonifier 250 with an output control of 3 and a 50% duty cycle for 15 min at 4° C. The sonicate was centrifuged (100,000×g, 30 min, 4° C.) and the supernatant filtered (0.22 $\mu$m) prior to anion-exchange FPLC. The sonicate was applied to an anion-exchange column (Hiload XK 16/10 Q Sepharose, Pharmacia-LKB) cooled to 4° C., in multiple injections using a 50 ml superloop (Pharmacia-LKB). The sample was eluted using a linear gradient from 0–100% buffer B over 90 min at a flow rate of 2.0 ml $min^{-1}$. The eluant was monitored at 280 nm and collected in 6 ml fractions using a Frac 100 fraction collector (Pharmacia-LKB). Buffer A was TC buffer containing 50 mM NaCl and buffer B was TC buffer containing 500 mM NaCl. Fractions were analysed for proteolytic and amidolytic activity using azocasein (A-2765, Sigma Chemical Co. St Louis, Mo.), benzoyl-L-Arg-p-nitroanilide (Bz-L-Arg-pNa, Sigma) and benzyloxycarbonyl-L-Lys-p-nitroanilide (Z-L-Lys-pNa, Calbiochem, Melbourne, Australia) vide infra. Anion-exchange fractions containing the majority of proteolytic/amidolytic activity were pooled, washed and then concentrated in TC buffer containing 150 mM NaCl using a centricon 10 micro-concentrator (Amicon). The sample was then divided into four aliquots and each was independently applied to a gel filtration column (Superose 12, HR 10/30, Pharmacia-LKB) using TC buffer containing 150 mM NaCl at a flow rate of 0.3 ml $min^{-1}$. The eluant was monitored at 280 nm and peaks collected using a Frac 100 fraction collector. The $M_r$ values of eluant peaks were determined using molecular mass gel filtration standards (Pharmacia-LKB). The peak containing the majority of the proteolytic/amidolytic activity was concentrated using a centricon 10 micro-concentrator and then applied at a flow rate of 0.1 ml $min^{-1}$ to an Arg-sepharose column (5 ml arginine-Sepharose 4B beads, HR 5/5 column, Pharmacia-LKB) and the unbound material collected. The column was washed with 500 mM NaCl and re-equilibrated with TC buffer containing 50 mM NaCl. The column was first eluted with 200 mM lysine-HCl pH 7.4 in TC buffer containing 50 mM NaCl at a flow rate of 0.1 ml $min^{-1}$. This was followed by 750 mM lysine-HCl pH 7.4 in the same buffer. The column was then re-equilibrated with TC buffer containing 50 mM NaCl and then eluted with 200 mM arginine-HCl pH 7.4 in TC buffer containing 50 mM NaCl at a flow rate of 0.1 ml $min^{-1}$. The unbound material collected was then re-applied to the Arg-sepharose column and the elution steps repeated. This sequence was repeated until all proteolytic activity had bound to the column. The eluant was monitored at 280 nm and peaks collected using a Frac 100 fraction collector. The peaks eluted from the Arg-sepharose by 200 mM lysine and 200 mM arginine were equilibrated with TC buffer containing 50 mM NaCl and 1.0% octyl-β-D-glucopyranoside and then applied to a Mono Q (HR 5/5) anion-exchange column and eluted using a linear gradient of 0–100% buffer B at a flow rate of 1.0 ml $min^{-1}$. Buffer A was TC buffer containing 50 mM NaCl and 0.1% octyl-β-D-glucopyranoside and buffer B was TC buffer containing 500 mM NaCl and 0.1% octyl-β-D-glucopyranoside. The eluant was monitored at 280 nm and eluant peaks collected using a Frac 100 fraction collector.

Azocasein, Bz-L-Arg-pNa and z-L-lys-pNa were used to routinely assay FPLC fractions for proteolytic and amidolytic activity. A sample of each fraction (20–200:1) was incubated at 37° C. with azocasein (5 mg/ml final concentration) in TC buffer pH 8.0 containing 150 mM NaCl and 10 mM cysteine. For azocasein the reaction was stopped by the addition of 30% trichloroacetic acid at 4° C. Samples were centrifuged and the $A_{440}$ of the supernatant measured using a spectrophotometer (Perkin Elmer, model 552).

For the synthetic chromogenic substrates samples of each chromatographic fraction (5–50:1) were incubated at 37° C. with Bz-L-Arg-pNa or z-L-Lys-pNa (1.0 mM final concentration) in a total volume of 350:1 100 mM Tris-HCl pH 8.0 buffer containing 150 mM NaCl, 10 mM cysteine and 5 mM $CaCl_2$. Inhibitors and activators were added to the purified enzymes in 100 mM Tris-HCl pH 8.0 buffer containing 150 mM NaCl. Absorbance was measured at 410 nm in a Hewlett Packard 8452A Diode Array spectrophometer and the amidolytic activity expressed in U, where U=μmol substrate converted $min^{-1}$ at 37° C. Trypsin (E.C.3.4.21.4, T 8253 Sigma) was used as a standard. The protein concentration of FPLC fractions and purified samples was determined using the Bradford protein assay (Biorad) with BSA as a standard.

A sample of the gel filtration chromatographic fraction (20 μl) exhibiting the major proteolytic and amidolytic activity was incubated for 4 h at 37° C. with 10 mg/ml of pure $\alpha_{s1}$-casein dissolved in TC buffer pH 8.0 containing 150 mM NaCl and 50 mM 2-mercaptoethanol. Following incubation the sample was equilibrated in 0.1% TFA (v/v) dissolved in Milli Q water (Buffer A). The sample was then applied to an HPLC reversed phase analytical column (C8, 7 μm, 4.6 mm×220 mm, Applied Biosystems Inc. Brownlee Aquapore RP 300) and peptides eluted using a linear gradient from 0–100% buffer B over 40 min at a flow rate of 1 ml $min^{-1}$ (140A solvent delivery system). Buffer B was 80% acetonitrile (v/v) in 0.1% (v/v) TFA in Milli Q water. The eluant was monitored at 214 nm using a 1000S diode array detector (Applied Biosystems). Peaks were collected manually and peptides identified using a combination of amino acid composition and sequence analyses as described previously.

SDS-PAGE was performed using a Mini protean II electrophoresis system (Biorad) with 12% (w/v), 1 mm separating gels, overlaid with 5% stacking gels (Laemmli, 1970) [Nature 277:680–685]. Two volumes of each sample were mixed with one volume of buffer [0.5 M Tris-HCl, pH 6.8, 5% v/v 2-mercaptoethanol, 10.0% w/v SDS, 0.05% w/v bromophenol blue (75% v/v) and glycerol (25% v/v)] and heated to 100° C. for 4 min unless otherwise stated. SDS-PAGE was performed at room temperature using a current of 30–50 mA and a potential difference of ≦200 V. For silver staining, gels were fixed in methanol/water/acetic acid (45/45/10, v/v/v), washed in Milli Q water, reduced with 5 μg/ml dithiothreitol and then washed in Milli Q water, all for 30 min periods. Gels were then stained for 20 min with 0.1% w/v $AgNO_3$ and developed with 3% w/v sodium carbonate containing 0.1% v/v formaldehyde and development stopped with glacial acetic acid. For Coomassie blue staining, gels were fixed in 12% TCA and stained overnight using 0.1% (w/v) purified Coomassie brilliant blue G 250 in 2% (w/v) phosphoric acid, 6% (w/v) ammonium sulphate. Gels were destained with methanol/water/acetic acid (50/40/10, v/v/v). Proteins were transferred onto a PVDF membrane (Problott, Applied Biosystems Inc. (ABI)) for sequence analysis using a transblot cell (Biorad). PVDF membrane was wetted in 100% methanol and soaked in transfer buffer (10 mM CAPS/10% methanol, pH 11.5). Transfer was performed using a potential difference of 60 V (300 mA) for 90 min. Membranes were briefly stained using 0.1% (w/v) Coomassie brilliant blue R 250 in methanol/water/acetic acid (5/5/1, v/v/v). Protein bands were excised, destained for 10–30 sec in 50% methanol and then the N-terminal sequence determined using a Hewlett Packard 10005A protein sequencer or a modified ABI 471-02A protein sequencer fitted with a blott cartridge.

Figure 2:
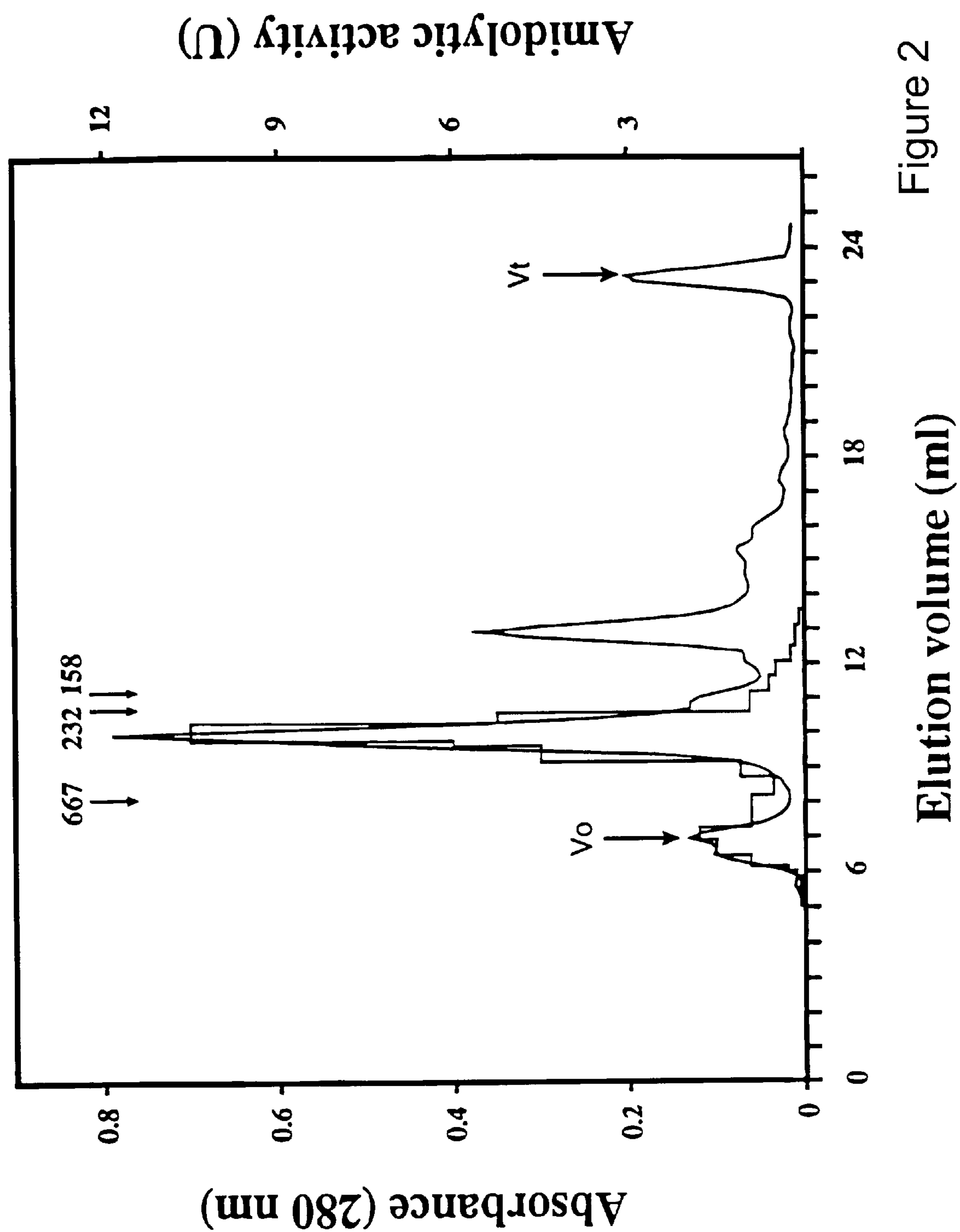
FIG. 2. Gel filtration FPLC of the pooled and concentrated fractions from Q sepharose anion exchange FPLC containing proteolytic/amidolytic activity. Anion exchange fractions containing the major peak of proteolytic/amidolytic activity were pooled, equilibrated in TC buffer containing 150 mM NaCl, concentrated and divided into four aliquots and each then independently applied to a gel filtration column (Superose 12 HR 10/30) and eluted using the same buffer at a flow rate of 0.3 ml $min^{-1}$. Fractions (0.5 ml) were assayed for proteolytic and amidolytic activity. Bz-L-Arg-pNA amidolytic activity is shown by the histogram. Vo and Vt indicate the void and total volumes of the column respectively. The elution volumes of the standard proteins thyroglobulin 667 kDa, catalase 232 kDa and aldolase 158 kDa are marked.
Figure 3:
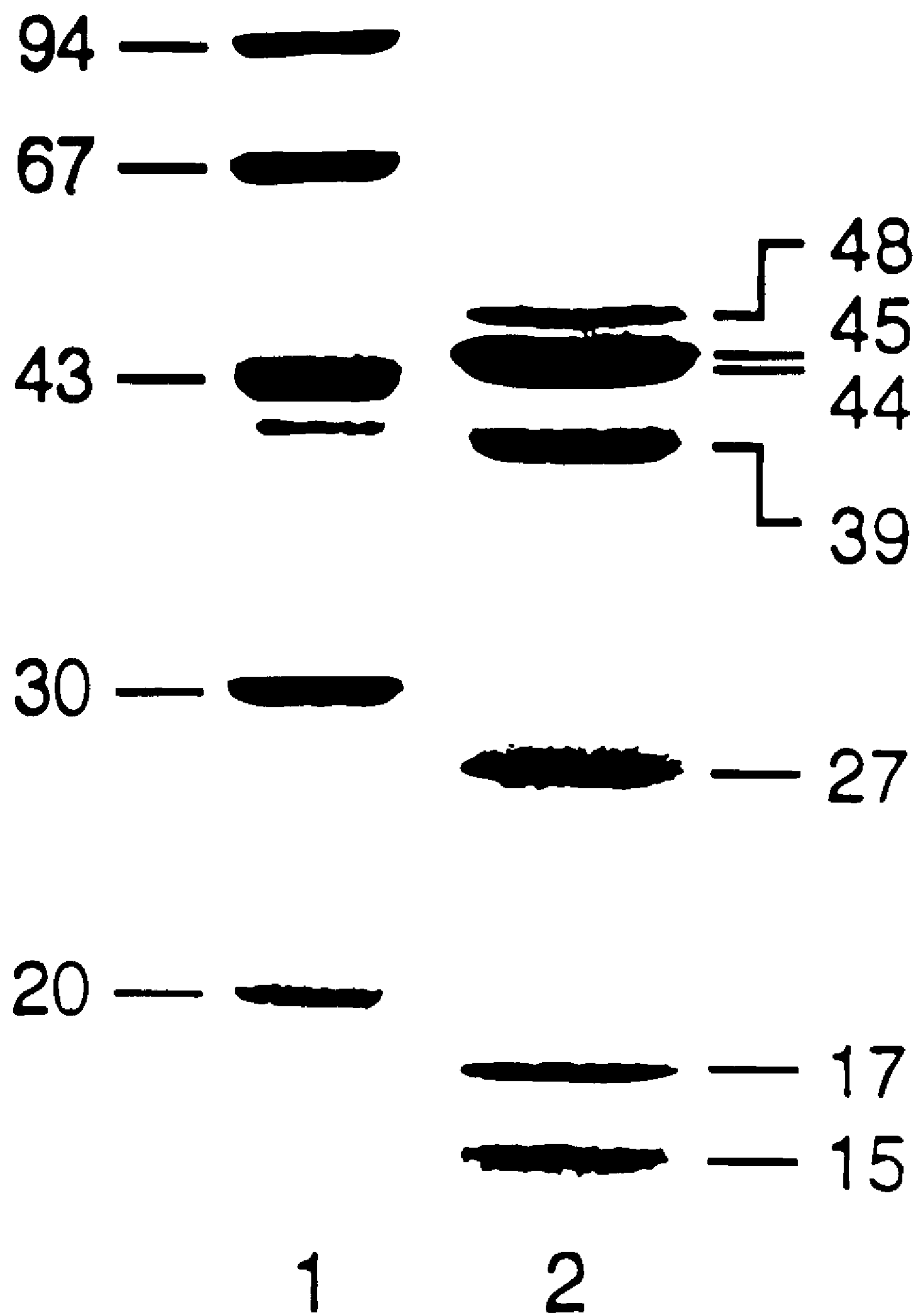
FIG. 3. SDS-PAGE (boiled/reduced conditions) of the 300 kDa peak from gel filtration (Superose 12 HR 10/30) FPLC. Lane 1, Pharmacia molecular mass standards ($M_r$ shown in kDa). Lane 2, 300 kDa peak from gel filtration FPLC. Coomassie blue stained gel.

The ultrasonication procedure was effective at releasing the cell-associated Arg- and Lys-specific proteolytic activity of *P. gingivalis* W50 and 15 min was required for maximal release of activity. The sonicate of *P. gingivalis* W50 cells contained 0.30 mg $ml^{-1}$ protein and 2.6 and 2.3 μmol $min^{-1}$ mg $protein^{-1}$ activity with 1.0 mM Bz-L-Arg-pNA and z-L-Lys-pNA as substrate respectively at 37° C. The crude sonicate was subjected to Q-sepharose anion exchange FPLC and a representative chromatogram is presented in FIG. 1. Proteolytic/amidolytic activity eluted as one major peak between 246–320 mM NaCl (FIG. 1) which was collected, concentrated using a centricon-10 (Amicon) and then applied to the Superose 12 gel filtration column (FIG. 2). Molecular mass gel filtration standards were used to determine the $M_4$ of the peaks obtained and the major peak, which also exhibited the major proteolytic/amidolytic activity, corresponded to 300 kDa (FIG. 2). Proteolytic/amidolytic activity was also associated with the high molecular mass material (0.6→2.0×$10^6$ Da) eluted from the gel filtration column. The 300 kDa gel filtration peak contained seven bands at 48, 45, 44, 39, 27, 17 and 15 kDa on SDS-PAGE analysis (FIG. 3). The seven bands were transblotted and subjected to N-terminal sequence analysis (Table 1). This analysis revealed that the 44 kDa band contained two proteins and the N-terminal sequences of these two 44 kDa proteins were assigned after further purification. The N-terminal sequence of one of the 44 kDa proteins was identical to that of the 17 kDa protein and the 39 kDa and 27 kDa proteins also had identical N-termini (Table 1).

TABLE 1

N-terminal sequences of proteins in the 300 kDa complex separated by SDS-PAGE

| Band | N-terminal sequence (kDa) |
|---|---|
| 48* | DVYTDHGDLYNTPVRML<br>SEQ ID NO:1 |
| 45† | YTPVEEKQNGRMIVIVAKKYEGD<br>SEQ ID NO:2 |

TABLE 1-continued

N-terminal sequences of proteins in the 300 kDa complex separated by SDS-PAGE

| Band | N-terminal sequence (kDa) |
|---|---|
| 44[†] | SGQAEIVLEAHDVWNDGSGYQILLDADHDQYGQVIPSDTHFL SEQ ID NO:3 |
| 44* | PQSVWIERTVDLPAGTKYVAFR SEQ ID NO:4 |
| 39* | ANEAKVVLAADNVWGDNTGYQFLLDA SEQ ID NO:5 |
| 27[†] | ANEAKVVLAADNVWGDNTGYQFLLDA SEQ ID NO:5 |
| 17[†] | PQSVWIERTVDLPAGTKYVAFR SEQ ID NO:4 |
| 15*,[†] | ADFTETFESSTHGEAPAEWTTIDA SEQ ID NO:6 |

*Proteins eluted from Arg-sepharose by 200 mM lysine
[†]Proteins eluted from Arg-sepharose by 200 mM arginine Repeated gel filtration analyses of the Q-sepharose purified material or crude sonicates indicated that the major proteolytic/amidolytic activity was associated with a peak corresponding to 300 kDa and higher molecular mass ($0.6\rightarrow2\times10^6$ Da) material that when boiled in SDS and subjected to SDS-PAGE analysis contained the same seven bands at 48, 45, 44, 39, 27, 17 and 15 kDa (FIG. 3).

Figure 4:
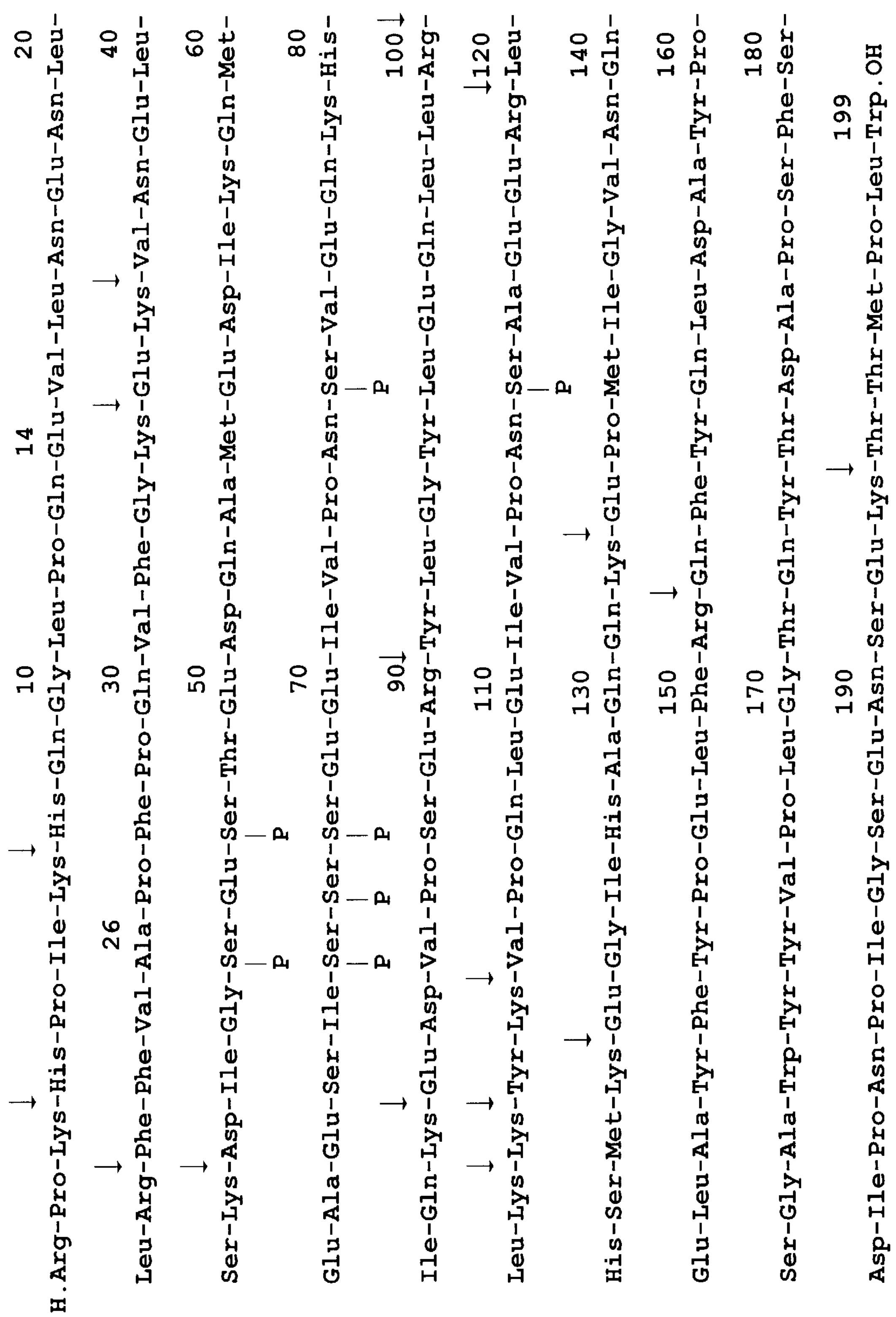
FIG. 4. Specific cleavage sites (marked with arrows) of $\alpha_{s1}$-casein by the proteolytic/amidolytic peak from gel filtration FPLC corresponding to 300 kDa. The protein $\alpha_{s1}$-casein was cleaved on the carboxyl side of arginyl and lysyl residues only.
Figure 5:
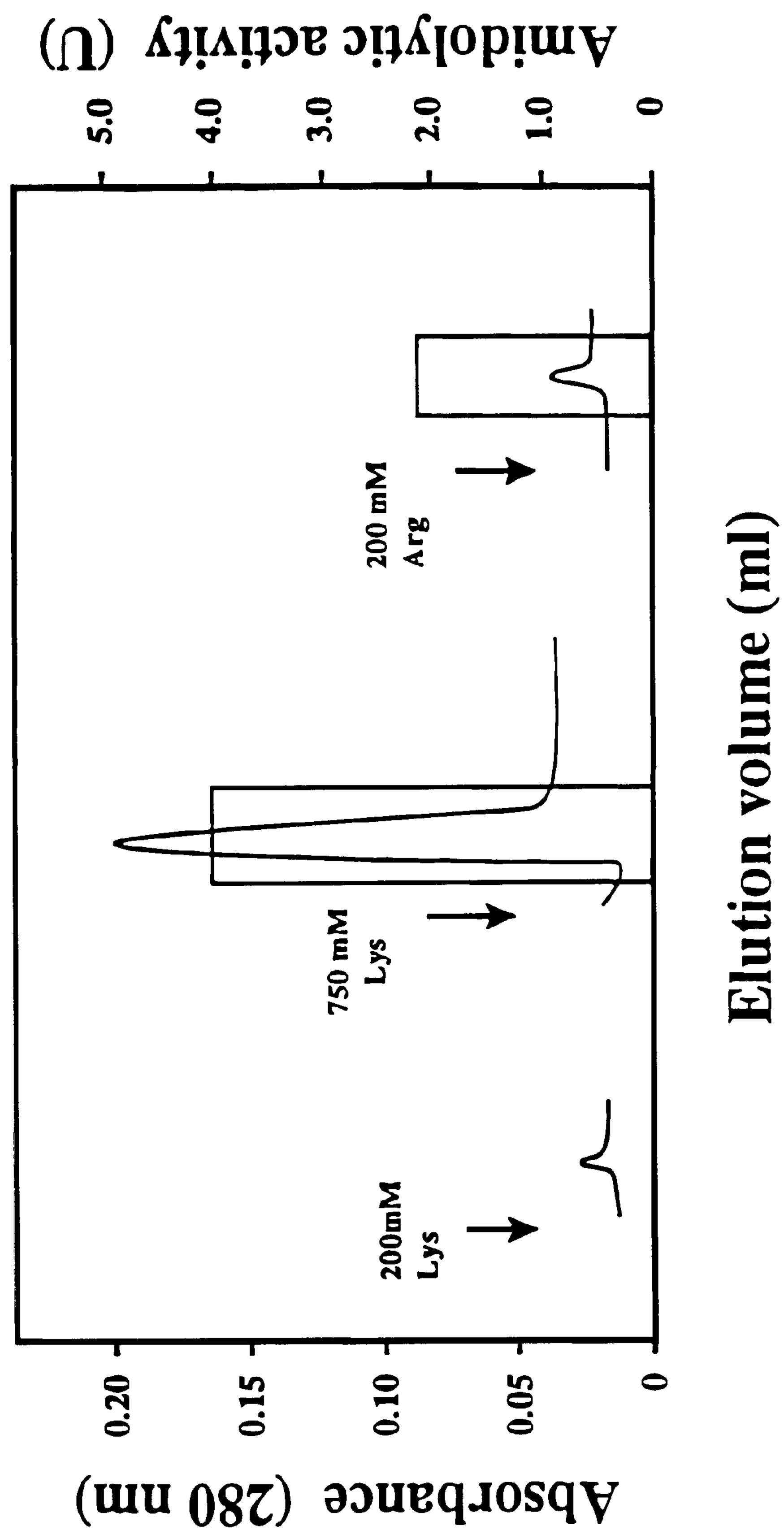
FIG. 5. Arg-sepharose FPLC of the 300 kDa gel filtration peak exhibiting Arg- and Lys-specific proteolytic activity. Gel filtration fractions containing the major peak of proteolytic activity (300 kDa) were pooled and applied to an arginine-sepharose column (5 ml arginine-Sepharose 4B) and washed with TC buffer containing 50 mM NaCl at 0.1 ml $min^{-1}$until the baseline returned to zero. The column was then further washed with 500 mM NaCl and then re-equilibrated with TC buffer containing 50 mM NaCl. The column was first eluted with 200 mM lysine in TC buffer containing 50 mM NaCl, followed by 750 mM lysine in the same buffer. The column was then re-equilibrated and eluted with 200 mM arginine in the same buffer at a flow rate of 0.1 ml $min^{-1}$. Peaks were collected and assayed for amidolytic and proteolytic activity. Bz-L-Arg-pNA amidolytic activity is shown by the histogram and the arrows indicate the start of each step gradient.
Figure 6:
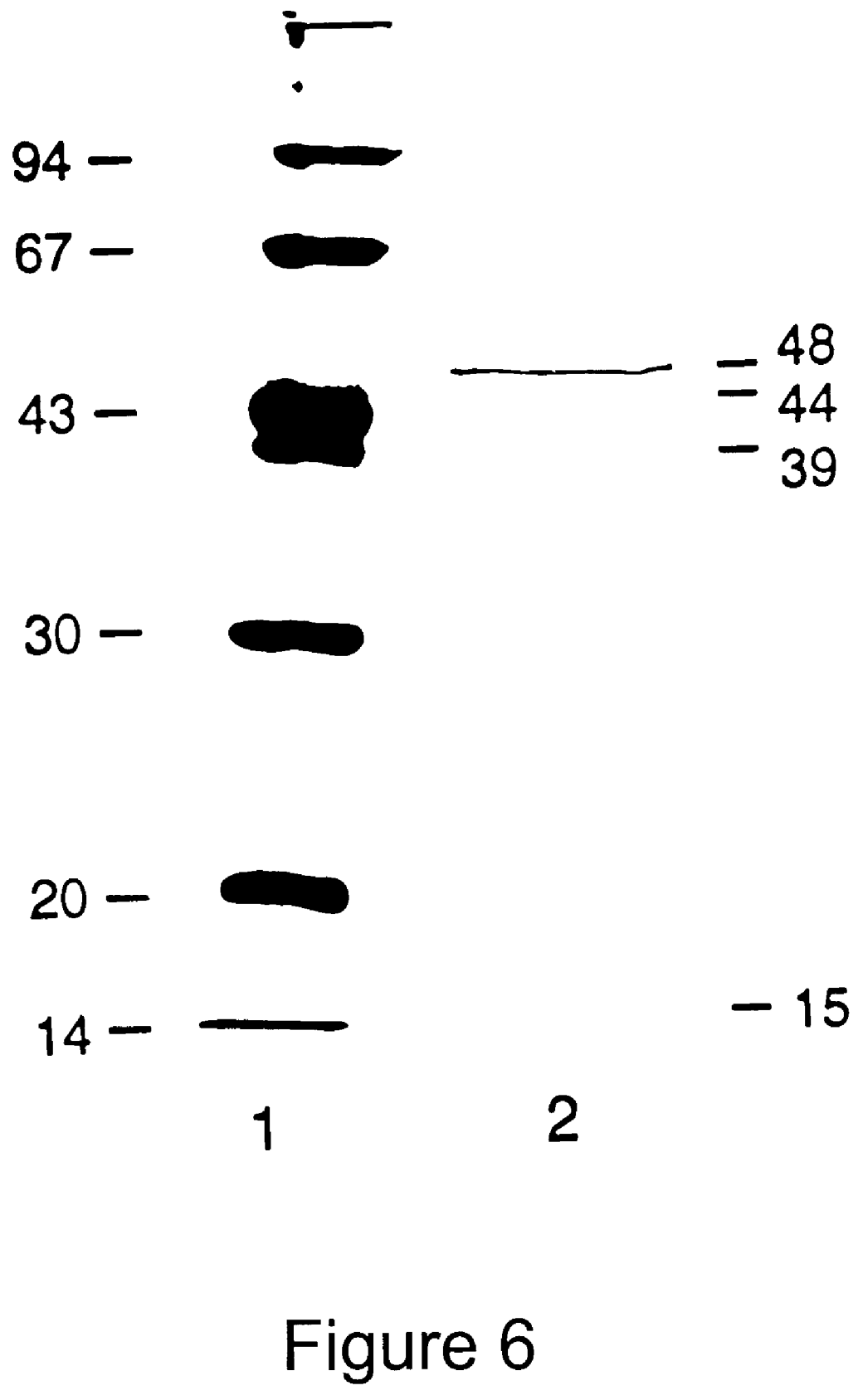
Figure 7:
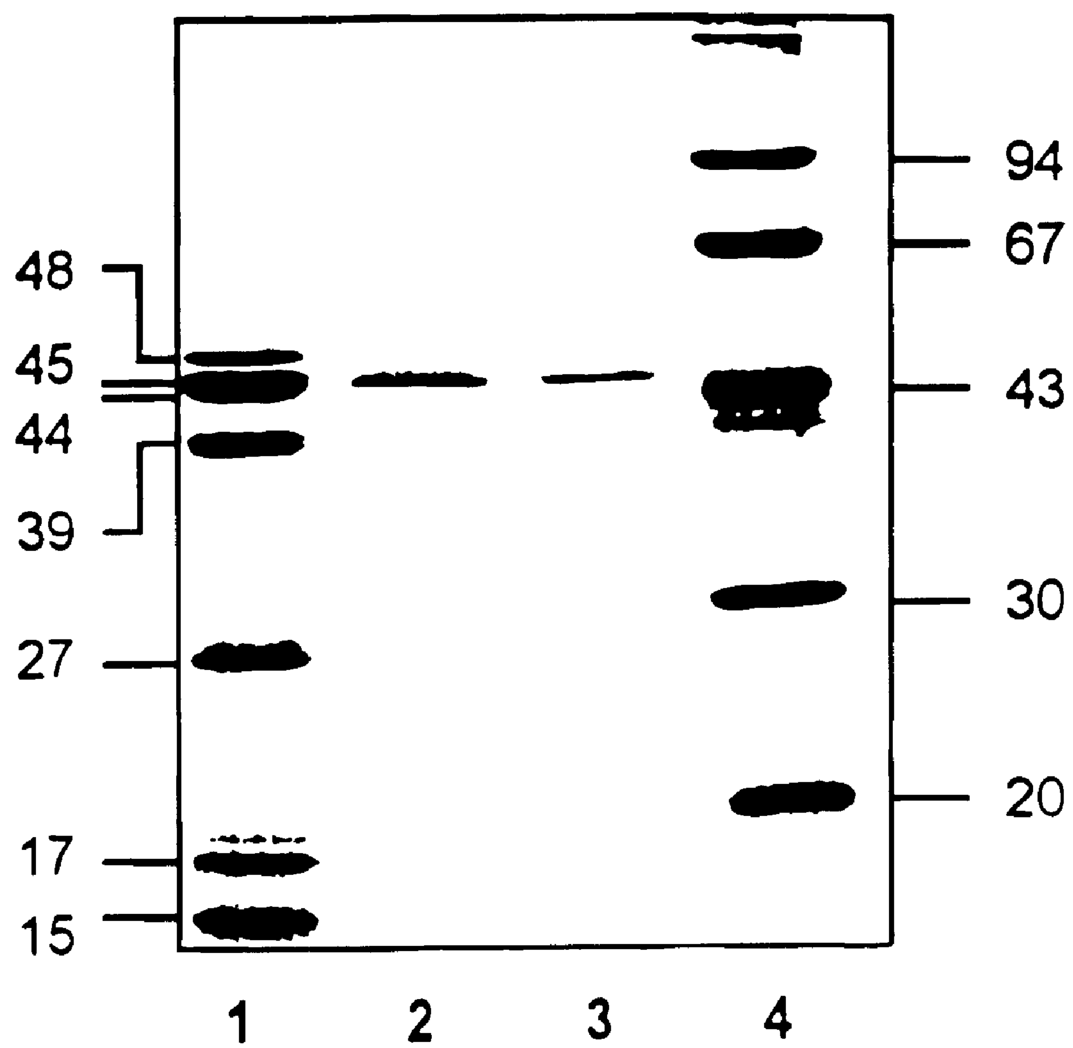
FIG. 7. SDS-PAGE (boiled/reduced conditions) of the 750 mM lysine and 200 mM arginine eluants from the arginine-Sepharose FPLC and the purified 45 kDa Arg-specific endopeptidase. Lane 1, 750 mM lysine eluant. Lane 2, 200 mM arginine eluant. Lane 3, purified 45 kDa Arg-specific endopeptidase. Lane 4, Pharmacia molecular mass standards ($M_r$ shown in kDa). Coomassie blue stained gel.

The 300 kDa gel filtration protein complex was incubated with $\alpha_{s1}$-casein. The $\alpha_{s1}$-casein peptides released by the action of the proteolytic activity of the 300 kDa complex were purified by RP-HPLC and identified by amino acid composition and sequence analyses. The sites of $\alpha_{s1}$-casein cleavage by the material of the 300 kDa complex were the carboxyl side of arginyl and lysyl residues only (FIG. 4). All arginyl and lysyl residues of $\alpha_{s1}$-casein were cleaved except the N-terminal Arg and the Lys residues flanking the Ser(P) cluster sequence, presumably due to the high negative charge density (FIG. 4). The 300 kDa complex was then applied to an Arg-sepharose column and washed with TC buffer containing 500 mM NaCl (FIG. 5). The Arg-sepharose was eluted first with 200 mM lysine in TC buffer (FIG. 5) which eluted a small amount of the 48 kDa, 44 kDa, 39 kDa and 15 kDa proteins of the 300 kDa complex as shown by SDS-PAGE (FIG. 6 and Table 1). N-terminal sequence analysis of these transblotted proteins revealed that only one of the 44 kDa proteins of the 300 kDa complex was eluted with 200 mM lysine (Table 1). This fraction eluted from Arg-sepharose with 200 mM lysine contained only Lys-specific proteolytic/amidolytic activity. Next the Arg-sepharose column was eluted with 750 mM lysine (FIG. 5) which removed the majority of the protein bound as the undissociated 300 kDa complex containing all seven bands (eight proteins) as shown by SDS-PAGE analysis (FIG. 7). The 750 mM lysine eluant exhibited both Arg- and Lys-specific proteolytic/amidolytic activity characteristic of the 300 kDa complex. The Arg-sepharose column was then eluted with 200 mM arginine in TC buffer (FIG. 5). The 200 mM arginine eluant contained small amounts of the 45, 44, 27, 17 and 15 kDa proteins as shown by SDS-PAGE (FIG. 7). This fraction exhibited only Arg-specific proteolytic/amidolytic activity. N-terminal sequence analysis of these transblotted proteins eluted with 200 mM arginine revealed that only one of the 44 kDa proteins of the 300 kDa complex was eluted with 200 mM arginine and this 44 kDa protein was different to the 44 kDa protein eluted with 200 mM lysine (Table 1).

The proteins eluted from the Arg-sepharose column with 200 mM lysine and 200 mM arginine were washed, concentrated and equilibrated with TC buffer containing 50 mM NaCl and 1.0% octyl-β-D-glucopyranoside and applied independently to a Mono Q anion exchange column. Elution from the Mono Q column with a NaCl gradient associated the Arg-specific proteolytic activity with the 45 kDa protein with a 25 fold purification over the original crude sonicate (Table 2, FIG. 7). The specificity of the 45 kDa proteinase for arginyl residues was confirmed by the enzyme cleaving Bz-L-Arg-pNA but not z-L-Lys-pNA. The Arg-specific 45 kDa enzyme was activated by thiols (particularly cysteine), not inhibited by PMSF or AEBSF but inhibited by sulphydryl-directed reagents, leupeptin and EDTA (Table 3). The inhibition by EDTA could be reversed by the addition of $Ca^{2+}$ (Table 3). The pH optimum of the enzyme was 7.5–8.0 and activity dropped off dramatically as the pH was lowered below 7.0. These results indicate that the 45 kDa enzyme is a calcium-stabilized, Arg-specific cysteine endopeptidase. The Lys-specific activity was characterized using the substrate Z-L-Lys-pNA and was associated with the 48 kDa protein purified from the 200 mM lysine eluant by Mono Q FPLC. The Lys-specific enzyme was also activated by thiols and inhibited by sulphydryl-directed reagents but was not inhibited by leupeptin or EDTA. Non-reducing SDS-PAGE without boiling of the 300 kDa complex produced bands corresponding to the relative molecular masses of approximately 300, 150, 104, 88, 76 and 66 kDa.

TABLE 2

Purification of the 45 kDa Arg-specific proteinase PrtR45

| Step | Protein (mg) | Proteolytic activity (U*) | Specific activity U mg$^{-1}$ | Purification fold | Yield % |
|---|---|---|---|---|---|
| Sonicate | 48.0 | 124 | 2.6 | 1 | 100 |
| Anion Exchange FPLC (Q-sepharose) | 8.2 | 64 | 7.8 | 3 | 52 |
| Gel filtration FPLC (Superose 12) | 3.9 | 46 | 11.8 | 5 | 37 |
| Affinity FPLC (Arg-sepharose) | 0.7 | 17 | 24.3 | 9 | 14 |
| Anion exchange FPLC (mono Q) | 0.2 | 13 | 65.0 | 25 | 11 |

*Amidolytic activity using 1.0 mM Bz-L-Arg-pNA; 1 unit = μmol min$^{-1}$ at 37° C.

TABLE 3

Effects of various activators/inhibitors on the activity of the 45 kDa Arg-specific proteinase

| Compound | Concentration (mM) | Activity (%) |
|---|---|---|
| 2-mercaptoethanol | 1.0 | 100 |
| | 10.0 | 158 |
| | 50.0 | 189 |
| Dithiothreitol | 1.0 | 109 |
| | 10.0 | 174 |
| L-cysteine | 0.1 | 183 |
| | 1.0 | 320 |
| | 10.0 | 487 |
| PMSF*,[†] | 1.0 | 100 |
| | 10.0 | 90 |
| AEBSF*,[†] | 1.0 | 93 |
| | 10.0 | 80 |
| Iodoacetic acid[†] | 1.0 | 82 |
| | 10.0 | 19 |
| PCMB*,[†] | 1.0 | 100 |
| | 10.0 | 14 |

TABLE 3-continued

Effects of various activators/inhibitors on the activity of the 45 kDa Arg-specific proteinase

| Compound | Concentration (mM) | Activity (%) |
| --- | --- | --- |
| Leupeptin† | 0.1 | 0 |
| EDTA† | 1.0 | 100 |
| | 10.0 | 4 |
| | 50.0 | 0 |
| $+Ca^{2+}$ | 50.0 | 97 |
| o-phenanthroline† | 10.0 | 100 |

Figure 8A:
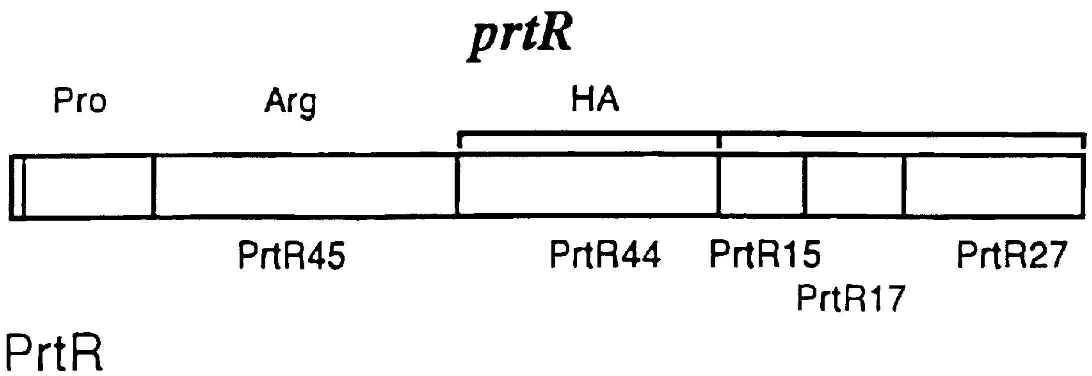
FIG. 8*a*. Schematic representation of the prtR gene. The PrtR nascent polyprotein is composed of a leader sequence, a prosequence followed by the Arg-specific cysteine proteinase PrtR45 (SEQ ID NO: 2, residues 1–16), and the adhesins PrtR44 (SEQ ID NO: 3, residues 1–16), PrtR15 (SEQ ID NO: 6, residues 1–16), PrtR17 (SEQ ID NO: 4, residues 1–16) and PrtR27 (SEQ ID NO: 5, residues 1–16) all preceded by an arginyl or lysyl residue.

*PCMB, p-chloromercuribenzoic acid; PMSF, phenylmethyl sulfonyl fluoride, AEBSF, [4-(2-aminoethyl)-benzenesulfonylfluoride]
†These incubations also contained 1.0 mM 2-mercaptoethanol The 45, 27, 17, 15 kDa and one of the 44 kDa protein components of the 300 kDa complex are encoded by the gene the PrtR as presented schematically in FIG. 8*a*. The complete nucleotide sequence and deduced amino acid sequence of the PrtR is shown in FIG. 8*b*. Each PrtR component is preceded by an arginyl or lysyl residue (FIGS. 8*a, b*) indicating that the polyprotein is processed by trypsin-like proteolytic specificity. We have designated these component parts of the 300 kDa complex, by their relative molecular masses as determined by SDS-PAGE, as the PrtR45, PrtR44, PrtR27, PrtR17 and PrtR15 which fit well with the predicted sizes from the deduced PrtR amino acid sequence (53.9, 44.8, 29.5, 17.5 and 14.3 kDa respectively). The 44 kDa protein, the PrtR44, has been disclosed by previous workers as a culture fluid hemagglutinin/adhesin (Pike et al., 1994)[J Biol Chem 269:406–411]. The PrtR44 has homology with the other non-proteinase components of the multiprotein complex suggesting a similar role for the PrtR27, PrtR17 and PrtR15 in interacting with the protease and/or in hemagglutination or adhesion. The PrtR45 Arg-specific endopeptidase component of the PrtR complex has the same characteristics and N-terminal sequence as the 50 kDa Arg-specific proteinase identified in the culture supernatant of *P. gingivalis* H66 by Chen et al. (1992)[J Biol Chem 267:18896–18901] designated Arg-gingipain.

Figure 9A:
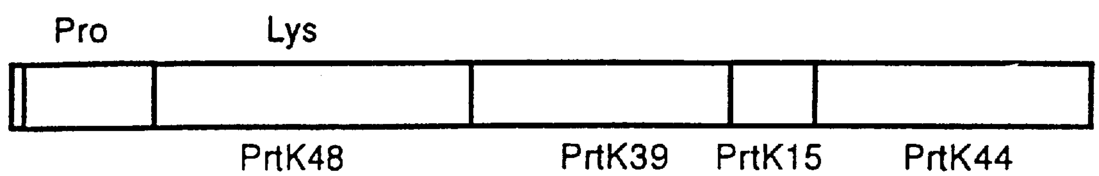
FIG. 9*a*. Schematic representation of the prtK gene. The PrtK nascent polyprotein is composed of a leader sequence, a prosequence followed by the Lys-specific cysteine proteinase PrtK48 (SEQ ID NO: 1), and the adhesins PrtK39 (SEQ ID NO: 5, residues 1–16), PrtK15 (SEQ ID NO: 6, residues 1–16), and PrtK44 (SEQ ID NO: 4, residues 1–16), all preceded by an arginyl or lysyl residue.

The other proteins of the 300 kDa complex, the 48 kDa Lys-specific proteinase, the other 44 kDa protein and the 39 kDa and 15 Da proteins are encoded by a single gene the prtK presented schematically in FIG. 9*a*. The complete nucleotide sequence and deduced amino acid sequence of the PrtK is shown in FIG. 9*b*. The prtK is similar to the prtR in that it encodes a putative leader sequence, a prosequence followed by the proteinase domain which is then followed by sequence-related adhesins that have high homology with the C-terminal adhesins of the prtR. We have designated the 48 kDa Lys-specific proteinase the PrtK48 and its associated adhesins the PrtK39, PrtK15 and PrtK44 (FIGS. 9*a, b*) based on the sizes measured by SDS-PAGE which fit reasonably well with the predicted sizes from the deduced PrtK amino acid sequence (55.9, 44.8, 14.3 and 47.9 kDa respectively). The PrtK48 has the same enzyme characteristics as the 48 kDa proteinase purified from the culture supernatant of *P. gingivalis* 33277 by Fujimura et al. (1993) [Infect Immun 55:716–720]. The PrtK48 also has the same N-terminal sequence and enzyme characteristics as the 60 kDa Lys-specific endopeptidase previously purified from the culture fluid of *P. gingivalis* H66 by Pike et al. (1994) [J Biol Chem 269:406–411] and designated Lys-gingipain. The PrtK39, PrtK15 and PrtK44 are all sequence-related and have high homology with the PrtR hemagglutinins/adhesins particularly the 15 kDa protein which is identical in both gene products suggesting that these proteins also are hemagglutinin/adhesins.

As the 300 kDa proteinase-adhesin complex and higher molecular mass forms are composed of proteins from the two genes, the prtR and prtK, we suggest that they be designated PrtR-PrtK complexes. The deduced molecular mass of the mature PrtR is 160 kDa (FIGS. 9*a, b*) and mature PrtK is 163 kDa (FIG. 9*b*) such that the mass of the PrtR-PrtK heterodimer would be 323 kDa which is in good agreement with the $M_r$ determined by gel filtration and non-boiling SDS-PAGE. SDS-PAGE of the sample after boiling produced the seven bands of 48, 45, 44, 39, 27, 17 and 15 kDa corresponding to the domains of the two gene products, the PrtR and PrtK. These domains were only seen when the sample was boiled, with or without reducing agent, suggesting that the domains remain tightly non-covalently associated after proteolytic processing. The cell sonicate and the chromatographic fractions had minimal or no proteolytic activity in the absence of reducing agents thus ensuring minimal enzymic activity during the chromatographic purifications. The characterization of the 300 kDa cell-associated complex as being composed of processed domains of the two genes the prtR and prtK suggests that the secreted, mature PrtR and PrtK proteins associate and then are processed, perhaps autolytically. The identification of several of the domains of the PrtR and PrtK in the culture supernatant by independent groups is consistent with the proteolytic (autolytic) processing of these polyproteins.

The relative molecular mass of the processed PrtR-PrtK complex is likely to be attributable to the composition of 1 PrtK48+1 PrtR45+1 PrtR44+1 PrtK39+1 PrtK44+1 PrtR27+1 PrtR17+1 PrtK15+1 PrtR15=294–323 kDa depending on C-terminal truncation, that is the 300 kDa complex would contain the five domains of the prtR and the four domains of the prtK gene products (FIGS. 8 and 9). As high $M_r$ material ($0.6\rightarrow 2\times 10^6$ Da) on gel filtration (FIG. 2) was also composed of the seven PrtR-PrtK bands then this suggests that the 300 kDa PrtR-PrtK complexes may further associate to form larger cell-associated aggregates. The high amino acid sequence homology between the PrtR44, PrtK39, PrtK44, PrtR27, PrtR17 and the 15 kDa protein of both the PrtR and PrtK suggests that these adhesins are responsible for the non-covalent cohesive interactions between the components of the PrtR-PrtK complexes and between the complexes themselves in the larger aggregates. It is interesting to note that some dissociation of the 300 kDa PrtR-PrtK complex occurred during the affinity chromatography on Arg-sepharose, although the majority of the protein eluted as the undissociated complex with 750 mM lysine. The partial dissociation of the complex on binding to substrate may be a mechanism by which the complex targets specific host macromolecules and cells releasing the proteinase/adhesin domains at the target site on binding.

This example describes the purification of a novel cell associated complex of Arg-specific and Lys-specific proteinases and sequence-related adhesins encoded by the two genes, the prtR and prtK.

B. Ultrafiltration and Diafiltration

Figure 10:
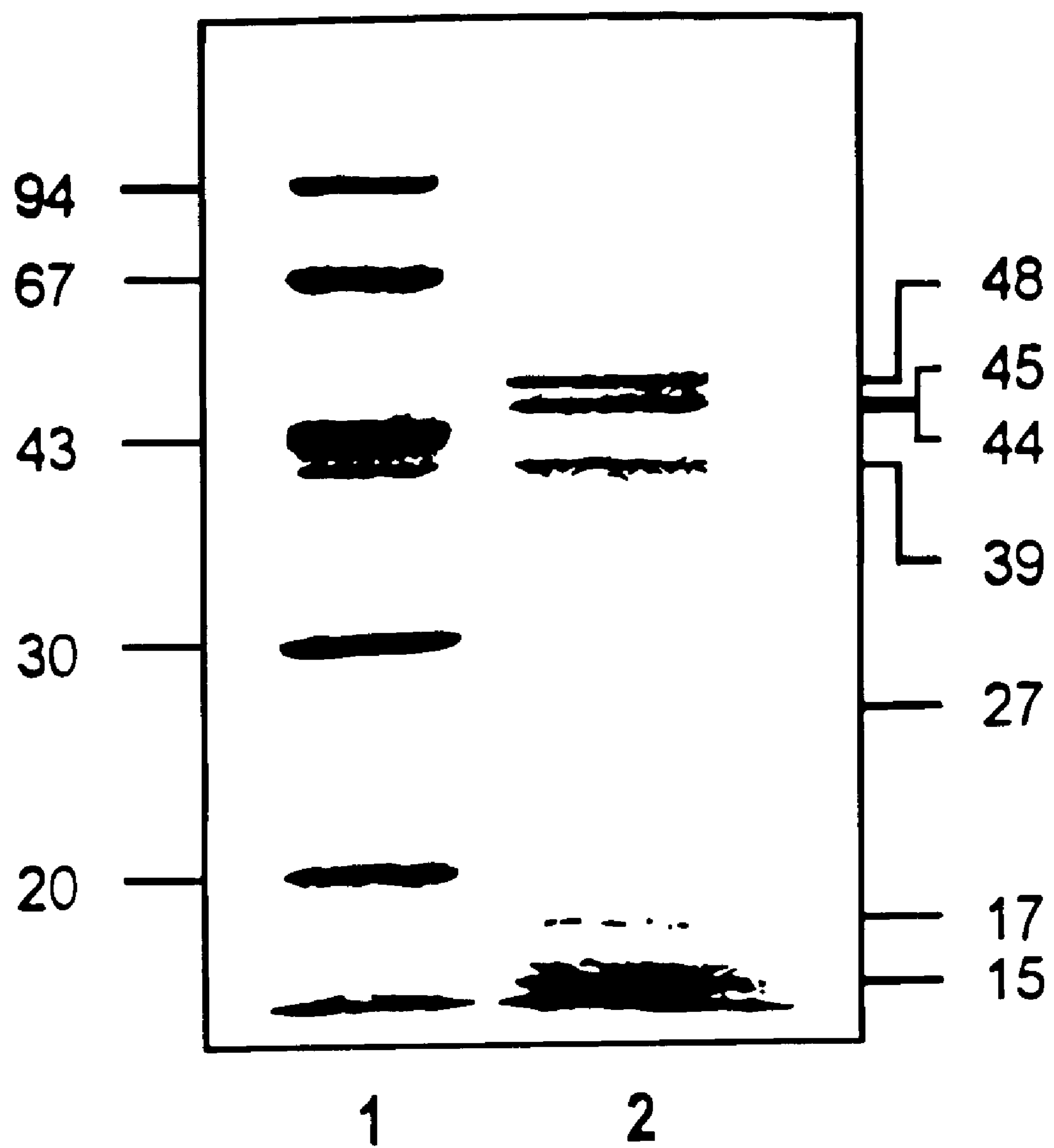
FIG. 10. SDS-PAGE of the PrtR-PrtK complex purified by diafiltration. Lane 1 shows molecular mass markers. Lane 2 shows components of the PrtR-PrtK purified by diafiltration.

*P. gingivalis* W50 was grown anaerobically at 37° C. on lysed horse blood agar and in modified BM media containing 1 $\mu$/ml hemin. Bacteria were maintained on lysed horse blood plates by routine passage (<10 passages) and used to inoculate batch cultures. Batch culture growth in Brain Heart Infusion medium was monitored at 650 nm using a spectrophotometer (295E, Perkin-Elmer). Culture purity was checked routinely by Gram stain, microscopic examination and by using a variety of biochemical tests. Stocks were maintained as lyophilised cultures. A culture of *P. gingivalis* was grown to late logarithmic phase and the cells harvested by centrifugation (5,000×g, 20 min, 4° C.). Chloroform was added to the cell pellet and after gentle mixing the suspension was left for 15 min at room temperature. Following chloroform treatment, 20 mM Tris-HCl pH 8.0 buffer containing 50 mM NaCl was added and gently mixed. This mixture was then centrifuged (100,000×g, 30 min, 4° C.) and the supernatant diafiltered through a 100,000 $M_r$ cut-off membrane (Amicon) with five volumes of distilled water. This purifies and inactivates by oxidation the 294≅323 kDa PrtR-PrtK which is freeze dried and used as an immunogen. The PrtR-PrtK purified by diafiltration was composed of 48, 45, 44, 39, 27 17 and 15 kDa components as shown by SDS-PAGE (FIG. 10).

(2) Preparation of Antibodies

Polyclonal antiserum to PrtR-PrtK was raised in a rabbit by immunizing with the $O_2$-inactivated PrtR-PrtK subcutaneously. The rabbit was immunized at day 0 with 40 μg of protein in incomplete Freund's adjuvant, day 14 with 90 μg of protein in incomplete Freund's adjuvant, and day 28 with 60 μg of protein in incomplete Freund's adjuvant. Immunizations were carried out using standard procedures. Polyclonal antisera having a high titre against *P. gingivalis* was obtained. If desired the antibodies directed specifically against *P. gingivalis* can be obtained using standard procedures.

EXAMPLE 2

Methods and compounds for vaccine formulations related to PrtR-PrtK.

This embodiment of the present invention is to provide PrtR-PrtK protein to be used in as an immunogen in a prophylactic and/or therapeutic vaccine for active immunization to protect against or treat infections caused by *P. gingivalis*. For vaccine purposes, an antigen of *P. gingivalis* comprising a bacterial protein should be immunogenic, and induce functional antibodies directed to one or more surface-exposed epitopes on intact bacteria, wherein the epitope(s) are conserved amongst strains of *P. gingivalis*.

In one illustration of the PrtR-PrtK protein having the properties desirable of a vaccine antigen, the protein was purified from *P. gingivalis* using the method described herein in Example 1. Mice were immunized with the purified inactivated PrtR-PrtK protein (25 ug) with adjuvant (20 ug of QS21) two times at four week intervals. The purified PrtR-PrtK was inactivated by air oxidation. Blood from the immunized mice was drawn 32 days after the last immunization and the immune sera was pooled. The pooled immune sera was assayed against whole bacteria (*P. gingivalis* strain W50) by an enzyme linked immunosorbent assay (ELISA). For the whole cell ELISA, overnight cultures of bacteria were harvested by a swab and suspended in PBS to an absorbance of 0.1 at 600 nm. Aliquots (100 ul) of the bacterial suspension were added to the wells of a 96 well microtiter plate and dried overnight at room temperature. The plates were blocked with 100 ul of 0.1% (w/v) gelatin in PBS. This, and all remaining incubations, were for one hour at room temperature unless otherwise specified. The blocking solution was removed and 100 ul of the immune sera, diluted in PBS with 0.1% (w/v) gelatin, was added to the wells and incubated. After washing three times with PBS, the bound antibodies were detected by incubating with 100 ul of alkaline phosphatase conjugated recombinant protein G (1:1500 in PBS with 0.1% (w/v) gelatin). The plates were washed and colour development was facilitated by the addition of 100 ul/well of p-nitrophenyl phosphate (2 mg/ml in diethanolamine). After 30 minutes, the reaction was stopped by adding 50 ul of 3M NaOH. The absorbance was read at 492 nm using an ELISA reader. Endpoint titers were determined as the reciprocal of the dilution at which the absorbance was greater than that of the blank wells. The results demonstrated that immunization with inactivated PrtR-PrtK elicit antibodies which can bind to one or more surface-exposed epitopes on intact *P. gingivalis*.

Additional evidence supporting the immunogenicity of the PrtR-PrtK protein comes from a study of the human immune response to the PrtR-PrtK of *P. gingivalis* in which 86% of 43 patients with adult periodontitis had specific IgG in their sera to the PrtR-PrtK.

Another illustration of a desirable vaccine antigen is the $O_2$-inactivated PrtR-PrtK. It has been demonstrated that the cell surface PrtR-PrtK is the target of bactericidal antibody generated from immunization with the inactivated protein. Polyclonal antiserum to PrtR-PrtK was raised in a rabbit by immunizing with the inactivated PrtR-PrtK subcutaneously. A rabbit was immunized at day 0 with 40 μg of protein in incomplete Freund's adjuvant, day 14 with 90 μg of protein in incomplete Freund's adjuvant, and day 28 with 60 μg of protein in incomplete Freund's adjuvant. The resultant antiserum was tested for its bactericidal activity against strain W50 of *P. gingivalis*. The bacteria were grown to logarithmic phase in brain-heart infusion (BHI) broth. An aliquot of the bacterial culture was diluted to $5\times10^4$ colony forming units (CFU) per ml in 10% bovine serum albumin in a balanced salt solution. The bactericidal assay reaction contained bacteria, polyclonal antiserum to inactivated PrtR-PrtK protein, a complement source consisting of normal human serum which was absorbed with protein G to remove antibodies, and the balanced salt solution. All reagents were added to the reaction to yield a 250 μl volume. Aliquots of 25 μl of the reaction were removed and plated in triplicate on BHI agar at times 0 and 60 minutes. The plates were incubated and colonies were counted the next day. The percent killing was calculated using the average of the three triplicate values at the 2 times. A representative example of data generated by the bactericidal assays is shown in Table 4. The results indicate that the polyclonal antiserum raised to the inactivated PrtR-PrtK is bactericidal for *P. gingivalis*. As illustrated by Table 4, controls show that the antiserum does not kill bacteria in the absence of complement, and that the complement source does not kill the bacteria in the absence of the antiserum, indicating that the bactericidal activity is antibody directed and complement mediated.

TABLE 4

Bactericidal activity of anti-(PrtR-PrtK) antibody

| Sample | Antiserum | Complement | CFU at time 0 | CFU at time 60 | Percent killing |
|---|---|---|---|---|---|
| 1 | 10 μl | 22 μl | 225 | 0 | 100% |
| 2 | 10 μl | 0 | 227 | 390 | 0% |
| 3 | 0 | 22 μl | 254 | 286 | 0% |

In further illustrating that the PrtR-PrtK protein possesses properties desirable of a vaccine antigen, pooled immune sera raised to strain W50 was shown to have cross-reactivity with heterologous strains. The pooled immune sera, prepared against PrtR-PrtK protein as described above, was examined for cross-reactivity with nine *P. gingivalis* strains from diverse clinical and geographical sources. Bacteria from each culture were harvested by swabs and suspended in PBS to an optical absorbance of 1.0 at 600nm. A microliter of each suspension was applied to a nitrocellulose membrane and allowed to dry. The membrane was incubated one hour at room temperature in a solution of 5% non-fat dry milk in PBS to block the residual binding sites of the membrane. The membrane was washed twice with PBS, and then immersed in the blocking solution containing the immune sera diluted to 1:1000. The membrane was incubated with the antibody overnight at 46° C. with gentle shaking. The membrane was washed three times with PBS and then incubated for 2 hours at room temperature with alkaline phosphatase conjugated recombinant protein G (1:1500 in PBS with 5% non-fat dry milk). The membrane was washed three times with PBS and bound antibody was detected by the addition of substrate. The immune sera reacted with all strains as strongly, or to a greater extent than, strain W50. Thus, the antibodies elicited by immunization of the PrtR-PrtK protein isolated from strain W50 cross-reacted with all heterologous strains tested.

For vaccine development, PrtR-PrtK may be purified from a host containing a recombinant vector which expresses PrtR-PrtK. Such hosts include, but are not limited to, bacterial transformants, yeast transformants, filamentous fungal transformants, and cultured cells that have been either infected or transfected with a vector which encodes PrtR-PrtK. Many methods are known for the introduction of a vaccine formulation into the human or animal to be vaccinated. These include, but are not limited to, intradermal, intramuscular, intraperitoneal, intravenous, subcutaneous, ocular, intranasal, and oral administration. The vaccine may further comprise a physiological carrier such as a solution, a polymer or liposomes; and an adjuvant, or a combination thereof.

EXAMPLE 3

Protective Efficacy of Immunisation with the PrtR-PrtK Complex in an Animal Model Various preparations of purified *P. gingivalis* proteins were tested in the mouse abscess model. This model is loosely based on the methods described by Kesavalu et al (1992) [Infect Immun 60:1455–1464]. A typical experiment is outlined below. Briefly BALB/c mice were obtained from ARC (Perth, Australia) and were immunised subcutaneously in the scruff of the neck with the preparations and doses according to Table 5 before challenge with live *P. gingivalis* strain W50, which was given at 10 weeks of age. Mice were given 2 doses of vaccine at 4 and 1 weeks before challenge. Formalin killed *P. gingivalis* W50 cells were prepared by incubating an aliquot of cells in 0.5% (vol/vol) of buffered formal saline overnight at 4° C. The chloroform extract of *P. gingivalis* was prepared as detailed in Example 2. Purification of PrtR-PrtK complex was performed as detailed in Example 1. The PrtR-PrtK domains were prepared by taking the PrtR-PrtK complex and incubating in the presence of 50 mM 2-mercaptoethanol for 8 h at 4° C. This resulted in the breakdown of the PrtR-PrtK complex to domains that were 15–115 kDa proteins as shown by gel filtration FPLC and SDS-PAGE as performed in Example 1.

All preparations were emulsified with an equal volume of Freund's Incomplete Adjuvant (FIA; Sigma) prior to injection.

Figure 11:
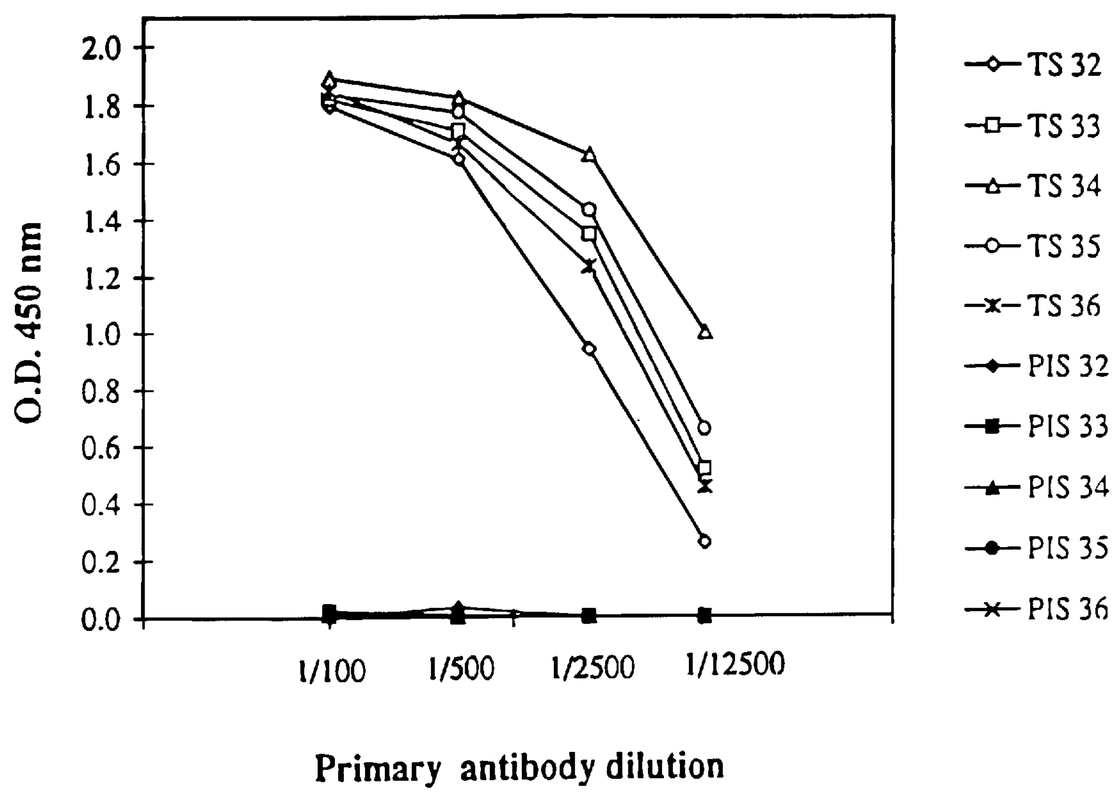
FIG. 11. ELISA titration of sera from 5 mice immunized twice with the PrtR-PrtK complex emulsified in Freund's Incomplete Adjuvant. Test sera (TS 32–36) and pre-immune sera (PIS 32–36) were screened using *P. gingivalis* W50 sonicate as the adsorbed antigen. Primary antibody dilutions of 1/100, 1/500, 1/2500 and 1/12500 were used. Bound antibody was determined using horseradish peroxidase-conjugated goat anti-mouse antibody and 3,3',5,5' tetramethylbenezidine. The reaction product was quantitated spectrophotometrically using a 450 mn interference filter in a plate reader and recorded as optical density (O.D.) readings.

Animals were bled before and 1 week after the immunisation schedule. Sera were screened by ELISA using a *P. gingivalis* sonicate (prepared as in Example 1) as the adsorbed antigen. The immunogenicity of the purified PrtR-PrtK complex is shown in FIG. 11.

TABLE 5

Immunization schedule

| Group | No. of Doses | Treatment | n |
|---|---|---|---|
| 1 | 2 | $1 \times 10^9$ Formalin killed *P. gingivalis* cells in FIA[1] | 11 |
| 2 | 2 | Chloroform extracted *P. gingivalis* proteins in FIA | 10 |
| 3 | 2 | Affinity purified *P. gingivalis* PrtR-PrtK complex in FIA | 5 |
| 4 | 2 | PrtR-PrtK Domains in FIA | 10 |
| 5 | 2 | Tris-cysteine buffer in FIA | 10 |
| 6 | 2 | Tris-cysteine buffer | 10 |

[1]FIA = Freunds incomplete adjuvant

For the preparation of the bacterial challenge *P. gingivalis* cells were grown at 37° C. on lysed horse blood agar (HBA) plates until day 3 or 4 in an anaerobic chamber (Mark 3 Anaerobic Workstation, Don Whitley Scientific Limited; with an air mixture of 8% $H_2$, 12% $CO_2$, 80% $N_2$), then passaged into 20 ml of brain heart infusion broth (BHIB; Oxoid) supplemented with 0.5 g/L cysteine and 1 mg/L haemin for 24 hours in a standard incubator at 37° C. Finally, 3 ml of this culture was added to 400 ml of BHIB-cysteine media and incubated for approximately 15 hours in a standard incubator at 37° C., until the optical density at 650 nm reached 0.18. The cells were then pelleted by centrifugation at 10,000 g for 30 minutes using a JA10 rotor in a Beckman High Speed centrifuge and then resuspended to a final dilution of $3\times10^{10}$ cells per ml in BHIB-cysteine media according to previously established growth curves for the W50 strain used in these experiments. Mice were marked for identification, their backs and chests shaved to make measurement of lesions possible, then weighed prior to inoculation with the challenge dose at a single site in the middle of the back. A 0.1 ml dose was given representing a predicted challenge dose of $3\times10^9$ bacteria per mouse. The inoculum dose was confirmed by culturing various dilutions of the challenge dose on lysed HBA plates and examining the number of colonies 7 days later.

Following challenge mice were examined daily for the number and size of lesions on their body and their size estimated by measuring the approximate surface area in $mm^2$ involved. Previous experiments had shown that in unimmunized mice, lesions developed on the belly of the mice following inoculation of live bacteria into the back or side. Any distressed animals were culled. Observations were carried out over two weeks and a summary of one such experiment is summarised below in Table 6. In this experiment while a dose of $3\times10^9$ bacteria per mouse was the desired number of bacteria, after plating out of the inoculum it was calculated that each mouse actually received a challenge dose of $3.17\times10^9$ live *P. gingivalis* bacteria strain W50.

When mice were immunised with the various *P. gingivalis* fractions significant reductions ($p<0.05$) were seen in the size of the lesions with whole formalin killed *P. gingivalis* strain W50 cells (Group 1), the chloroform extracted proteins (Group 2) and the PrtR-PrtK complex (Group 3) when compared with the lesion size of the animals receiving FIA (Group 5) (Table 6). The PrtR-PrtK domains (Group 4) of the broken down PrtR-PrtK complex did not significantly reduce lesion size compared with the control (Group 5). These results clearly show that the complex works effectively as an immunogen whereas the PrtR-PrtK domains (15–115 kDa proteins) do not. The only group of animals that had a number of animals (40%) that exhibited no visible lesions at all was the PrtR-PrtK complex group (Group 3). All other groups, including formalin killed cells (Group 1), had all animals exhibiting visible lesions indicating that the PrtR-PrtK complex was a better immunogen than formalin killed cells.

TABLE 6

Immunisation with the PrtR-PrtK complex can protect mice from challenge with *P. gingivalis*

| | Lesion size | |
|---|---|---|
| Group | Mean maximum lesion size mm$^2$ | p* |
| 1 | 30.2 ± 28.4[†] | 0.0008 |
| 2 | 39.0 ± 33.2 | 0.009 |
| 3 | 30.0 ± 36.0 | 0.0028 |
| 4 | 88.3 ± 32.2 | NS |
| 5 | 86.8 ± 41.1 | — |
| 6 | 201.7 ± 125.8 | 0.012 |

*probability calculated by Mann Whitney rank sum test comparing Group 5 with other groups
[†]mean ± SD

EXAMPLE 4

Cloning and Sequence Analysis of the prtR and prtK Genes Bacterial Strains

*P. gingivalis* W50 was grown in modified BM medium supplemented with 1 μg/ml haemin in an atmosphere of 10% $CO_2$, 10% $H_2$ and 80% $N_2$ at 37° C. *Escherichia coli* JM109 and *Escherichia coli* LE392 were grown in LB medium at 37° C. *Escherichia coli* strains harbouring pUC18 plasmids were grown in LB medium supplemented with 100 μg/ml ampicillin at 37° C.

Genomic Library Construction

Chromosomal DNA was isolated from *P. gingivalis* W50 as described by Smith et al, [Oral Microbiol. Immunol. 4:47–51 (1989)] except that cells were pelleted from a 500 ml late-exponential culture. The genomic library was constructed from BamHI partially-digested W50 DNA which was partially-filled with dGTP and dATP and ligated into LambdaGEM®-12 XhoI half-site arms (Promega) and packaged using Packagene® (Promega).

prtR gene characterisation: The genomic library was screened using degenerate synthetic oligonucleotides derived from the N-terminal sequence information of the purified PrtR45. The oligonucleotide probes were based on the amino acid sequence YEGDIKD (antisense) and KDFVDWKNQ (sense) and were 5'end-labelled using $\gamma^{32}P$ ATP and T4 polynucleotide kinase. Approximately $1.5\times10^4$ phage were screened by lifting onto Nylon membrane filters and hybridised with radiolabeled oligonucleotides overnight in hybridisation buffer: 6×SSC (SSC is 15 mM sodium citrate, 150 mM NaCl pH 8.0), 0.25% SDS, 5×Denhardt's solution and 100 μg/ml salmon sperm DNA at 44° C. Filters were washed extensively in a solution of 5×SSC containing 0.01% SDS (w/v) at 44° C. Positively-hybridising plaques were purified. Standard protocols for end-labelling of oligonucleotides and screening procedures were essentially as described in Sambrook et al. (1989) [Molecular Cloning: A Laboratory Manual; 2nd ed., Cold Spring Harbour Laboratory Press]. Lambda clone four with an insert size of approximately 15 kb was selected and this fragment contained the entire prtR gene. The 15 kb fragment was cut with appropriate restriction enzymes and the fragments generated subcloned into pUC18. *Escherichia coli* JM109 was transformed with the recombinant plasmids using electroporation.

prtk gene characterisation: The 5' portion of the gene encoding PrtK was isolated from the same genomic library described above. The genomic library was screened using a degenerate synthetic oligonucleotide derived from the N-terminal sequence information of the purified PrtK48. The oligonucleotide probes were sense to the amino acid sequence DVYTDHGD and radiolabelled as described above. Hybridisation and washing conditions were as described above except that the temperature was 48° C. and the filters were washed extensively in a solution of 3×SSC containing 0.01% SDS (w/v) at 48° C. Lambda clone 12 with an insert size of approximately 15 kb was selected and digested with BamHI and a 3.3 kb fragment was ligated into plasmid BamHI-BAP pUC18 and *Escherichia coli* JM109 transformed with the recombinant plasmid as described previously. Due to an internal BamHI site within prtK, the 3.3 kb BamHI fragment contained the 5' portion of prtK which constituted the end of the lambda 12 clone. Sequence characterisation of the 3.3 kb BamHI fragment showed that the DNA sequence encoding PrtK48 contains an internal EcoRI site. Subsequently, a second oligonucleotide probe (lysir) specific to the sequence THIGAH which is found within the PrtK48 was generated to determine a suitable strategy for cloning the 3' end of prtK Southern blot analysis of genomic DNA indicated that a 7.5 kb EcoRI fragment contained the entire 3' portion of prtK. In order to characterise the 3' end of the prtK gene a second genomic library was prepared. EcoRI digested DNA fragments of 6–8 kb were purified from an agarose gel and subsequently ligated to EcoRI digested Lambda Zap II-calf intestinal phosphatase-treated vector (Stratagene). The genomic library enriched for 6–8 kb *P. gingivalis* EcoRI fragments was packaged using GigapackIII Gold packaging extract (Stratagene) according to the manufacturer's instructions. The library was screened as described previously, using oligonucleotide lysur except that hybridisation temperatures were 42° C. and filters were washed to 3×SSC containing 0.01% SDS (w/v) at 42° C. In vivo excision of the Lambda Zap II positive genomic clone was performed (Stratagene instruction manual) to excise the pBluescript phagemid which was subsequently sequenced to generate the sequence information corresponding to the 3' end of the prtK gene.

DNA Sequencing. Double-stranded plasmid template DNA prepared following the procedure of Li and Schweizer [Focus 15:19–20 (1993)] was sequenced in both directions using DNA sequence-derived, synthetic oligonucleotides, following the di-deoxy termination method [Proc. Natl. Acad. Sci. U.S.A. 74:5463–5467 (1977)], using the Sequenase version 2.0 nucleotide sequencing kit purchased from United States Biochemicals. Nucleotide and protein sequence data were analysed using programme suites accessed by the Australian National Genomic Information Service (ANGIS).

EXAMPLE 5

The following is an example of a proposed toothpaste formulation containing anti-(PrtR-PrtK) antibodies.

| Ingredient | % w/w |
|---|---|
| Dicalcium phosphate dihydrate | 50.0 |
| Glycerol | 20.0 |
| Sodium carboxymethyl cellulose | 1.0 |
| Sodium lauryl sulphate | 1.5 |
| Sodium lauroyl sarconisate | 0.5 |

-continued

| Ingredient | % w/w |
|---|---|
| Flavour | 1.0 |
| Sodium saccharin | 0.1 |
| Chlorhexidine gluconate | 0.01 |
| Dextranase | 0.01 |
| Goat serum containing anti-(PrtR-PrtK) | 0.2 |
| Water | balance |

EXAMPLE 6

The following is an example of a proposed toothpaste formulation

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Sodium lauryl sulphate | 1.5 |
| Sodium lauroyl sarconisate | 0.5 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine serum containing anti-(PtR-PrtK) | 0.2 |
| Water | balance |

EXAMPLE 7

The following is an example of a proposed toothpaste formulation.

| Ingredient | % w/w |
|---|---|
| Dicalcium phosphate dihydrate | 50.0 |
| Sorbitol | 10.0 |
| Glycerol | 10.0 |
| Sodium carboxymethyl cellulose | 1.0 |
| Lauroyl diethanolamide | 1.0 |
| Sucrose monolaurate | 2.0 |
| Flavour | 1.0 |
| Sodium saccharin | 0.1 |
| Sodium monofluorophosphate | 0.3 |
| Chlorhexidine gluconate | 0.01 |
| Dextranase | 0.01 |
| Bovine milk Ig containing anti-(PrtR-PrtK) | 0.1 |
| Water | balance |

EXAMPLE 8

The following is an example of a proposed toothpaste formulation.

| Ingredient | % w/w |
|---|---|
| Sorbitol | 22.0 |
| Irish moss | 1.0 |
| Sodium Hydroxide (50%) | 1.0 |
| Gantrez | 19.0 |
| Water (deionised) | 2.69 |
| Sodium Monofluorophosphate | 0.76 |
| Sodium saccharine | 0.3 |
| Pyrophosphate | 2.0 |
| Hydrated alumina | 48.0 |
| Flavour oil | 0.95 |
| anti-(PrtR-PrtK) mouse monoclonal | 0.3 |
| sodium lauryl sulphate | 2.00 |

EXAMPLE 9

The following is an example of a proposed liquid toothpaste formulation.

| Ingredient | % w/w |
|---|---|
| Sodium polyacrylate | 50.0 |
| Sorbitol | 10.0 |
| Glycerol | 20.0 |
| Flavour | 1.0 |
| Sodium saccharin | 0.1 |
| Sodium monofluorophosphate | 0.3 |
| Chlorhexidine gluconate | 0.01 |
| Ethanol | 3.0 |
| Equine Ig containing anti-(PrtR-PrtK) | 0.2 |
| Linolic acid | 0.05 |
| Water | balance |

EXAMPLE 10

The following is an example of a proposed mouthwash formulation.

| Ingredient | % w/w |
|---|---|
| Ethanol | 20.0 |
| Flavour | 1.0 |
| Sodium saccharin | 0.1 |
| Sodium monofluorophosphate | 0.3 |
| Chlorhexidine gluconate | 0.01 |
| Lauroyl diethanolamide | 0.3 |
| Rabbit Ig containing anti-(PrtR-PrtK) | 0.2 |
| Water | balance |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A purified antigenic complex for use in raising an antibody response directed against *Porphyromonas gingivalis,* the complex comprising at least one multimeric protein complex of arginine-specific and lysine-specific thiol endopeptidases each containing at least one adhesion domain, the complex having a molecular weight of about 294 to about 323 kDa wherein the multimeric protein complex comprises 9 proteins, the 9 proteins having the following N-terminal sequences:

DVYTDHGDLYNTPVRML (SEQ ID NO:1),

YTPVEEKQNGRMIVIVAKKYEGD (SEQ ID NO:2),

SGQAEIVLEAHDVWNDGSGYQILLDADHDQYGQVIPSDTHFL (SEQ ID NO:3),

PQSVWIERTVDLPAGTKYVAFR (SEQ ID NO:4),

ANEAKVVLAADNVWGNTGYQFLLDA (SEQ ID NO:5),

ANEAKVVLAADNVWGDNTGYQFLLDA SEQ ID NO:5),

PQSVWIERTVDLPAGTKYVAFR (SEQ ID NO:4),

ADFTETFESSTHGEAPAEWTTIDA (SEQ ID NO:6), and

ADFTETFESSTHGEAPAEWTTIDA (SEQ ID NO:6).

2. A purified antigenic complex as claimed in claim 1 in which the multimeric protein complex is associated with virulent strains of *Porphyromonas gingivalis.*

3. A purified antigenic complex as claimed in claim 1 in which the 9 proteins are PrtK48, PrtR45, PrtR44, PrtK39, PrtK44, PrtR27, PrtR17, PrtK15 and PrtR15.

4. A purified antigenic complex as claimed in claim 1 in which the thiol endopeptidases are rendered inactive.

5. A purified antigenic complex as claimed in claim 4 in which the thiol endopeptidases are rendered inactive by oxidation.

6. A purified antigenic complex as claimed in claim 4 in which the thiol endopeptidases are rendered inactive by mutation.

7. A purified antigenic complex as claimed in claim 1 in which the multimeric protein complex is encoded by the DNA sequence shown in FIGS. 8B (SEQ ID NO:7) and 9B (SEQ ID NO.: 8).

8. A composition for use in eliciting an immune response directed against *Porphyromonas gingivalis,* the composition comprising an effective amount of the complex as claimed in claim 1 and a suitable adjuvant and/or acceptable carrier.

9. A method of reducing the prospect of *P. gingivalis* infection in an individual and/or severity of disease, the method comprising administering to the individual an amount of the composition as claimed in claim 8 effective to induce an immune response in the individual directed against *P. gingivalis.*

* * * * *

SEQUENCE LISTING

<160> NUMBER OF SEQ ID NOS: 15

<210> SEQ ID NO 1
<211> LENGTH: 17
<212> TYPE: PRT
<213> ORGANISM: Organism: Porphyromonas gingivalis

<400> SEQUENCE: 1

Asp Val Tyr Thr Asp His Gly Asp Leu Tyr Asn Thr Pro Val Arg Met
1 5 10 15

Leu

<210> SEQ ID NO 2
<211> LENGTH: 23
<212> TYPE: PRT
<213> ORGANISM: Porphyromonas gingivalis

<400> SEQUENCE: 2

Tyr Thr Pro Val Glu Glu Lys Gln Asn Gly Arg Met Ile Val Ile Val
1 5 10 15

Ala Lys Lys Tyr Glu Gly Asp
20

<210> SEQ ID NO 3
<211> LENGTH: 42
<212> TYPE: PRT
<213> ORGANISM: Porphyromonas gingivalis

<400> SEQUENCE: 3

Ser Gly Gln Ala Glu Ile Val Leu Glu Ala His Asp Val Trp Asn Asp
1 5 10 15

Gly Ser Gly Tyr Gln Ile Leu Leu Asp Ala Asp His Asp Gln Tyr Gly
20 25 30

Gln Val Ile Pro Ser Asp Thr His Phe Leu
35 40

<210> SEQ ID NO 4
<211> LENGTH: 22
<212> TYPE: PRT
<213> ORGANISM: Porphyromonas gingivalis

<400> SEQUENCE: 4

Pro Gln Ser Val Trp Ile Glu Arg Thr Val Asp Leu Pro Ala Gly Thr
1 5 10 15

Lys Tyr Val Ala Phe Arg
20

<210> SEQ ID NO 5
<211> LENGTH: 26
<212> TYPE: PRT
<213> ORGANISM: Porphyromonas gingivalis

<400> SEQUENCE: 5

Ala Asn Glu Ala Lys Val Val Leu Ala Ala Asp Asn Val Trp Gly Asp
1 5 10 15

Asn Thr Gly Tyr Gln Phe Leu Leu Asp Ala
20 25

<210> SEQ ID NO 6
<211> LENGTH: 24

-continued

<212> TYPE: PRT
<213> ORGANISM: Porphyromonas gingivalis

<400> SEQUENCE: 6

Ala Asp Phe Thr Glu Thr Phe Glu Ser Ser Thr His Gly Glu Ala Pro
1 5 10 15

Ala Glu Trp Thr Thr Ile Asp Ala
20

<210> SEQ ID NO 7
<211> LENGTH: 5280
<212> TYPE: DNA
<213> ORGANISM: Porphyromonas gingivalis

<400> SEQUENCE: 7
gaattttgtc tcccaagaag actttataat gcataaatac agaaggggta ctacacagta 60
aaatcatatt ctaatttcat caaaatgaaa aacttgaaca agtttgtttc gattgctctt 120
tgctcttcct tattaggagg aatggcattt gcgcagcaga cagagttggg acgcaatccg 180
aatgtgagat tgctcgaatc cactcagcaa tcggtgacaa aggttcagtt ccgtatggac 240
aacctcaagt tcaccgaagt tcaaacccct aagggaatcg gacaagtgcc gacctataca 300
gaaggggtta atctttctga aaaagggatg cctacgcttc ccattctatc acgctctttg 360
gcggtttcag acactcgtga gatgaaggta gaggttgttt cctcaaagtt catcgaaaag 420
aaaaatgtcc tgattgcacc ctccaagggc atgattatgc gtaacgaaga tccgaaaaag 480
atcccttacg tttatggaaa gacgtactcg caaaacaaat tcttcccggg agagatcgcc 540
acgcttgatg atccttttat ccttcgtgat gtgcgtggac aggttgtaaa ctttgcgcct 600
ttgcagtata accctgtgac aaagacgttg cgcatctata cggaaatcac tgtggcagtg 660
agcgaaactt cggaacaagg caaaaatatt ctgaacaaga aaggtacatt tgccggcttt 720
gaagacacat acaagcgcat gttcatgaac tacgagccag ggcgttacac accggtagag 780
gaaaaacaaa atggtcgtat gatcgtcatc gtagccaaaa agtatgaggg agatattaaa 840
gatttcgttg attggaaaaa ccaacgcggt ctccgtaccg aggtgaaagt ggcagaagat 900
attgcttctc ccgttacagc taatgctatt cagcaattcg ttaagcaaga atacgagaaa 960
gaaggtaatg atttgaccta tgttcttttg attggcgatc acaaagatat tcctgccaaa 1020
attactccgg ggatcaaatc cgaccaggta tatggacaaa tagtaggtaa tgaccactac 1080
aacgaagtct tcatcggtcg tttctcatgt gagagcaaag aggatctgaa gacacaaatc 1140
gatcggacta ttcactatga gcgcaatata accacggaag acaaatggct cggtcaggct 1200
ctttgtattg cttcggctga aggaggccca tccgcagaca atggtgaaag tgatatccag 1260
catgagaatg taatcgccaa tctgcttacc cagtatggtt ataccaagat tatcaaatgt 1320
tatgatccgg gagtaactcc taaaaacatt attgatgctt tcaacggagg aatctcgttg 1380
gccaactata cgggccacgg tagcgaaaca gcttggggta cgtctcactt cggcaccact 1440
catgtgaagc agcttaccaa cagcaaccag ctaccgttta ttttcgacgt agcttgtgtg 1500
aatggcgatt tcctattcag catgccttgt ttcgcagaag cattgatgcg tgcacaaaaa 1560
gatggtaagc cgacaggtac tgttgctatc atagcgtcta cgatcaacca gtcttgggct 1620
tctcctatgc gcgggcagga tgagatgaac gaaattctgt gcgaaaaaca cccgaacaac 1680
atcaagcgta ctttcggtgg tgtcaccatg aacggtatgt ttgctatggt ggaaaagtat 1740
aaaaaggatg gtgagaagat gctcgacaca tggactgtat tcggcgaccc ctcgctgctc 1800

-continued

```
gttcgtacac ttgtcccgac caaaatgcag gttacggctc cggctcagat taatttgacg   1860
gatgcttcag tcaacgtatc ttgcgattat aatggtgcta ttgctaccat ttcagccaat   1920
ggaaagatgt tcggttctgc agttgtcgaa aatggaacag ctacaatcaa tctgacaggt   1980
ctgacaaatg aaagcacgct tacccttaca gtagttggtt acaacaaaga gacggttatt   2040
aagaccatca acactaatgg tgagcctaac ccctaccagc ctgtttccaa cttgactgct   2100
acaacgcagg gtcagaaagt aacgctcaag tgggatgcac cgagcacgaa aaccaatgca   2160
accactaata ccgctcgcag cgtggatggc atacgagaac tggttcttct gtcagtcagc   2220
gatgcccccg aacttcttcg cagcggtcag gccgagattg ttcttgaagc tcacgatgtt   2280
tggaatgatg gatccggtta tcagattctt ttggatgcag accatgatca atatggacag   2340
gttataccca gtgataccca tactctttgg ccgaactgta gtgtcccggc caatctgttc   2400
gctccgttcg aatatactgt tccggaaaat gcagatcctt cttgttcccc taccaatatg   2460
ataatggatg gtactgcatc cgttaatata ccggccggaa cttatgactt tgcaattgct   2520
gctcctcaag caaatgcaaa gatttggatt gccggacaag gaccgacgaa agaagatgat   2580
tatgtatttg aagccggtaa aaaataccat ttccttatga agaagatggg tagcggtgat   2640
ggaactgaat tgactataag cgaaggtggt ggaagcgatt acacctatac tgtctatcgt   2700
gacggcacga agatcaagga aggtctgacg gctacgacat tcgaagaaga cggtgtagct   2760
acgggcaatc atgagtattg cgtggaagtt aagtacacag ccggcgtatc tccgaaggta   2820
tgtaaagacg ttacggtaga aggatccaat gaatttgctc ctgtacagaa cctgaccggt   2880
agtgcagtcg gccagaaagt aacgcttaag tgggatgcac ctaatggtac cccgaatcca   2940
aatccaaatc cgaatccaaa tccgaatccc ggaacaacta cactttccga atcattcgaa   3000
aatggtattc ctgcctcatg gaagacgatc gatgcagacg gtgacgggca tggctggaag   3060
cctggaaatg ctcccggaat cgctggctac aatagcaatg gttgtgtata ttcagagtca   3120
ttcggtcttg gtggtatagg agttcttacc cctgacaact atctgataac accggcattg   3180
gatttgccta acggaggtaa gttgactttc tgggtatgcg cacaggatgc taattatgca   3240
tccgagcact atgcggtgta tgcatcttcg accggtaacg atgcatccaa cttcacgaat   3300
gctttgttgg aagagacgat tacggcaaaa ggtgttcgct cgccggaagc tatgcgtggt   3360
cgtatacagg gtacttggcg ccagaagacg gtagaccttc ccgcaggtac gaaatatgtt   3420
gctttccgtc acttccaaag caccgatatg ttctacatcg accttgatga ggttgagatc   3480
aaggccaatg gcaagcgcgc agacttcacg gaaacgttcg agtcttctac tcatggagag   3540
gcaccagcgg aatggactac tatcgatgcc gatggcgatg gtcagggttg gctctgtctg   3600
tcttccggac aattggactg gctgacagct catggcggca ccaacgtagt aagctctttc   3660
tcatggaatg gaatggcttt gaatcctgat aactatctca tctcaaagga tgttacaggc   3720
gcaacgaagg taaagtacta ctatgcagtc aacgacggtt ttcccgggga tcactatgcg   3780
gtgatgatct ccaagacggg cacgaacgcc ggagacttca cggttgtttt cgaagaaacg   3840
cctaacggaa taaataaggg cggagcaaga ttcggtcttt ccacggaagc cgatggcgcc   3900
aaacctcaaa gtgtatggat cgagcgtacg gtagatttgc ctgcgggcac gaagtatgtt   3960
gctttccgtc actacaattg ctcggatttg aactacattc ttttggatga tattcagttc   4020
accatgggtg gcagccccac cccgaccgat tatacctaca cggtgtatcg tgatggtacg   4080
aagatcaagg aaggtttgac cgaaacgacc ttcgaagaag acggcgtagc tacgggcaat   4140
catgagtatt gcgtggaagt gaagtacaca gccggcgtat ctccgaagaa atgtgtaaac   4200
```

-continued

```
gtaactgtta attcgacaca gttcaatcct gtaaagaacc tgaaggcaca accggatggc   4260
ggcgacgtgg ttctcaagtg ggaagccccg agcgcaaaga agacagaagg ttctcgtgaa   4320
gtaaaacgga tcggagacgg tcttttcgtt acgatcgaac ctgcaaacga tgtacgtgcc   4380
aacgaagcca aggttgtgct cgcagcagac aacgtatggg gagacaatac gggttaccag   4440
ttcttgttgg atgccgatca caatacattc ggaagtgtca ttccggcaac cggtcctctc   4500
tttaccggaa cagcttcttc cgatctttac agtgcgaact tcgagtcttt gatcccggcc   4560
aatgccgatc ctgttgttac tacacagaat attatcgtta caggacaggg tgaagttgta   4620
atccccggtg gtgtttacga ctattgcatt acgaacccgg aacctgcatc cggaaagatg   4680
tggatcgcag gagatggagg caaccagcct gcacgttatg acgatttcac attcgaagca   4740
ggcaagaagt acaccttcac gatgcgtcgc gccggaatgg gagatggaac tgatatggaa   4800
gtcgaagacg attcacctgc aagctatacc tatacagtct atcgtgacgg cacgaagatc   4860
aaggaaggtc tgaccgaaac gacctaccgc gatgcaggaa tgagtgcaca atctcatgag   4920
tattgcgtgg aagttaagta cacagccggc gtatctccga aggtttgtgt ggattatatt   4980
cctgacggag tggcagacgt aacggctcag aagccttaca cgctgacagt tgtaggaaag   5040
acgatcacgg taacttgcca aggcgaagct atgatctacg acatgaacgg tcgtcgtctg   5100
gcagccggtc gcaacacggt tgtttacacg gctcagggcg gctactatgc agttatggtt   5160
gtcgttgacg gcaagtctta cgtagagaaa ctcgctatca agtaaatctg tcttggactc   5220
ggagactttg tgcagacact tttaagatag gtctgtaatt gtctcagagt atgaatcggt   5280
```

<210> SEQ ID NO 8
<211> LENGTH: 6000
<212> TYPE: DNA
<213> ORGANISM: Porphyromonas gingivalis

<400> SEQUENCE: 8

```
ggatcctacg cccgataccc atactcgaag cctttgctca gtaccatcct gcagaaggtt     60
actctttcgc atatagtgac cctcttttct ctcagcataa tggtacctat catatcagta    120
aggggcgtat tgtcttttcg aacaatgtac agcccgagaa ctctttactt ccacatcaca    180
cccccgactc cttagtcaag gatctttttt cccctttccc ctccgctctc ttcctcatgc    240
tggactgact taaccttggt ctgctctact tttcggttgt aaatacatgc aacacaataa    300
ctttaattgt tgttagacaa cacttttaca agactctgac ttttaatgag gtggagcatg    360
aaccttttcc tctttcatct tctccttcag attacagtca atattttggc aaaaggctaa    420
ttgacagcct tttataaggg ttaatccctt gtcgcttata ttgaaaacat gttctttata    480
atccgatact cttcttaaat cgaatttttt ctctaaattg cgccgcaaca aaactccttg    540
agaaaagtac caatagaaat agaaggtagc attttgcctt taaattcctt ttcttttctt    600
ggattgttct tgaaatgaat cttatttgtg gatttttttt gttttttaa cccggccgtg    660
gttctctgaa tcacgaccat aaattgtttt aaagtatgag gaaattatta ttgctgatcg    720
cggcgtccct tttgggagtt ggtctttacg cccaaagcgc caagattaag cttgatgctc    780
cgactactcg aacgacatgt acgaacaata gcttcaagca gttcgatgca agcttttcgt    840
tcaatgaagt cgagctgaca aaggtggaga ccaaaggtgg tactttcgcc tcagtgtcaa    900
ttccgggtgc attcccgacc ggtgaggttg gttctcccga agtgccagca gttaggaagt    960
tgattgctgt gcctgtcgga gccacacctg ttgttcgcgt gaaaagtttt accgagcaag   1020
```

-continued

```
tttactctct gaaccaatac ggttccgaaa aactcatgcc acatcaaccc tctatgagca   1080
agagtgatga tcccgaaaag gttcccttcg tttacaatgc tgctgcttat gcacgcaaag   1140
gttttgtcgg acaagaactg acccaagtag aaatgttggg gacaatgcgt ggtgttcgca   1200
ttgcagctct taccattaat cctgttcagt atgatgtggt tgcaaaccaa ttgaaggtta   1260
gaaacaacat cgaaattgaa gtaagctttc aaggagctga tgaagtagct acacaacgtt   1320
tgtatgatgc ttcttttagc ccttatttcg aaacagctta taaacagctc ttcaatagag   1380
atgtttatac agatcatggc gacttgtata atacgccggt tcgtatgctt gttgttgcag   1440
gtgcaaaatt caaagaagct ctcaagcctt ggctcacttg gaaggctcaa aagggcttct   1500
atctggatgt gcattacaca gacgaagctg aagtaggaac gacaaacgcc tctatcaagg   1560
catttattca caagaaatac aatgatggat tggcagctag tgctgctccg gtcttcttgg   1620
ctttggttgg tgacactgac gttattagcg gagaaaaagg aaagaaaaca aaaaaagtta   1680
ccgacttgta ttacagtgca gtcgatggcg actatttccc tgaaatgtat actttccgta   1740
tgtctgcttc ttccccagaa gaactgacga acatcattga taaggtattg atgtatgaaa   1800
aggctactat gccagataag agttatttgg agaaagttct cttgattgca ggtgcagatt   1860
atagctggaa ttcccaggta ggtcagccaa ccattaaata cggtatgcag tactactaca   1920
accaagagca tggttatacc gacgtgtaca actatctcaa agccccttat acaggttgct   1980
acagtcattt gaataccgga gtcagctttg caaactatac agcgcatgga tctgagaccg   2040
catgggctga tccacttctg actacttctc aactgaaagc actcactaat aaggacaaat   2100
acttcttagc tattggcaac tgctgtatta cagctcaatt cgattatgta cagccttgct   2160
tcggagaggt aataactcgc gttaaggaga aaggggctta tgcctatatc ggttcatctc   2220
caaattctta ttggggcgag gactactatt ggagtgtggg tgctaatgcc gtatttggtg   2280
ttcagcctac ttttgaaggt acgtctatgg gttcttatga tgctacattc ttggaggatt   2340
cgtacaacac agtgaattct attatgtggg caggtaatct tgccgctact catgctggaa   2400
atatcggcaa tattacccat attggtgctc attactattg ggaagcttat catgtccttg   2460
gcgatggttc ggttatgcct tatcgtgcaa tgcctaagac caatacttat acgcttcctg   2520
cctctttgcc tcagaatcag gcttcttata gcattcaggc ttctgccggt tcttacgtag   2580
ctatttctaa agatggagtt ttgtatggaa caggtgttgc taatgccagc ggtgttgcga   2640
ctgtgagtat gactaagcag attacggaaa atggtaatta tgatgtagtt atcactcgct   2700
ctaattatct tcctgtgatc aagcaaattc aggtaggtga gcctagcccc taccagcccg   2760
tttccaactt gacagctaca acgcagggtc agaaagtaac gctcaagtgg gaagcaccga   2820
gcgcaaagaa ggcagaaggt tcccgtgaag taaaacggat cggagacggt cttttcgtta   2880
cgatcgaacc tgcaaacgat gtacgtgcca acgaagccaa ggttgtgctt gcggcagaca   2940
acgtatgggg agacaatacg ggttaccagt tcttgttgga tgccgatcac aatacattcg   3000
gaagtgtcat tccggcaacc ggtcctctct ttaccggaac agcttcttcc aatctttaca   3060
gtgcgaactt cgagtatttg atcccggcca atgccgatcc tgttgttact acacagaata   3120
ttatcgttac aggacagggt gaagttgtaa tccccggtgg tgtttacgac tattgcatta   3180
cgaacccgga acctgcatcc ggaaagatgt ggatcgcagg agatggaggc aaccagcctg   3240
cacgttatga cgatttcaca ttcgaagcag gcaagaagta caccttcacg atgcgtcgcg   3300
ccggaatggg agatggaact gatatggaag tcgaagacga ttcacctgca agctatacct   3360
acacggtgta tcgtgacggc acgaagatca aggaaggtct gacagctacg acattcgaag   3420
```

-continued

```
aagacggtgt agctgcaggc aatcatgagt attgcgtgga agttaagtac acagccggcg   3480
tatctccgaa ggtatgtaaa gacgttacgg tagaaggatc caatgaattt gctcctgtac   3540
agaacctgac cggtagttca gtaggtcaga aagtaacgct taagtgggat gcacctaatg   3600
gtaccccgaa tccgaatcca aatccgaatc cgaatccggg aacaacactt tccgaatcat   3660
tcgaaaatgg tattccggca tcttggaaga cgatcgatgc agacggtgac gggcatggct   3720
ggaaacctgg aaatgctccc ggaatcgctg gctacaatag caatggttgt gtatattcag   3780
agtcattcgg tcttggtggt ataggagttc ttacccctga caactatctg ataacaccgg   3840
cattggattt gcctaacgga ggtaagttga ctttctgggt atgcgcacag gatgctaatt   3900
atgcatccga gcactatgcg gtgtatgcat cttcgaccgg taacgatgca tccaacttca   3960
cgaatgcttt gttggaagag acgattacgg caaaaggtgt tcgctcgccg aaagctattc   4020
gtggtcgtat acagggtact tggcgccaga agacggtaga ccttcccgca ggtacgaaat   4080
atgttgcttt ccgtcacttc caaagcacgg atatgttcta catcgacctt gatgaggttg   4140
agatcaaggc caatggcaag cgcgcagact tcacggaaac gttcgagtct tctactcatg   4200
gagaggcacc agcggaatgg actactatcg atgccgatgg cgatggtcag ggttggctct   4260
gtctgtcttc cggacaattg gactggctga cagctcatgg cggcagcaac gtagtaagct   4320
ctttctcatg gaatggaatg gctttgaatc ctgataacta tctcatctca aaggatgtta   4380
caggcgcaac gaaggtaaag tactactatg cagtcaacga cggttttccc ggggatcact   4440
atgcggtgat gatctccaag acgggcacga acgccggaga cttcacggtt gttttcgaag   4500
aaacgcctaa cggaataaat aagggcggag caagattcgg tctttccacg gaagccaatg   4560
gcgccaaacc tcaaagtgta tggatcgagc gtacggtaga tttgcctgca ggcacgaagt   4620
atgttgcttt ccgtcactac aattgctcgg atttgaacta cattcttttg gatgatattc   4680
agttcaccat gggtggcagc ccccaccccga ccgattatac ctacacggtg tatcgtgatg   4740
gtacgaagat caaggaaggt ttgaccgaaa cgaccttcga agaagacggc gtagctacgg   4800
gcaatcatga gtattgcgtg gaagtgaagt acacagccgg cgtatctccg aagaaatgtg   4860
taaacgtaac tgttaattcg acacagttca atcctgtaca gaacctgacg gcagaacaag   4920
ctcctaacag catggatgca atccttaaat ggaatgcacc ggcatctaag cgtgcggaag   4980
ttctgaacga agacttcgaa aatggtattc ctgcctcatg gaagacgatc gatgcagacg   5040
gtgacggcaa caattggacg acgacccctc ctcccggagg ctcctctttt gcaggtcaca   5100
acagtgcgat ctgtgtctct tcagcttctt atatcaactt tgaaggtcct cagaaccctg   5160
ataactatct ggttacaccg gagctttctc ttcctggcgg aggaacgctt actttctggg   5220
tatgtgcaca agatgccaat tatgcatcag agcactatgc cgtgtacgca tcttctacgg   5280
gtaacgacgc ttccaacttc gccaacgctt tgttggaaga agtgctgacg gccaagacag   5340
ttgttacggc acctgaagcc attcgtggta ctcgtgctca gggcacctgg tatcaaaaga   5400
cggtacagtt gcctgcgggt actaagtatg ttgccttccg tcacttcggc tgtacggact   5460
tcttctggat caaccttgat gatgttgtaa tcacttcagg gaacgctccg tcttacacct   5520
atacgatcta tcgtaataat acacagatag catcaggcgt aacggagact acttaccgag   5580
atccggactt ggctaccggt ttttacacgt acggtgtaaa ggttgtttac ccgaacggag   5640
aatcagctat cgaaactgct acgttgaata tcacttcgtt ggcagacgta acggctcaga   5700
agccttacac gctgacagtt gtaggaaaga cgatcacggt aacttgccaa ggcgaagcta   5760
```

-continued

```
tgatctacga catgaacggt cgtcgtctgg cagcgggtcg caacacggtt gtttacacgg   5820

ctcagggcgg ccactatgca gtcatggttg tcgttgacgg caagtcttac gtagagaaac   5880

tcgctgtaaa gtaaatctgt cttggactcg gagactttgt gcagacactt ttaagatagg   5940

tctgtaattg tctcagagta tgaatcggtc gcccgacttc cttaaaagga ggtcgggcga   6000


<210> SEQ ID NO 9
<211> LENGTH: 199
<212> TYPE: PRT
<213> ORGANISM: Bos taurus

<400> SEQUENCE: 9

Arg Pro Lys His Pro Ile Lys His Gln Gly Leu Pro Gln Glu Val Leu
  1               5                  10                  15

Asn Glu Asn Leu Leu Arg Phe Phe Val Ala Pro Phe Pro Gln Val Phe
             20                  25                  30

Gly Lys Glu Lys Val Asn Glu Leu Ser Lys Asp Ile Gly Ser Glu Ser
         35                  40                  45

Thr Glu Asp Gln Ala Met Glu Asp Ile Lys Gln Met Glu Ala Glu Ser
     50                  55                  60

Ile Ser Ser Ser Glu Glu Ile Val Pro Asn Ser Val Glu Gln Lys His
 65                  70                  75                  80

Ile Gln Lys Glu Asp Val Pro Ser Glu Arg Tyr Leu Gly Tyr Leu Glu
                 85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195


<210> SEQ ID NO 10
<211> LENGTH: 1706
<212> TYPE: PRT
<213> ORGANISM: Porphyromonas gingivalis

<400> SEQUENCE: 10

Met Lys Asn Leu Asn Lys Phe Val Ser Ile Ala Leu Cys Ser Ser Leu
  1               5                  10                  15

Leu Gly Gly Met Ala Phe Ala Gln Gln Thr Glu Leu Gly Arg Asn Pro
             20                  25                  30

Asn Val Arg Leu Leu Glu Ser Thr Gln Gln Ser Val Thr Lys Val Gln
         35                  40                  45

Phe Arg Met Asp Asn Leu Lys Phe Thr Glu Val Gln Thr Pro Lys Gly
     50                  55                  60

Ile Gly Gln Val Pro Thr Tyr Thr Glu Gly Val Asn Leu Ser Glu Lys
 65                  70                  75                  80

Gly Met Pro Thr Leu Pro Ile Leu Ser Arg Ser Leu Ala Val Ser Asp
```

-continued

```
                 85                  90                  95

Thr Arg Glu Met Lys Val Glu Val Val Ser Ser Lys Phe Ile Glu Lys
            100                 105                 110

Lys Asn Val Leu Ile Ala Pro Ser Lys Gly Met Ile Met Arg Asn Glu
        115                 120                 125

Asp Pro Lys Lys Ile Pro Tyr Val Tyr Gly Lys Thr Tyr Ser Gln Asn
    130                 135                 140

Lys Phe Phe Pro Gly Glu Ile Ala Thr Leu Asp Asp Pro Phe Ile Leu
145                 150                 155                 160

Arg Asp Val Arg Gly Gln Val Val Asn Phe Ala Pro Leu Gln Tyr Asn
                165                 170                 175

Pro Val Thr Lys Thr Leu Arg Ile Tyr Thr Glu Ile Thr Val Ala Val
            180                 185                 190

Ser Glu Thr Ser Glu Gln Gly Lys Asn Ile Leu Asn Lys Lys Gly Thr
        195                 200                 205

Phe Ala Gly Phe Glu Asp Thr Tyr Lys Arg Met Phe Met Asn Tyr Glu
    210                 215                 220

Pro Gly Arg Tyr Thr Pro Val Glu Glu Lys Gln Asn Gly Arg Met Ile
225                 230                 235                 240

Val Ile Val Ala Lys Lys Tyr Glu Gly Asp Ile Lys Asp Phe Val Asp
                245                 250                 255

Trp Lys Asn Gln Arg Gly Leu Arg Thr Glu Val Lys Val Ala Glu Asp
            260                 265                 270

Ile Ala Ser Pro Val Thr Ala Asn Ala Ile Gln Gln Phe Val Lys Gln
        275                 280                 285

Glu Tyr Glu Lys Glu Gly Asn Asp Leu Thr Tyr Val Leu Leu Ile Gly
    290                 295                 300

Asp His Lys Asp Ile Pro Ala Lys Ile Thr Pro Gly Ile Lys Ser Asp
305                 310                 315                 320

Gln Val Tyr Gly Gln Ile Val Gly Asn Asp His Tyr Asn Glu Val Phe
                325                 330                 335

Ile Gly Arg Phe Ser Cys Glu Ser Lys Glu Asp Leu Lys Thr Gln Ile
            340                 345                 350

Asp Arg Thr Ile His Tyr Glu Arg Asn Ile Thr Thr Glu Asp Lys Trp
        355                 360                 365

Leu Gly Gln Ala Leu Cys Ile Ala Ser Ala Glu Gly Gly Pro Ser Ala
    370                 375                 380

Asp Asn Gly Glu Ser Asp Ile Gln His Glu Asn Val Ile Ala Asn Leu
385                 390                 395                 400

Leu Thr Gln Tyr Gly Tyr Thr Lys Ile Ile Lys Cys Tyr Asp Pro Gly
                405                 410                 415

Val Thr Pro Lys Asn Ile Ile Asp Ala Phe Asn Gly Gly Ile Ser Leu
            420                 425                 430

Ala Asn Tyr Thr Gly His Gly Ser Glu Thr Ala Trp Gly Thr Ser His
        435                 440                 445

Phe Gly Thr Thr His Val Lys Gln Leu Thr Asn Ser Asn Gln Leu Pro
    450                 455                 460

Phe Ile Phe Asp Val Ala Cys Val Asn Gly Asp Phe Leu Phe Ser Met
465                 470                 475                 480

Pro Cys Phe Ala Glu Ala Leu Met Arg Ala Gln Lys Asp Gly Lys Pro
                485                 490                 495

Thr Gly Thr Val Ala Ile Ile Ala Ser Thr Ile Asn Gln Ser Trp Ala
            500                 505                 510
```

-continued

```
Ser Pro Met Arg Gly Gln Asp Glu Met Asn Glu Ile Leu Cys Glu Lys
        515                 520                 525

His Pro Asn Asn Ile Lys Arg Thr Phe Gly Gly Val Thr Met Asn Gly
    530                 535                 540

Met Phe Ala Met Val Glu Lys Tyr Lys Lys Asp Gly Glu Lys Met Leu
545                 550                 555                 560

Asp Thr Trp Thr Val Phe Gly Asp Pro Ser Leu Leu Val Arg Thr Leu
                565                 570                 575

Val Pro Thr Lys Met Gln Val Thr Ala Pro Ala Gln Ile Asn Leu Thr
            580                 585                 590

Asp Ala Ser Val Asn Val Ser Cys Asp Tyr Asn Gly Ala Ile Ala Thr
        595                 600                 605

Ile Ser Ala Asn Gly Lys Met Phe Gly Ser Ala Val Val Glu Asn Gly
    610                 615                 620

Thr Ala Thr Ile Asn Leu Thr Gly Leu Thr Asn Glu Ser Thr Leu Thr
625                 630                 635                 640

Leu Thr Val Val Gly Tyr Asn Lys Glu Thr Val Ile Lys Thr Ile Asn
                645                 650                 655

Thr Asn Gly Glu Pro Asn Pro Tyr Gln Pro Val Ser Asn Leu Thr Ala
            660                 665                 670

Thr Thr Gln Gly Gln Lys Val Thr Leu Lys Trp Asp Ala Pro Ser Thr
        675                 680                 685

Lys Thr Asn Ala Thr Thr Asn Thr Ala Arg Ser Val Asp Gly Ile Arg
    690                 695                 700

Glu Leu Val Leu Leu Ser Val Ser Asp Ala Pro Glu Leu Leu Arg Ser
705                 710                 715                 720

Gly Gln Ala Glu Ile Val Leu Glu Ala His Asp Val Trp Asn Asp Gly
                725                 730                 735

Ser Gly Tyr Gln Ile Leu Leu Asp Ala Asp His Asp Gln Tyr Gly Gln
            740                 745                 750

Val Ile Pro Ser Asp Thr His Thr Leu Trp Pro Asn Cys Ser Val Pro
        755                 760                 765

Ala Asn Leu Phe Ala Pro Phe Glu Tyr Thr Val Pro Glu Asn Ala Asp
    770                 775                 780

Pro Ser Cys Ser Pro Thr Asn Met Ile Met Asp Gly Thr Ala Ser Val
785                 790                 795                 800

Asn Ile Pro Ala Gly Thr Tyr Asp Phe Ala Ile Ala Ala Pro Gln Ala
                805                 810                 815

Asn Ala Lys Ile Trp Ile Ala Gly Gln Gly Pro Thr Lys Glu Asp Asp
            820                 825                 830

Tyr Val Phe Glu Ala Gly Lys Lys Tyr His Phe Leu Met Lys Lys Met
        835                 840                 845

Gly Ser Gly Asp Gly Thr Glu Leu Thr Ile Ser Glu Gly Gly Gly Ser
    850                 855                 860

Asp Tyr Thr Tyr Thr Val Tyr Arg Asp Gly Thr Lys Ile Lys Glu Gly
865                 870                 875                 880

Leu Thr Ala Thr Thr Phe Glu Glu Asp Gly Val Ala Thr Gly Asn His
                885                 890                 895

Glu Tyr Cys Val Glu Val Lys Tyr Thr Ala Gly Val Ser Pro Lys Val
            900                 905                 910

Cys Lys Asp Val Thr Val Glu Gly Ser Asn Glu Phe Ala Pro Val Gln
        915                 920                 925
```

-continued

```
Asn Leu Thr Gly Ser Ala Val Gly Gln Lys Val Thr Leu Lys Trp Asp
    930                 935                 940

Ala Pro Asn Gly Thr Pro Asn Pro Asn Pro Asn Pro Asn Pro Asn Pro
945                 950                 955                 960

Asn Pro Gly Thr Thr Thr Leu Ser Glu Ser Phe Glu Asn Gly Ile Pro
                965                 970                 975

Ala Ser Trp Lys Thr Ile Asp Ala Asp Gly Asp Gly His Gly Trp Lys
            980                 985                 990

Pro Gly Asn Ala Pro Gly Ile Ala Gly Tyr Asn Ser Asn Gly Cys Val
        995                 1000                1005

Tyr Ser Glu Ser Phe Gly Leu Gly Gly Ile Gly Val Leu Thr Pro Asp
   1010                 1015                1020

Asn Tyr Leu Ile Thr Pro Ala Leu Asp Leu Pro Asn Gly Gly Lys Leu
1025                1030                1035                1040

Thr Phe Trp Val Cys Ala Gln Asp Ala Asn Tyr Ala Ser Glu His Tyr
               1045                1050                1055

Ala Val Tyr Ala Ser Ser Thr Gly Asn Asp Ala Ser Asn Phe Thr Asn
           1060                1065                1070

Ala Leu Leu Glu Glu Thr Ile Thr Ala Lys Gly Val Arg Ser Pro Glu
       1075                1080                1085

Ala Met Arg Gly Arg Ile Gln Gly Thr Trp Arg Gln Lys Thr Val Asp
   1090                1095                1100

Leu Pro Ala Gly Thr Lys Tyr Val Ala Phe Arg His Phe Gln Ser Thr
1105                1110                1115                1120

Asp Met Phe Tyr Ile Asp Leu Asp Glu Val Glu Ile Lys Ala Asn Gly
               1125                1130                1135

Lys Arg Ala Asp Phe Thr Glu Thr Phe Glu Ser Ser Thr His Gly Glu
           1140                1145                1150

Ala Pro Ala Glu Trp Thr Thr Ile Asp Ala Asp Gly Asp Gly Gln Gly
       1155                1160                1165

Trp Leu Cys Leu Ser Ser Gly Gln Leu Asp Trp Leu Thr Ala His Gly
   1170                1175                1180

Gly Thr Asn Val Val Ser Ser Phe Ser Trp Asn Gly Met Ala Leu Asn
1185                1190                1195                1200

Pro Asp Asn Tyr Leu Ile Ser Lys Asp Val Thr Gly Ala Thr Lys Val
               1205                1210                1215

Lys Tyr Tyr Tyr Ala Val Asn Asp Gly Phe Pro Gly Asp His Tyr Ala
           1220                1225                1230

Val Met Ile Ser Lys Thr Gly Thr Asn Ala Gly Asp Phe Thr Val Val
       1235                1240                1245

Phe Glu Glu Thr Pro Asn Gly Ile Asn Lys Gly Gly Ala Arg Phe Gly
   1250                1255                1260

Leu Ser Thr Glu Ala Asp Gly Ala Lys Pro Gln Ser Val Trp Ile Glu
1265                1270                1275                1280

Arg Thr Val Asp Leu Pro Ala Gly Thr Lys Tyr Val Ala Phe Arg His
               1285                1290                1295

Tyr Asn Cys Ser Asp Leu Asn Tyr Ile Leu Leu Asp Asp Ile Gln Phe
           1300                1305                1310

Thr Met Gly Gly Ser Pro Thr Pro Thr Asp Tyr Thr Tyr Thr Val Tyr
       1315                1320                1325

Arg Asp Gly Thr Lys Ile Lys Glu Gly Leu Thr Glu Thr Thr Phe Glu
   1330                1335                1340

Glu Asp Gly Val Ala Thr Gly Asn His Glu Tyr Cys Val Glu Val Lys
```

-continued

```
1345                1350                1355                1360

Tyr Thr Ala Gly Val Ser Pro Lys Lys Cys Val Asn Val Thr Val Asn
                1365                1370                1375

Ser Thr Gln Phe Asn Pro Val Lys Asn Leu Lys Ala Gln Pro Asp Gly
            1380                1385                1390

Gly Asp Val Val Leu Lys Trp Glu Ala Pro Ser Ala Lys Lys Thr Glu
        1395                1400                1405

Gly Ser Arg Glu Val Lys Arg Ile Gly Asp Gly Leu Phe Val Thr Ile
    1410                1415                1420

Glu Pro Ala Asn Asp Val Arg Ala Asn Glu Ala Lys Val Val Leu Ala
1425                1430                1435                1440

Ala Asp Asn Val Trp Gly Asp Asn Thr Gly Tyr Gln Phe Leu Leu Asp
                1445                1450                1455

Ala Asp His Asn Thr Phe Gly Ser Val Ile Pro Ala Thr Gly Pro Leu
            1460                1465                1470

Phe Thr Gly Thr Ala Ser Ser Asp Leu Tyr Ser Ala Asn Phe Glu Ser
        1475                1480                1485

Leu Ile Pro Ala Asn Ala Asp Pro Val Val Thr Thr Gln Asn Ile Ile
    1490                1495                1500

Val Thr Gly Gln Gly Glu Val Val Ile Pro Gly Gly Val Tyr Asp Tyr
1505                1510                1515                1520

Cys Ile Thr Asn Pro Glu Pro Ala Ser Gly Lys Met Trp Ile Ala Gly
                1525                1530                1535

Asp Gly Gly Asn Gln Pro Ala Arg Tyr Asp Asp Phe Thr Phe Glu Ala
            1540                1545                1550

Gly Lys Lys Tyr Thr Phe Thr Met Arg Arg Ala Gly Met Gly Asp Gly
        1555                1560                1565

Thr Asp Met Glu Val Glu Asp Asp Ser Pro Ala Ser Tyr Thr Tyr Thr
    1570                1575                1580

Val Tyr Arg Asp Gly Thr Lys Ile Lys Glu Gly Leu Thr Glu Thr Thr
1585                1590                1595                1600

Tyr Arg Asp Ala Gly Met Ser Ala Gln Ser His Glu Tyr Cys Val Glu
                1605                1610                1615

Val Lys Tyr Thr Ala Gly Val Ser Pro Lys Val Cys Val Asp Tyr Ile
            1620                1625                1630

Pro Asp Gly Val Ala Asp Val Thr Ala Gln Lys Pro Tyr Thr Leu Thr
        1635                1640                1645

Val Val Gly Lys Thr Ile Thr Val Thr Cys Gln Gly Glu Ala Met Ile
    1650                1655                1660

Tyr Asp Met Asn Gly Arg Arg Leu Ala Ala Gly Arg Asn Thr Val Val
1665                1670                1675                1680

Tyr Thr Ala Gln Gly Gly Tyr Tyr Ala Val Met Val Val Val Asp Gly
                1685                1690                1695

Lys Ser Tyr Val Glu Lys Leu Ala Ile Lys
            1700                1705


<210> SEQ ID NO 11
<211> LENGTH: 1732
<212> TYPE: PRT
<213> ORGANISM: Porphyromonas gingivalis

<400> SEQUENCE: 11

Met Arg Lys Leu Leu Leu Leu Ile Ala Ala Ser Leu Leu Gly Val Gly
  1               5                  10                  15
```

-continued

```
Leu Tyr Ala Gln Ser Ala Lys Ile Lys Leu Asp Ala Pro Thr Thr Arg
            20                  25                  30

Thr Thr Cys Thr Asn Asn Ser Phe Lys Gln Phe Asp Ala Ser Phe Ser
        35                  40                  45

Phe Asn Glu Val Glu Leu Thr Lys Val Glu Thr Lys Gly Gly Thr Phe
    50                  55                  60

Ala Ser Val Ser Ile Pro Gly Ala Phe Pro Thr Gly Glu Val Gly Ser
65                  70                  75                  80

Pro Glu Val Pro Ala Val Arg Lys Leu Ile Ala Val Pro Val Gly Ala
                85                  90                  95

Thr Pro Val Val Arg Val Lys Ser Phe Thr Glu Gln Val Tyr Ser Leu
            100                 105                 110

Asn Gln Tyr Gly Ser Glu Lys Leu Met Pro His Gln Pro Ser Met Ser
        115                 120                 125

Lys Ser Asp Asp Pro Glu Lys Val Pro Phe Val Tyr Asn Ala Ala Ala
    130                 135                 140

Tyr Ala Arg Lys Gly Phe Val Gly Gln Glu Leu Thr Gln Val Glu Met
145                 150                 155                 160

Leu Gly Thr Met Arg Gly Val Arg Ile Ala Ala Leu Thr Ile Asn Pro
                165                 170                 175

Val Gln Tyr Asp Val Val Ala Asn Gln Leu Lys Val Arg Asn Asn Ile
            180                 185                 190

Glu Ile Glu Val Ser Phe Gln Gly Ala Asp Glu Val Ala Thr Gln Arg
        195                 200                 205

Leu Tyr Asp Ala Ser Phe Ser Pro Tyr Phe Glu Thr Ala Tyr Lys Gln
    210                 215                 220

Leu Phe Asn Arg Asp Val Tyr Thr Asp His Gly Asp Leu Tyr Asn Thr
225                 230                 235                 240

Pro Val Arg Met Leu Val Val Ala Gly Ala Lys Phe Lys Glu Ala Leu
                245                 250                 255

Lys Pro Trp Leu Thr Trp Lys Ala Gln Lys Gly Phe Tyr Leu Asp Val
            260                 265                 270

His Tyr Thr Asp Glu Ala Glu Val Gly Thr Thr Asn Ala Ser Ile Lys
        275                 280                 285

Ala Phe Ile His Lys Lys Tyr Asn Asp Gly Leu Ala Ala Ser Ala Ala
    290                 295                 300

Pro Val Phe Leu Ala Leu Val Gly Asp Thr Asp Val Ile Ser Gly Glu
305                 310                 315                 320

Lys Gly Lys Lys Thr Lys Lys Val Thr Asp Leu Tyr Tyr Ser Ala Val
                325                 330                 335

Asp Gly Asp Tyr Phe Pro Glu Met Tyr Thr Phe Arg Met Ser Ala Ser
            340                 345                 350

Ser Pro Glu Glu Leu Thr Asn Ile Ile Asp Lys Val Leu Met Tyr Glu
        355                 360                 365

Lys Ala Thr Met Pro Asp Lys Ser Tyr Leu Glu Lys Val Leu Leu Ile
    370                 375                 380

Ala Gly Ala Asp Tyr Ser Trp Asn Ser Gln Val Gly Gln Pro Thr Ile
385                 390                 395                 400

Lys Tyr Gly Met Gln Tyr Tyr Tyr Asn Gln Glu His Gly Tyr Thr Asp
                405                 410                 415

Val Tyr Asn Tyr Leu Lys Ala Pro Tyr Thr Gly Cys Tyr Ser His Leu
            420                 425                 430

Asn Thr Gly Val Ser Phe Ala Asn Tyr Thr Ala His Gly Ser Glu Thr
```

-continued

```
        435                 440                 445

Ala Trp Ala Asp Pro Leu Leu Thr Thr Ser Gln Leu Lys Ala Leu Thr
    450                 455                 460

Asn Lys Asp Lys Tyr Phe Leu Ala Ile Gly Asn Cys Cys Ile Thr Ala
465                 470                 475                 480

Gln Phe Asp Tyr Val Gln Pro Cys Phe Gly Glu Val Ile Thr Arg Val
                485                 490                 495

Lys Glu Lys Gly Ala Tyr Ala Tyr Ile Gly Ser Ser Pro Asn Ser Tyr
            500                 505                 510

Trp Gly Glu Asp Tyr Tyr Trp Ser Val Gly Ala Asn Ala Val Phe Gly
        515                 520                 525

Val Gln Pro Thr Phe Glu Gly Thr Ser Met Gly Ser Tyr Asp Ala Thr
    530                 535                 540

Phe Leu Glu Asp Ser Tyr Asn Thr Val Asn Ser Ile Met Trp Ala Gly
545                 550                 555                 560

Asn Leu Ala Ala Thr His Ala Gly Asn Ile Gly Asn Ile Thr His Ile
                565                 570                 575

Gly Ala His Tyr Tyr Trp Glu Ala Tyr His Val Leu Gly Asp Gly Ser
            580                 585                 590

Val Met Pro Tyr Arg Ala Met Pro Lys Thr Asn Thr Tyr Thr Leu Pro
        595                 600                 605

Ala Ser Leu Pro Gln Asn Gln Ala Ser Tyr Ser Ile Gln Ala Ser Ala
    610                 615                 620

Gly Ser Tyr Val Ala Ile Ser Lys Asp Gly Val Leu Tyr Gly Thr Gly
625                 630                 635                 640

Val Ala Asn Ala Ser Gly Val Ala Thr Val Ser Met Thr Lys Gln Ile
                645                 650                 655

Thr Glu Asn Gly Asn Tyr Asp Val Val Ile Thr Arg Ser Asn Tyr Leu
            660                 665                 670

Pro Val Ile Lys Gln Ile Gln Val Gly Glu Pro Ser Pro Tyr Gln Pro
        675                 680                 685

Val Ser Asn Leu Thr Ala Thr Thr Gln Gly Gln Lys Val Thr Leu Lys
    690                 695                 700

Trp Glu Ala Pro Ser Ala Lys Lys Ala Glu Gly Ser Arg Glu Val Lys
705                 710                 715                 720

Arg Ile Gly Asp Gly Leu Phe Val Thr Ile Glu Pro Ala Asn Asp Val
                725                 730                 735

Arg Ala Asn Glu Ala Lys Val Val Leu Ala Ala Asp Asn Val Trp Gly
            740                 745                 750

Asp Asn Thr Gly Tyr Gln Phe Leu Leu Asp Ala Asp His Asn Thr Phe
        755                 760                 765

Gly Ser Val Ile Pro Ala Thr Gly Pro Leu Phe Thr Gly Thr Ala Ser
    770                 775                 780

Ser Asn Leu Tyr Ser Ala Asn Phe Glu Tyr Leu Ile Pro Ala Asn Ala
785                 790                 795                 800

Asp Pro Val Val Thr Thr Gln Asn Ile Ile Val Thr Gly Gln Gly Glu
                805                 810                 815

Val Val Ile Pro Gly Gly Val Tyr Asp Tyr Cys Ile Thr Asn Pro Glu
            820                 825                 830

Pro Ala Ser Gly Lys Met Trp Ile Ala Gly Asp Gly Gly Asn Gln Pro
        835                 840                 845

Ala Arg Tyr Asp Asp Phe Thr Phe Glu Ala Gly Lys Lys Tyr Thr Phe
    850                 855                 860
```

-continued

```
Thr Met Arg Arg Ala Gly Met Gly Asp Gly Thr Asp Met Glu Val Glu
865                 870                 875                 880

Asp Asp Ser Pro Ala Ser Tyr Thr Tyr Thr Val Tyr Arg Asp Gly Thr
                885                 890                 895

Lys Ile Lys Glu Gly Leu Thr Ala Thr Thr Phe Glu Glu Asp Gly Val
            900                 905                 910

Ala Ala Gly Asn His Glu Tyr Cys Val Glu Val Lys Tyr Thr Ala Gly
        915                 920                 925

Val Ser Pro Lys Val Cys Lys Asp Val Thr Val Glu Gly Ser Asn Glu
    930                 935                 940

Phe Ala Pro Val Gln Asn Leu Thr Gly Ser Ser Val Gly Gln Lys Val
945                 950                 955                 960

Thr Leu Lys Trp Asp Ala Pro Asn Gly Thr Pro Asn Pro Asn Pro Asn
                965                 970                 975

Pro Asn Pro Asn Pro Gly Thr Thr Leu Ser Glu Ser Phe Glu Asn Gly
            980                 985                 990

Ile Pro Ala Ser Trp Lys Thr Ile Asp Ala Asp Gly Asp Gly His Gly
        995                 1000                1005

Trp Lys Pro Gly Asn Ala Pro Gly Ile Ala Gly Tyr Asn Ser Asn Gly
   1010                1015                1020

Cys Val Tyr Ser Glu Ser Phe Gly Leu Gly Gly Ile Gly Val Leu Thr
1025               1030                1035                1040

Pro Asp Asn Tyr Leu Ile Thr Pro Ala Leu Asp Leu Pro Asn Gly Gly
               1045                1050                1055

Lys Leu Thr Phe Trp Val Cys Ala Gln Asp Ala Asn Tyr Ala Ser Glu
           1060                1065                1070

His Tyr Ala Val Tyr Ala Ser Ser Thr Gly Asn Asp Ala Ser Asn Phe
       1075                1080                1085

Thr Asn Ala Leu Leu Glu Glu Thr Ile Thr Ala Lys Gly Val Arg Ser
   1090                1095                1100

Pro Lys Ala Ile Arg Gly Arg Ile Gln Gly Thr Trp Arg Gln Lys Thr
1105               1110                1115                1120

Val Asp Leu Pro Ala Gly Thr Lys Tyr Val Ala Phe Arg His Phe Gln
               1125                1130                1135

Ser Thr Asp Met Phe Tyr Ile Asp Leu Asp Glu Val Glu Ile Lys Ala
           1140                1145                1150

Asn Gly Lys Arg Ala Asp Phe Thr Glu Thr Phe Glu Ser Ser Thr His
       1155                1160                1165

Gly Glu Ala Pro Ala Glu Trp Thr Thr Ile Asp Ala Asp Gly Asp Gly
   1170                1175                1180

Gln Gly Trp Leu Cys Leu Ser Ser Gly Gln Leu Asp Trp Leu Thr Ala
1185               1190                1195                1200

His Gly Gly Ser Asn Val Val Ser Ser Phe Ser Trp Asn Gly Met Ala
               1205                1210                1215

Leu Asn Pro Asp Asn Tyr Leu Ile Ser Lys Asp Val Thr Gly Ala Thr
           1220                1225                1230

Lys Val Lys Tyr Tyr Tyr Ala Val Asn Asp Gly Phe Pro Gly Asp His
       1235                1240                1245

Tyr Ala Val Met Ile Ser Lys Thr Gly Thr Asn Ala Gly Asp Phe Thr
   1250                1255                1260

Val Val Phe Glu Glu Thr Pro Asn Gly Ile Asn Lys Gly Gly Ala Arg
1265               1270                1275                1280
```

-continued

```
Phe Gly Leu Ser Thr Glu Ala Asn Gly Ala Lys Pro Gln Ser Val Trp
            1285                1290                1295

Ile Glu Arg Thr Val Asp Leu Pro Ala Gly Thr Lys Tyr Val Ala Phe
        1300                1305                1310

Arg His Tyr Asn Cys Ser Asp Leu Asn Tyr Ile Leu Leu Asp Asp Ile
    1315                1320                1325

Gln Phe Thr Met Gly Gly Ser Pro Thr Pro Thr Asp Tyr Thr Tyr Thr
   1330                1335                1340

Val Tyr Arg Asp Gly Thr Lys Ile Lys Glu Gly Leu Thr Glu Thr Thr
1345                1350                1355                1360

Phe Glu Glu Asp Gly Val Ala Thr Gly Asn His Glu Tyr Cys Val Glu
            1365                1370                1375

Val Lys Tyr Thr Ala Gly Val Ser Pro Lys Lys Cys Val Asn Val Thr
        1380                1385                1390

Val Asn Ser Thr Gln Phe Asn Pro Val Gln Asn Leu Thr Ala Glu Gln
    1395                1400                1405

Ala Pro Asn Ser Met Asp Ala Ile Leu Lys Trp Asn Ala Pro Ala Ser
   1410                1415                1420

Lys Arg Ala Glu Val Leu Asn Glu Asp Phe Glu Asn Gly Ile Pro Ala
1425                1430                1435                1440

Ser Trp Lys Thr Ile Asp Ala Asp Gly Asp Gly Asn Asn Trp Thr Thr
            1445                1450                1455

Thr Pro Pro Pro Gly Gly Ser Ser Phe Ala Gly His Asn Ser Ala Ile
        1460                1465                1470

Cys Val Ser Ser Ala Ser Tyr Ile Asn Phe Glu Gly Pro Gln Asn Pro
    1475                1480                1485

Asp Asn Tyr Leu Val Thr Pro Glu Leu Ser Leu Pro Gly Gly Gly Thr
   1490                1495                1500

Leu Thr Phe Trp Val Cys Ala Gln Asp Ala Asn Tyr Ala Ser Glu His
1505                1510                1515                1520

Tyr Ala Val Tyr Ala Ser Ser Thr Gly Asn Asp Ala Ser Asn Phe Ala
            1525                1530                1535

Asn Ala Leu Leu Glu Glu Val Leu Thr Ala Lys Thr Val Val Thr Ala
        1540                1545                1550

Pro Glu Ala Ile Arg Gly Thr Arg Ala Gln Gly Thr Trp Tyr Gln Lys
    1555                1560                1565

Thr Val Gln Leu Pro Ala Gly Thr Lys Tyr Val Ala Phe Arg His Phe
   1570                1575                1580

Gly Cys Thr Asp Phe Phe Trp Ile Asn Leu Asp Asp Val Val Ile Thr
1585                1590                1595                1600

Ser Gly Asn Ala Pro Ser Tyr Thr Tyr Thr Ile Tyr Arg Asn Asn Thr
            1605                1610                1615

Gln Ile Ala Ser Gly Val Thr Glu Thr Thr Tyr Arg Asp Pro Asp Leu
        1620                1625                1630

Ala Thr Gly Phe Tyr Thr Tyr Gly Val Lys Val Val Tyr Pro Asn Gly
    1635                1640                1645

Glu Ser Ala Ile Glu Thr Ala Thr Leu Asn Ile Thr Ser Leu Ala Asp
   1650                1655                1660

Val Thr Ala Gln Lys Pro Tyr Thr Leu Thr Val Val Gly Lys Thr Ile
1665                1670                1675                1680

Thr Val Thr Cys Gln Gly Glu Ala Met Ile Tyr Asp Met Asn Gly Arg
            1685                1690                1695

Arg Leu Ala Ala Gly Arg Asn Thr Val Val Tyr Thr Ala Gln Gly Gly
```

-continued

```
        1700                1705                1710

His Tyr Ala Val Met Val Val Val Asp Gly Lys Ser Tyr Val Glu Lys
      1715                1720                1725

Leu Ala Val Lys
   1730


<210> SEQ ID NO 12
<211> LENGTH: 7
<212> TYPE: PRT
<213> ORGANISM: Porphyromonas gingivalis

<400> SEQUENCE: 12

Tyr Glu Gly Asp Ile Lys Asp
  1               5


<210> SEQ ID NO 13
<211> LENGTH: 9
<212> TYPE: PRT
<213> ORGANISM: Porphyromonas gingivalis

<400> SEQUENCE: 13

Lys Asp Phe Val Asp Trp Lys Asn Gln
  1               5


<210> SEQ ID NO 14
<211> LENGTH: 8
<212> TYPE: PRT
<213> ORGANISM: Porphyromonas gingivalis

<400> SEQUENCE: 14

Asp Val Tyr Thr Asp His Gly Asp
  1               5


<210> SEQ ID NO 15
<211> LENGTH: 6
<212> TYPE: PRT
<213> ORGANISM: Porphyromonas gingivalis

<400> SEQUENCE: 15

Thr His Ile Gly Ala His
  1               5
```